US008338401B2

(12) United States Patent
Xu et al.

(10) Patent No.: US 8,338,401 B2
(45) Date of Patent: Dec. 25, 2012

(54) COUMARIN-AMIDE DERIVATIVES AND ITS PREPARATION, SAID DRUG COMPOSITION AND ITS USE

(75) Inventors: Shiping Xu, Beijing (CN); Xiaoguang Chen, Beijing (CN); Song Xu, Beijing (CN); Lanmin Li, Parla Madrid (ES); Longfei Xie, Parla Madrid (ES); Hongyan Li, Parla Madrid (ES); Yan Li, Beijing (CN); Guifang Cheng, Beijing (CN)

(73) Assignee: Institute of Materia Medica Chinese Academy of Medical Sciences, Beijing (CN)

( * ) Notice: Subject to any disclaimer, the term of this patent is extended or adjusted under 35 U.S.C. 154(b) by 471 days.

(21) Appl. No.: 10/537,711

(22) PCT Filed: Dec. 5, 2003

(86) PCT No.: PCT/CN03/01046
§ 371 (c)(1),
(2), (4) Date: Nov. 28, 2005

(87) PCT Pub. No.: WO2004/050082
PCT Pub. Date: Jun. 17, 2004

(65) Prior Publication Data
US 2006/0148834 A1   Jul. 6, 2006

(30) Foreign Application Priority Data
Dec. 5, 2002   (CN) .................................. 02 1 55525

(51) Int. Cl.
*A61K 31/585* (2006.01)
*C07D 311/00* (2006.01)
*C07D 311/02* (2006.01)
(52) U.S. Cl. .......................... 514/175; 549/283; 549/290
(58) Field of Classification Search .................. 514/175; 549/283, 290
See application file for complete search history.

(56) References Cited

U.S. PATENT DOCUMENTS

| 3,567,832 | A | 3/1971 | Boschetti |
| 5,723,476 | A | 3/1998 | Larsen et al. |
| 5,981,495 | A | 11/1999 | Takagaki et al. |
| 6,407,073 | B1 | 6/2002 | Trkovnik et al. |
| 2003/0229065 | A1* | 12/2003 | Levy et al. ................... 514/185 |

FOREIGN PATENT DOCUMENTS

| CN | 1164999 | | 11/1997 |
| CN | 1207392 | | 2/1999 |
| CN | 1207392 | A * | 10/1999 |
| GB | 1 388 590 | | 3/1975 |
| JP | 49-86423 | | 8/1974 |
| JP | 06145164 | * | 5/1994 |
| JP | 7-82262 | | 3/1995 |
| JP | 2000-218940 | A | 8/2000 |
| KR | 2001-0031407 | A | 4/2001 |
| WO | WO 89/07939 | * | 2/1989 |
| WO | 93/16064 | | 8/1993 |
| WO | 02/02548 | A1 | 1/2002 |

OTHER PUBLICATIONS

El-Kerdawy, et al., Application of the Knoevenagel Condensation to 4-acetamidophenazone Derivatives, Indian J. of Chemistry, Section B: Organic Chem. Including Medicinal Chem., 26B(12), 1189-91 (1987).*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
Ukhov, et al., Synthesis and Antimicrobial Activity of 2-Iminocoumarin-3-carboxylic acid amides, Pharmaceutical Chemistry Journal, vol. 35, No. 7 (2001).*
Mabalirajan, et al., Esculetin Restores Mitochondrial Dysfunction and Reduces Allergic Asthma Features in Experimental Murine Model, The J. of Immunology, 183: 2059-2067 (2009).*
Bylov, et al., Synthesis and Anti-inflammatory Activity of N-substituted 2-oxo-2H-1-benzopyran-3-carboxyamides and Their 2-iminoanalogues, Eur. J. Med. Chem. 34, 997-1001 (1999).*
Podda, et al., Comparison of Ion Trap and Sector Instruments in the Study of Fragmentation Patterns of Coumarins, Organic Mass Spectrometry 27(11), 1220-4 (1992).*
Mohamed, et al., Some reactions with 7-hydroxy-3-carbethoxycoumarin, Journal of the Chemical Society of Pakistan, 5(4), 263-6 (1983).*
English Abstract of CN 1207392 dated Feb. 10, 1999.
Gaedeke J, Neumayer HH, Peters H: Pharmacological management of renal fibrotic disease. Expert Opin Pharmacother 2006; Abstract.
Gagliardini E, Benigni A: Role of anti-tgf-beta antibodies in the treatment of renal injury. Cytokine Growth Factor Rev 2006; 17:89-96.
Gagliardini E, Benigni A: Therapeutic potential of tgf-beta inhibition in chronic renal failure. Expert Opin Biol Ther 2007; Abstract.
Krag S, Osterby R, Chai Q, Nielsen CB, Hermans C, Wogensen L: Tgf-beta1-induced glomerular disorder is associated with impaired concentrating ability mimicking primary glomerular disease with renal failure in man. Lab Invest 2000; 80:1855-1868.
Liu Y: Renal fibrosis: New insights into the pathogenesis and therapeutics. Kidney Int 2006;69:213-217. Peters H, Border WA, Noble NA: Angiotensin ii blockade and low-protein diet produce additive therapeutic effects in experimental glomerulonephritis. Kidney Int 2000; 57:1493-1501.
Sharma VK, Bologa RM, Xu GP, Li B, Mouradian J, Wang J, Serur D, Rao V, Suthanthiran M: Intragraft tgf-beta1 mrna: A correlate of interstitial fibrosis and chronic allograft nephropathy. Kidney Int 1996; 49:1297-1303.
Chen XF, Zhang HJ, Wang HE, Zhu J, Zhou WY, Zhang H, Zhao MC, Su JM, Gao W, Zhang L, Fei K, Zhang HT, Wang HY: Transforming growth factor-beta1 induces epithelial-to-mesenchymal transition in human lung cancer cells via pi3k/akt and mek/erk1/2 signaling pathways. Mol Biol Rep 2011.
Kano MR, Bae Y, Iwata C, Morishita Y, Yashiro M, Oka M, Fujii T, Komuro A, Kiyono K, Kaminishi M, Hirakawa K, Ouchi Y, Nishiyama N, Kataoka K, Miyazono K: Improvement of cancer-targeting therapy, using nanocarriers for intractable solid tumors by inhibition of tgf-beta signaling. Proc Natl Acad Sci USA 2007;104:3460-3465.

(Continued)

Primary Examiner — Erich A Leeser
(74) Attorney, Agent, or Firm — Ladas & Parry LLP

(57) ABSTRACT

The present invention relates to novel coumarin derivatives, their carboxamides, pharmaceutical compositions containing them and their uses as drugs for kidney protection, treating drugs of hypertension, cardio-cerebrovascular diseases, non-insulin dependent diabetes, tumor, pre-cancerous lesion, and edemas.

16 Claims, No Drawings

OTHER PUBLICATIONS

Muinelo-Romay L, Colas E, Barbazan J, Alonso-Alconada L, Alonso-Nocelo M, Bouso M, Curiel T, Cueva J, Anido U, Forteza J, Gil-Moreno A, Reventos J, Lopez-Lopez R, Ahal M: High-risk endometrial carcinoma profiling identifies tgf-beta1 as a key factor in the initiation of tumor invasion. Mol Cancer Ther 2011;10:1357-1366.

Yamamura S, Matsumura N, Mandai M, Huang Z, Oura T, Baba T, Hamanishi J, Yamaguchi K, Kang HS, Okamoto T, Abiko K, Mori S, Murphy SK, Konishi I: The activated transforming growth factor-beta signaling pathway in peritoneal metastases is a potential therapeutic target in ovarian cancer. Int J Cancer 2012;130:20-28.

European Search Report dated Jan. 22, 2008 in respect of EP Application No. 03776786.0.

European first Office Action dated Nov. 10, 2008 in respect of EP Application No. 03776786.0.

European second Office Action dated Jun. 16, 2010 in respect of EP Application No. 03776786.0.

Indian first Office Action dated Jan. 15, 2007 in respect of Indian Application No. 2384DELNP/2005.

Indian Patent Certificate dated Jan. 15, 2010 in respect of Indian Application No. 2384DELNP/2005.

Russian first office Action in respect of Russian Application No. 2005121137/04.

Russian Patent Certificated in respect of Russian Application No. 2005121137/04.

First Japanese Office Action dated May 17, 2010 in respect of Japanese Application No. 2004-555972.

Chen, W., et al., Synthesis of acyl derivatives of N-substituted glycines, *Zhongguo Yaoke Daxue Xuebao*, 199, vol. 21, No. 2, pp. 65-68, (1990).

Bonsignore, L., et al., "Synthesis and pharmacological activity of 2-oxo-(2H)-1-benzopyran-3-carboxamide derivatives", European Journal of Medicinal Chemistry, 1993, vol. 28, No. 6, pp. 517-520.

Singh, V., et al. Coumarin congeners as antidepressants, *Arzneimittel-Forschung*, 1992, vol. 42, No. 8, pp. 993-996.

Shah, S, et al., "Synthesis of some new carboxanilides and amides of 8-methoxycoumarin-3-carboxylic acid as possible antifungal and antibacterial agents" Journal of the Indian Chemical Society, 1987, vol. 64, No. 11, pp. 708-709.

Mustafa, M.A., "Synthesis of some coumarin-3-(4-aminosulfonyl) carbanilide derivatives, Metabolic behavior and antimicrobial activity", *Scientia Pharmaceutica*, 1991, vol. 59, No. 3, pp. 213-220.

Bylov, I. E., et al., "Synthesis and anti-inflammatory activity of N-substituted 2-oxo-2H-1-benzopyran-3-carboxamides and their 2-imino analogs", *European Journal of Medicinal Chemistry*, 1999, vol. 34, No. 11, pp. 997-1001.

First Korean Office Action dated Dec. 21, 2007 in respect of Korean Application No. 2005-7010241.

Second Korean Office Action dated Jan. 21, 2009 in respect of Korean Application No. 2005-7010241.

Third Korean Office Action dated Aug. 25, 2009 in respect of Korean Application No. 2005-7010241.

Fourth Korean Office Action dated Mar. 19, 2010 in respect of Korean Application No. 2005-7010241.

Fifth Korean Office Action dated Jul. 23, 2010 in respect of Korean Application No. 2005-7010241.

Notice of Allowance dated Sep. 24, 2010 in respect of Korean Application No. 2005-7010241.

First Canadian Office Action, dated May 11, 2009 in respect of Canadian Application No. 2,508,573.

Second Canadian Office Action, dated Aug. 18, 2010 in respect of Canadian Application No. 2,508,573.

First Israeli Office Action dated Dec. 17, 2007 in respect of Israeli Application No. 168959.

Second Israeli Office Action dated Mar. 25, 2009 in respect of Israeli Application No. 168959.

"ACE inhibitor", Wikipedia (on-line encyclopedia), printed Jul. 16, 2012.

Zuccala, Giuseppe, et al. "Use of angiotensin-converting enzyme inhibitors and variations in cognitive performance among patients with heart failure", European Heart Journal, vol. 26, No. 3, pp. 226-233, 2004.

"Pulmonary hypertension", Wikipedia (on-line encyclopedia), printed Jul. 16, 2012.

Abstract of "Indications for ACE inhibitors in the early treatment of acute myocardial infarction: systematic overview of individual data for 100,000 patients in randomized trials. ACE Inhibitor Myocardial Infarction Collaborative Group", Circulation, Jun. 9, 1997.

Miller, Amy E., et al. "ACE inhibitors versus ARBs: comparison of practice guidelines and treatment selection considerations", Formulary, Jun. 1, 2006.

Abstract of O'Driscoll, G., et al. "Improvement in endothelial function by angiotensin-converting enzyme inhibition in non-insulin-dependent diabetes mellitus", J Am Coll Cardiol, May 1999.

* cited by examiner

COUMARIN-AMIDE DERIVATIVES AND ITS PREPARATION, SAID DRUG COMPOSITION AND ITS USE

TECHNICAL FIELD

The present invention relates to novel coumarins, their carboxamide derivatives, the preparation method thereof and the pharmaceutical compositions containing them, and their use as medicaments for kidney protection, as well as for the treatment of hypertension, cardio-cerebrovascular diseases, non-insulin dependent diabetes (NIDD), tumor, preneoplastic lesions, and edemas.

BACKGROUND ART

In 1990 the German Federal Institute of Drugs and Medicinnal Products (BfArM) published a monograph on Meliloti Herba, in which the use of melilot is indicated for symptoms and signs in chronic venous insufficiency like pains; adjuvant treatment of thrombophlebitis and lymphostasis. Scheel et al. (*Microbiol Toxins* 8: 47-66, 1972) reported that coumarins have anti-bacterial, anti-viral and anti-tumor effects. Kovach et al (*Arzeim-Forsch/Drug Res* 20: 1630-33, 1970) proved that coumarins can increase blood flow and improve myocardial ischemia. Casley-Smith, (*Vasomed* 6: 232-4, 1994), Gaffney (*J Pathol* 133: 229-42, 1981), Piller (*Br J Exp Pathol* 59: 319-26, 1978), and Knight (*Clin Sci* 77: 69-76, 1989) showed that coumarins have effects of endothelial system protection and lymph-circulation promotion, etc. Nair et al. (*Carcinogenesis* 12 (1): 65-69, 1991) reported the anticancer activity of coumarins compounds. Ishizuka et al. (U.S. Pat. No. 5,096,924) proved that substituted coumarins have anticancer activities. Marshall et al. (*J. Biol. Resp. Mod.* 8: 62, 1989) reported that coumarins have immuno-enhancing effects, such as improving the antitumor abilities by remarkably raising monocytes of patients suffering from cancer. Preuss-Ueberschar et al. (Drug Res. 34: 1305-1313, 1984) showed that the coumarins are non-teratogenitic. Takagaki, Hidetsugu et al. (EP 0, 796, 854 A1, 1997) disclosed that 3-, 4-, or 7-hydroxy or alkoxy substituted coumarins' effects in treating heart diseases. Markal et al. (WO 98/25, 608, 1998) disclosed that substituted 4-arylcoumarins can be used to treat viral infections, such as herpes zoster or herpes simplex. Trkovnik et al. (WO 99/21550, 1999) reported that 4-methyl-7-hydroxycoumarin can be used to treat or prevent nephrocirrhosis, pancreatitis, and disorders in bladder or alimentary tracts. Takagaki et al. (Jpn. Kokai Tokkyo Koho JP 07277972, 1995) reported that coumarin derivatives can inhibit rat diabetes induced by streptozotocin. Scott et al. (U.S. Pat. No. 5,723,476, 1998) disclosed that 3-carboxamide-4-hydroxy coumarin compounds are effective to the non-insulin dependent diabetes models. Han, Xingmei et al. (*Zhongguo Yaolixue Tongbao*, 15(4): 332-5, 1999) reported that 6,7-dimethoxycoumarin is effective to acute renal failure induced by endotoxins. Allen et al. (PCT Int Appl WO 2001 019396 A1 2001) reported that the TGF-$\beta$1 antagonists may be used for the treatment or prophylaxis of chronic nephritis.

In our research, a series of coumarin derivatives were synthesized and their biological activities were evaluated. For example, Xiao-long Huang et al reported substituted 3-acetyl- and 3-glyoxal-coumarin derivatives possessing good anti-mutagenic effects (*Yaoxue Xuebao* 31(6): 431-436, 1996; ibid 31(7): 509-516, 1996). Shi-ping Xu et al discovered that the coumarin retinoids show potent differentiation inducing, anti-mutagenic, and anti-carcinogenic effects (Chinese patent application No. 97116602.1, CN1207392A). Song Xu et al.'s study on 6- or 7-substitutedstyryl-coumarins, 4-styryl-coumarins and 4-, 6- or 7-substitutedphenyliminomethylene-coumarins show anticancer effects (*Yaoxue Xuebao* 35(2): 103-107, 2000; ibid 36(4): 269-273, 2001; ibid 37(2): 113-116, 2002).

Following that, upon our continued research works on coumarins compounds, a series of novel coumarins and coumarin carboxamides were synthesized. And we have found that these coumarins carboxamide compounds possess potent inhibition effects on transforming growth factor $\beta$1 (TGF-$\beta$1), which has not been reported before. The TGF-$\beta$1 inhibitors may be used for the treatment of chronic renal dysfunctions and diabetic renal dysfunctions. Meanwhile, it can also significantly decrease angiotensin II (AngII). Therefore, the compounds of present invention, may be used in the drugs for the treatment of chronic renal failure, nephritis, hypertension, even cirrhosis of liver and pulmonary fibrosis. For example, Allen et al. (PCT Int Appl WO 2001 019396 A1 2001) reported that the TGF-$\beta$ antagonists may be used for the treatment or prophylaxis of chronic nephritis.

Renal insufficiencies, particularly chronic renal failure, are the results of kidney injuries with various pathogenesis and progressive deterioration. Among the primary nephropathies, the most common is the chronic glomerulonephritis, and tubolointerstitial nephritic comes the second. Among the secondary nephropathies, diabetic nephropathy holds the first position. At present, diabetic nephropathy holds about 27% of the origin of chronic renal failures, and is still increasing; hypertensive nephropathy comes the second, about 22.7% and the glomerulonephritis comes next about 21.2% and all other pathogenesis occupy 26.6% in the origin of chronic renal insufficiencies. Being a common disease per se, nephropathies, no wonder what pathogenesis, or being immune or non-immune mechanism, unless promptly treated, may be result in chronic renal insufficiency and irreversible chronic renal injuries.

Upon the researches of the field, it shows that transforming growth factor-$\beta$1 (TGF-$\beta$1) has a close relationship with chronic renal insufficiencies caused by various pathogenesis. Four hours after nephrectomy, TGF-$\beta$1 began to increase and the renin-angiotensin system was consequently influenced. Continuously rising of TGF-$\beta$1 and over-expression will result in inhibiting the degradation of the extracellular matrix, promoting the matrix integration, and also relates to the proteinuria from renal insufficiency, as well as matrix fibrosis. Therefore, glomerular sclerosis and interstitial fibrosis have direct relationship with TGF-$\beta$1, and renin-angiotensin system and TGF-$\beta$1 are the two critical factors related to chronic renal insufficiencies. Moreover, as the inhibition of the former has close relationship with the decrease of TGF-$\beta$1 producing, this suggests that the increase of TGF-$\beta$1 might be an important pathogenesis of kidney injuries to the end-stage renal insufficiencies, and would be a new target for the screening of new anti-renal failure drugs.

Coumarin compounds possess extensive biological activities, however, it haven't been reported in the literatures that these compounds can be used for the treatment of chronic renal failures. The present compounds are a novel type compounds and can remarkably inhibit TGF-$\beta$1, which is an important pathogenesis of kidney injuries to the end-stage renal failure. It has been proved that, the compound of present invention show satisfied effects on treating renal insufficiencies.

Renal insufficiencies, especially chronic renal insufficiencies, are chronic diseases that are hard to be cured. With the continuously increase of diabetes and hypertension, the incidence of renal insufficiencies becomes more and more, and has no effective drugs or other methods for the treatment or prophylaxis up to now. Therefore, the object of the present invention is to develop new drug for the treatment of renal insufficiencies.

SUMMARY OF THE INVENTION

An object of the present invention is to overcome one or more deficiencies of the prior arts, and to provide a new coumarin, in particular to provide low toxic carboxamide derivatives thereof.

One another object of the present invention is to provide a preparation method of the coumarin carboxamide derivatives.

One aspect of the present invention relates to pharmaceutical compositions, which comprises a compound of general formula (I) or an isomer thereof as the active ingredient, and pharmaceutically acceptable carriers.

A further object of the present invention is to provide use of the novel coumarin carboxamide derivatives or the compositions thereof for the as TGF-β1 and angiotensin II (AngII) inhibitors.

A still further object of the present invention is to provide use of the novel coumarin carboxamide derivatives or the compositions thereof for the preparation of the medicaments for the treatment of kidney disorders (such as various chronic nephritis, diabetic and hypertensive renal insufficiency), non-insulin dependent diabetes, cardio-cerebrovascular diseases and hypertension.

Specifically, the first aspect of the present invention relates to the compounds of the general formula (I)

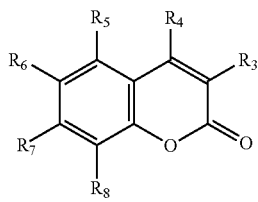

(I)

Wherein, $R^3$ is selected from the group consisting of H, carboxyl, alkyloxycarbonyl, 5'-(phenyloxadiazol-2')-yl, 5'-(pyridyl-4"-oxadizol-2')-yl,

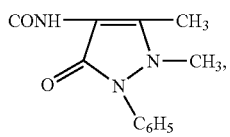

$CONHR_9$, wherein $R_9$ is selected from the group consisting of $C_2$-$C_8$ fatty acid, benzoxamido, isonicotinamido, un-substituted or mono- or multi-substituted phenyl wherein the substituent may be hydroxyl, $C_1$-$C_8$ alkoxyl, $CF_3$, carboxyl, alkyloxycarbonyl, $OCH_2CO_2H$, $NO_2$, halogen, $SO_3H$, $SO_2NHR_{11}$, wherein $R_{11}$ is selected from the group consisting of hydrogen, amidino, 2"-thiazolyl, 3"-(5"-methylisooxazolyl), 2"-pyrimidinyl, 2"-(4",6"-dimethylpyrimidinyl), 4"-(5",6"-dimethoxypyrimidinyl);

$R_4$ is selected from the group consisting of hydrogen, $CONHR_{10}$, wherein $R_{10}$ is selected from the group consisting of $C_2$-$C_8$ fatty acid, benzoxamido, isonicotiniamido, un-substituted, mono- or multi-substituted phenyl wherein the substituent may be hydroxyl, $C_1$-$C_8$ alkoxyl, $CF_3$, carboxyl, alkoxycarbonyl, $OCH_2CO_2H$, $NO_2$, halogen, $SO_3H$, $SO_2NHR_{12}$, wherein $R_{12}$ is selected from the group consisting of H, amidino, 2"-thiazolyl, 3"-(5"-methylisooxazolyl), 2"-pyrimidinyl, 2"-(4",6"-dimethyl-pyrimidinyl), 4"-(5",6"-dimethoxy pyrimidinyl);

$R_5$ is selected from the group consisting of H, $C_1$-$C_4$ alkyl;

$R_6$ is selected from the group consisting of H, $C_1$-$C_{12}$ alkyl, halogen, $NO_2$, $CONHR_{13}$, wherein $R_{13}$ is substituted phenyl;

$R_7$ is selected from the group consisting of H, hydroxyl, $C_1$-$C_4$ alkyl or alkoxyl, carboxylalkylenoxyl, $OCH_2CONHR_{14}$, wherein $R_{14}$ is selected from the group consisting of un-substituted, mono- or multi-substituted phenyl wherein the substituent may be hydroxyl, $OCH_3$, $CF_3$, $CO_2H$, $CO_2C_2H_5$, $NO_2$;

$R_8$ is selected from the group consisting of H, $C_1$-$C_4$ alkyl or alkoxyl, $NO_2$;

In order to achieve the object of the present invention, preferable compounds include, but are not limited to the following compounds:

$R_3$ is selected from the group consisting of H, COOH, $CO_2C_2H_5$, 5'-(phenyloxadiazol-2')-yl, 5'-(pyridyl-4"-oxadizol-2')-yl,

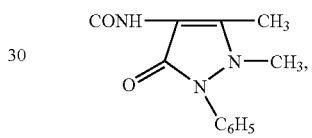

$CONHR_9$, wherein $R_9$ is n-butyric acid, o-, m-, p-phenol, o-, m-, p-carboxyl-phenyl, o-, m-, p-alkyloxycarbophenyl, methoxylphenyl, 3'-hydroxy-4'-carboxyphenyl, 3'-salicylyl, 4'-salicylyl, m-$CF_3$-phenyl, 3'-$CF_3$-4'-$NO_2$-phenyl, 2'-$CO_2H$-4'-I-phenyl, isonicotinamido, benzoxamido, 3'-carboxy-methylenoxyphenyl, 4'-amidosulfonylphenyl, 4'-guanidinosulfonylphenyl, 4'-(2"-thiazolamidosulfonyl) phenyl, 4'-(5"-methylisooxazolyl-3"-amidosulfonyl)phenyl, 4'-(pyrimidinyl-2"-amidosulfonyl)phenyl, 4'-(4",6"-dimethylpyrimidinyl-2"-amidosulfonyl)phenyl, 4'-(5",6"-dimethoxypyrimidinyl-4"-amidosulfonyl)phenyl;

$R_4$ is selected from the group consisting of H, $CONHR_{10}$, wherein $R_{10}$ is selected from the group consisting of H, 4'-$CO_2H$-phenyl, 4'-$CO_2C_2H_5$phenyl, 3'-$CF_3$-phenyl;

$R_5$ is selected from the group consisting of H, $CH_3$;

$R_6$ is selected from the group consisting of H, $C_2H_5$, n-$C_6H_{13}$, $NO_2$, $NH_2$, Cl, Br, $CONHR_{13}$, wherein $R_{13}$ is selected from the group consisting of carboxyl- and alkoxycarbonyl-substituted phenyl;

$R_7$ is selected from the group consisting of H, OH, $CH_3$, $OCH_3$, $OCH_2CONHR_{14}$, wherein $R_{14}$ is selected from the group consisting of phenyl, o-, m- and p-hydroxyphenol, o-, m- and p-carboxylphenyl, m- and p-ethoxycarbonylphenyl, m-$CF_3$-phenyl, m-$CF_3$-p-$NO_2$-phenyl, p-$CH_3O$-phenyl, 4-salicylyl, 3-salicylyl;

$R_8$ is selected from the group consisting of H, $CH_3$, $OCH_3$, $NO_2$;

In order to complete the object of the present invention, preferable compounds include, but are not limited to the compounds represented by following general formula (Ia):

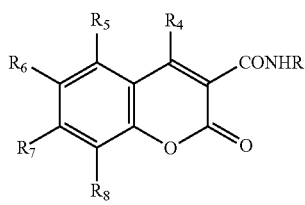

wherein $R_4$, $R_5$, $R_6$, $R_7$, $R_8$ are defined same as general formula

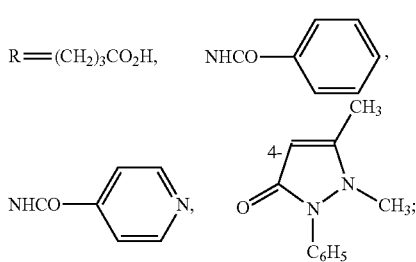

In order to complete the object of the present invention, preferable compounds include, but are not limited to the compounds represented by the following general formula (Ib):

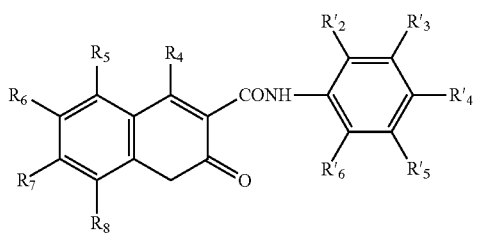

wherein $R_4$, $R_5$, $R_6$, $R_7$, $R_8$, are same as defined in general formula (I), $R'_2$ is selected from the group consisting of H, OH, $CO_2H$, etc;

$R'_3$ is selected from the group consisting of H, OH, $CO_2H$, $CF_3$, $OCH_2CO_2H$, etc;

$R'_4$ is selected from the group consisting of H, OH, $CO_2H$, $CO_2Et$, Iodo, $NO_2$, $OCH_3$, $SO_3H$, $SO_2NH_2$, $SO_2NH$ (C=NH)$NH_2$, etc;

$R'_5$ and $R'_6$ each is H;

In order to complete the object of the present invention, preferable compounds include, but are not limited to the compounds of the following tables 1 and 2:

Wherein $R_4$-$R_8$ groups are H except specified, $R'_2$-$R'_6$ groups are H except specified

TABLE 1

| No. | $R_4$—$R_8$ | $R_3$ = CONH-(phenyl with $R'_2$,$R'_3$,$R'_4$,$R'_5$,$R'_6$) | MP °C. |
|---|---|---|---|
| 1 | 7-$OCH_3$ | 4'-COOH | >300 |
| 2 | 7-$OCH_3$ | 3'-COOH | >300 |
| 3 | 7-$OCH_3$ | 2'-COOH | >300 |
| 4 | 7-$OCH_3$ | 2'-OH | >300 |
| 5 | 7-$OCH_3$ | 3'-OH | 265 |
| 6 | 7-$OCH_3$ | 4'-OH | >300 |
| 7 | 7-$OCH_3$ | 3'-OH, 4'-COOH | 279d |
| 8 | 7-$OCH_3$ | 3'-COOH, 4'-OH | 230d |
| 9 | 7-$OCH_3$ | 2'-COOH, 4'-I | >300 |
| 10 | 7-$OCH_3$ | 4'-COOEt | 247 |
| 11 | 7-$OCH_3$ | 3'-$CF_3$ | 218 |
| 12 | 7-$OCH_3$ | 3'-$CF_3$  4'-$NO_2$ | >300 |
| 13 | 7-$OCH_3$ | 4'-$SO_2NH_2$ | >300 |
| 14 | 7-$OCH_3$ | 4'-$SO_2NH$(C=NH)NH | >300 |
| 15 | 7-$OCH_3$ | 4'-$SO_2NH$-thiazole | >300 |

TABLE 1-continued

| | | | |
|---|---|---|---|
| 16 | 7-OCH$_3$ | 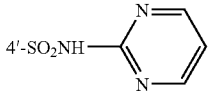 4'-SO$_2$NH-(pyrimidin-2-yl) | >300 |
| 17 | 7-OCH$_3$ | 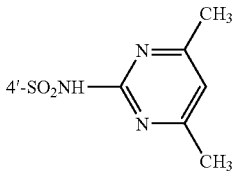 4'-SO$_2$NH-(4,6-dimethylpyrimidin-2-yl) | 298 |
| 18 | 7-OCH$_3$ | 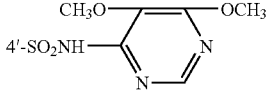 4'-SO$_2$NH-(4,6-dimethoxypyrimidin-2-yl) | 300 |
| 19 | 7-OCH$_3$ | 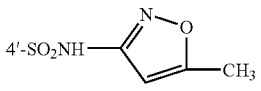 4'-SO$_2$NH-(5-methylisoxazol-3-yl) | 282d |
| 20 | 7-OCH$_3$ | 4'-OCH$_3$ | 233 |
| 21 | 7-OCH$_3$ | 4'-SO$_3$H | 284 |
| 22 | 6-Et  7-OCH$_3$ | 4'-COOH | >300 |
| 23 | 6-Et  7-OCH$_3$ | 3'-COOH | 298 |
| 24 | 6-Et  7-OCH$_3$ | 2'-COOH | 294 |
| 25 | 6-Et  7-OCH$_3$ | 4'-OH | 304 |
| 26 | 6-Et  7-OCH$_3$ | 3'-OH, 4'-COOH | 266 |
| 27 | 6-Et  7-OCH$_3$ | 3'-COOH, 4'-OH | 298 |
| 28 | 6-Et  7-OCH$_3$ | 4'-COOEt | 233 |
| 29 | 6-Et  7-OCH$_3$ | 3'-CF$_3$ | 224 |
| 30 | 6-Et  7-OCH$_3$ | 3'-CF$_3$  4'-NO$_2$ | 234 |
| 31 | 6-Et  7-OCH$_3$ | 4'-SO$_2$NH$_2$ | >300 |
| 32 | 6-Et  7-OCH$_3$ | 4'-SO$_2$NH(C=NH)NH | 299 |
| 33 | 6-Et  7-OCH$_3$ | 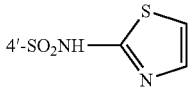 4'-SO$_2$NH-(thiazol-2-yl) | >300 |
| 34 | 6-Et  7-OCH$_3$ | 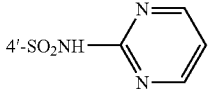 4'-SO$_2$NH-(pyrimidin-2-yl) | >300 |
| 35 | 6-Et  7-OCH$_3$ | 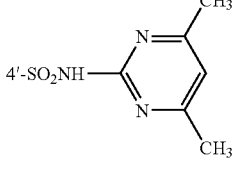 4'-SO$_2$NH-(4,6-dimethylpyrimidin-2-yl) | 278 |
| 36 | 6-Et  7-OCH$_3$ | 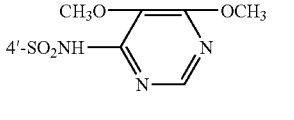 4'-SO$_2$NH-(4,6-dimethoxypyrimidin-2-yl) | 260d |
| 37 | 6-Et  7-OCH$_3$ | 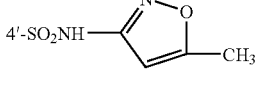 4'-SO$_2$NH-(5-methylisoxazol-3-yl) | >300 |
| 38 | 6-Et  7-OCH$_3$ | 4'-OCH$_3$ | 202 |
| 39 | 6-Et  7-OCH$_3$ | 4'-SO$_3$H | >300 |
| 40 | 7-OCH$_3$  8-CH$_3$ | 4'-COOH | >300 |
| 41 | 7-OCH$_3$  8-CH$_3$ | 3'-COOH | >300 |
| 42 | 7-OCH$_3$  8-CH$_3$ | 2'-COOH | 264 |
| 43 | 7-OCH$_3$  8-CH$_3$ | 3'-OH, 4'-COOH | 279 |
| 44 | 7-OCH$_3$  8-CH$_3$ | 3'-COOH, 4'-OH | 290 |
| 45 | 7-OCH$_3$  8-CH$_3$ | 2'-COOH, 4'-I | 284 |
| 46 | 7-OCH$_3$  8-CH$_3$ | 4'-COOEt | 270 |
| 47 | 7-OCH$_3$  8-CH$_3$ | 3'-CF$_3$ | 258 |

TABLE 1-continued

| | | | | |
|---|---|---|---|---|
| 48 | 7-OCH₃ | 8-CH₃ | 3'-CF₃, 4'-NO₂ | 252 |
| 49 | 7-OCH₃ | 8-CH₃ | 4'-SO₂NH₂ | 300 |
| 50 | 7-OCH₃ | 8-CH₃ | 4'-SO₂NH(C=NH)NH | >300 |
| 51 | 7-OCH₃ | 8-CH₃ | 4'-SO₂NH-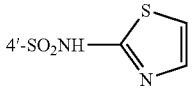 | >300 |
| 52 | 7-OCH₃ | 8-CH₃ | 4'-SO₂NH-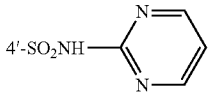 | 277 |
| 53 | 7-OCH₃ | 8-CH₃ | 4'-SO₂NH-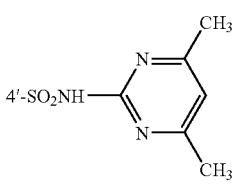 | 220d |
| 54 | 7-OCH₃ | 8-CH₃ | 4'-SO₂NH-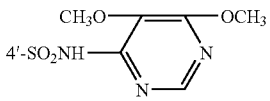 | 286 |
| 55 | 7-OCH₃ | 8-CH₃ | 4'-SO₂NH-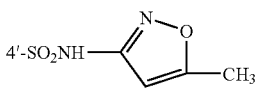 | 286 |
| 56 | 7-OCH₃ | 8-CH₃ | 4'-OCH₃ | 258 |
| 57 | 7-OCH₃ | 8-CH₃ | 4'-SO₃H | 286 |
| 58 | 7-OCH₃ | 8-OCH₃ | 4'-COOH | 315 |
| 59 | 7-OCH₃ | 8-OCH₃ | 3'-OH, 4'-COOH | 264 |
| 60 | 7-OCH₃ | 8-OCH₃ | 3'-COOH, 4'-OH | 264 |
| 61 | 7-OCH₃ | 8-OCH₃ | 4'-COOEt | 236 |
| 62 | 7-OCH₃ | 8-OCH₃ | 3'-CF₃ | 243 |
| 63 | 7-OCH₃ | 8-OCH₃ | 3'-CF₃, 4'-NO₂ | 283 |
| 64 | 7-OCH₃ | 8-OCH₃ | 3'-OCH₂COOH | 188 |
| 65 | 7-OCH₃ | 8-OCH₃ | 4'-SO₂NH₂ | 280 |
| 66 | 7-OCH₃ | 8-OCH₃ | 4'-SO₂NH(C=NH)NH | 252 |
| 67 | 5-CH₃ | 7-OCH₃ | 4'-COOH | 299 |
| 68 | 5-CH₃ | 7-OCH₃ | 3'-COOH | >300 |
| 69 | 5-CH₃ | 7-OCH₃ | 2'-COOH | >300 |
| 70 | 5-CH₃ | 7-OCH₃ | 2'-OH | 246 |
| 71 | 5-CH₃ | 7-OCH₃ | 3'-OH | 292 |
| 72 | 5-CH₃ | 7-OCH₃ | 4'-OH | 255 |
| 73 | 5-CH₃ | 7-OCH₃ | 3'-OH, 4'-COOH | 284 |
| 74 | 5-CH₃ | 7-OCH₃ | 3'-COOH 4'-OH | >300 |
| 75 | 5-CH₃ | 7-OCH₃ | 4'-COOEt | 265 |
| 76 | 5-CH₃ | 7-OCH₃ | 3'-CF₃ | 221 |
| 77 | 5-CH₃ | 7-OCH₃ | 3'-CF₃, 4'-NO₂ | >300 |
| 78 | 5-CH₃ | 7-OCH₃ | 4'-SO₂NH₂ | 283 |
| 79 | 5-CH₃ | 7-OCH₃ | 4'-SO₂NH(C=NH)NH | 293 |
| 80 | 5-CH₃ | 7-OCH₃ | 4'-SO₂NH-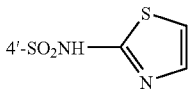 | 288 |
| 81 | 5-CH₃ | 7-OCH₃ | 4'-SO₂NH-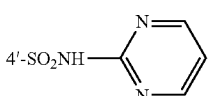 | >300 |
| 82 | 5-CH₃ | 7-OCH₃ | 4'-SO₂NH-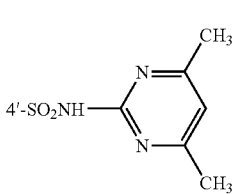 | 274d |

TABLE 1-continued

| # | | | | Structure | Value |
|---|---|---|---|---|---|
| 83 | 5-CH$_3$ | 7-OCH$_3$ | | 4'-SO$_2$NH-(4,6-dimethoxypyrimidin-5-yl) 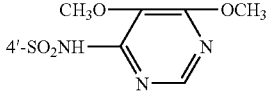 | 268 |
| 84 | 5-CH$_3$ | 7-OCH$_3$ | | 4'-SO$_2$NH-(5-methylisoxazol-3-yl) 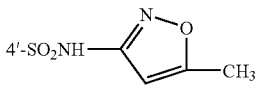 | 271 |
| 85 | 5-CH$_3$ | 7-OCH$_3$ | | 4'-OCH$_3$ | 210 |
| 86 | 6-Cl | 7-OCH$_3$ | | 4'-COOH | >300 |
| 87 | 6-Cl | 7-OCH$_3$ | | 3'-OH, 4'-COOH | 253 |
| 88 | 6-Cl | 7-OCH$_3$ | | 3'-COOH, 4'-OH | >300 |
| 89 | 6-Cl | 7-OCH$_3$ | | 4'-COOEt | 294 |
| 90 | 6-Cl | 7-OCH$_3$ | | 3'-CF$_3$ | 282 |
| 91 | 6-Cl | 7-OCH$_3$ | | 4'-SO$_2$NH$_2$ | >300 |
| 92 | 6-Cl | 7-OCH$_3$ | | 4'-SO$_2$NH(C=NH)NH | 302 |
| 93 | 6-Cl | 7-OCH$_3$ | | 4'-SO$_2$NH-(4,6-dimethoxypyrimidin-5-yl) 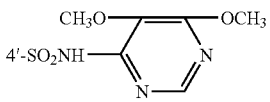 | 317 |
| 94 | 6-Br | 7-OCH$_3$ | | 4'-COOH | >300 |
| 95 | 6-Br | 7-OCH$_3$ | | 2'-COOH | 288 |
| 96 | 6-Br | 7-OCH$_3$ | | 3'-OH, 4'-COOH | 298 |
| 97 | 6-Br | 7-OCH$_3$ | | 2'-COOH, 4'-I | >300 |
| 98 | 6-Br | 7-OCH$_3$ | | 4'-COOEt | 298 |
| 99 | 6-Br | 7-OCH$_3$ | | 3'-CF$_3$ | 284 |
| 100 | 6-Br | 7-OCH$_3$ | | 4'-SO$_2$NH$_2$ | 298 |
| 101 | 6-Br | 7-OCH$_3$ | | 4'-OCH$_3$ | 262 |
| 102 | 6-nHex | 7-OCH$_3$ | | 4'-COOH | 248 |
| 103 | 6-nHex | 7-OCH$_3$ | | 2'-COOH | 272 |
| 104 | 6-nHex | 7-OCH$_3$ | | 3'-OH, 4'-COOH | 268 |
| 105 | 6-nHex | 7-OCH$_3$ | | 2'-COOH, 4'-I | 249 |
| 106 | 6-nHex | 7-OCH$_3$ | | 4'-COOEt | 160 |
| 107 | 6-nHex | 7-OCH$_3$ | | 3'-CF$_3$ | 201 |
| 108 | 6-nHex | 7-OCH$_3$ | | 4'-SO$_2$NH$_2$ | 242 |
| 109 | 6-nHex | 7-OCH$_3$ | | 4'-OCH$_3$ | 170 |
| 110 | 6-NO$_2$ | 7-OCH$_3$ | 8-OCH$_3$ | 4'-COOH | >300 |
| 111 | 6-NO$_2$ | 7-OCH$_3$ | 8-OCH$_3$ | 3'-COOH | 232 |
| 112 | 6-NO$_2$ | 7-OCH$_3$ | 8-OCH$_3$ | 4'-OCH$_3$ | 256 |
| 113 | 6-NO$_2$ | 7-OCH$_3$ | 8-OCH$_3$ | 3'-OH | 160 |
| 114 | 6-NO$_2$ | 7-OCH$_3$ | 8-OCH$_3$ | 2'-OH | 217 |
| 115 | 6-NO$_2$ | 7-OCH$_3$ | 8-OCH$_3$ | 4'-COOEt | 193 |
| 116 | 6-NO$_2$ | 7-OCH$_3$ | 8-OCH$_3$ | 3'-OH, 4'-COOH | >300 |
| 117 | 6-NO$_2$ | 7-OCH$_3$ | 8-OCH$_3$ | 3'-COOH, 4'-OH | 266d |
| 118 | 6-NO$_2$ | 7-OCH$_3$ | 8-OCH$_3$ | 3'-CF$_3$ | 218 |
| 119 | 6-NO$_2$ | 7-OCH$_3$ | 8-OCH$_3$ | 3'-CF$_3$, 4'-NO$_2$ | 217 |
| 120 | 6-NO$_2$ | 7-OCH$_3$ | 8-OCH$_3$ | 4'-SO$_2$NH$_2$ | 290d |
| 121 | 6-NO$_2$ | 7-OCH$_3$ | 8-OCH$_3$ | 4'-SO$_2$NH(C=NH)NH | 284 |
| 122 | 6-NO$_2$ | 7-OCH$_3$ | 8-OCH$_3$ | 4'-SO$_2$NH-(pyrimidin-2-yl) 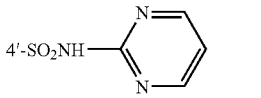 | 190d |
| 123 | 6-NO$_2$ | 7-OCH$_3$ | 8-OCH$_3$ | 4'-SO$_2$NH-(4,6-dimethoxypyrimidin-5-yl) 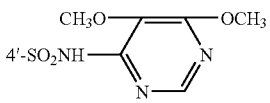 | 220d |
| 124 | 6-NO$_2$ | 7-OCH$_3$ | 8-OCH$_3$ | 4'-SO$_2$NH-(thiazol-2-yl) 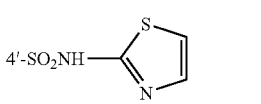 | 200d |
| 125 | 6-C$_2$H$_5$, 7-OH | | 8-NO$_2$ | 4'-COOH | 234 |
| 126 | 6-C$_2$H$_5$, 7-OH | | 8-NO$_2$ | 4'-OCH$_3$ | 218d |
| 127 | 6-C$_2$H$_5$, 7-OH | | 8-NO$_2$ | 3'-OH | >300 |
| 128 | 6-C$_2$H$_5$, 7-OH | | 8-NO$_2$ | 2'-OH | 248d |
| 129 | 6-C$_2$H$_5$, 7-OH | | 8-NO$_2$ | 4'-COOEt | 160 |
| 130 | 6-C$_2$H$_5$, 7-OH | | 8-NO$_2$ | 3'-OH, 4'-COOH | >300 |
| 131 | 6-C$_2$H$_5$, 7-OH | | 8-NO$_2$ | 3'-COOH, 4'-OH | >300 |
| 132 | 6-C$_2$H$_5$, 7-OH | | 8-NO$_2$ | 3'-CF$_3$ | 169 |
| 133 | 6-C$_2$H$_5$, 7-OH | | 8-NO$_2$ | 4'-SO$_2$NH$_2$ | 206d |

TABLE 1-continued

| | | | |
|---|---|---|---|
| 134 | 6-C$_2$H$_5$, 7-OH 8-NO$_2$ | 4'-SO$_2$NH(C=NH)NH | 181 |
| 135 | 6-C$_2$H$_5$, 7-OH 8-NO$_2$ | 4'-SO$_2$NH— 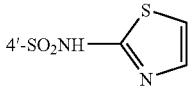 | >300 |
| 136 | 6-C$_2$H$_5$ 7-OCH$_3$ 8-NO$_2$ | 4'-COOH | 273 |
| 137 | 6-C$_2$H$_5$ 7-OCH$_3$ 8-NO$_2$ | 4'-OH | 252 |
| 138 | 6-C$_2$H$_5$ 7-OCH$_3$ 8-NO$_2$ | 4'-OCH$_3$ | 169 |
| 139 | 6-C$_2$H$_5$ 7-OCH$_3$ 8-NO$_2$ | 4'-COOEt | 186 |
| 140 | 6-C$_2$H$_5$ 7-OCH$_3$ 8-NO$_2$ | 4'-SO$_2$NH(C=NH)NH | 206d |
| 141 | 6-NO$_2$, 7-OH, 8-CH$_3$ | 4'-COOH | >300 |
| 142 | 6-NO$_2$, 7-OH, 8-CH$_3$ | 2'-COOH | 227 |
| 143 | 6-NO$_2$, 7-OH, 8-CH$_3$ | 4'-OH | >300 |
| 144 | 6-NO$_2$, 7-OH, 8-CH$_3$ | 3'-OH | >300 |
| 145 | 6-NO$_2$, 7-OH, 8-CH$_3$ | 2'-OH | >300 |
| 146 | 6-NO$_2$, 7-OH, 8-CH$_3$ | 4'-OCH$_3$ | 254 |
| 147 | 6-NO$_2$, 7-OH, 8-CH$_3$ | 4'-COOEt | >300 |
| 148 | 6-NO$_2$, 7-OH, 8-CH$_3$ | 3'-OH, 4'-COOH | 271 |
| 149 | 6-NO$_2$, 7-OH, 8-CH$_3$ | 3'-COOH, 4'-OH | >300 |
| 150 | 6-NO$_2$, 7-OH, 8-CH$_3$ | 3'-CF$_3$ | 231 |
| 151 | 6-NO$_2$, 7-OH, 8-CH$_3$ | 3'-CF$_3$, 4'-NO$_2$ | 226 |
| 152 | 6-NO$_2$, 7-OH, 8-CH$_3$ | 4'-SO$_2$NH$_2$ | >300 |
| 153 | 6-NO$_2$, 7-OH, 8-CH$_3$ | 4'-SO$_2$NH(C=NH)CH$_2$ | >300 |
| 154 | 6-NO$_2$, 7-OH, 8-CH$_3$ | 4'-SO$_2$NH— 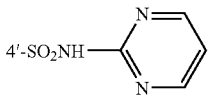 | >300 |
| 155 | 6-NO$_2$, 7-OH, 8-CH$_3$ | 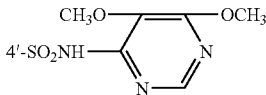 | 254 |
| 156 | 6-NO$_2$, 7-OH, 8-CH$_3$ | 4'-SO$_2$NH— 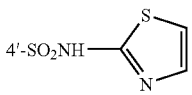 | >300 |
| 157 | 6-NO$_2$, 7-OH, 8-CH$_3$ | 2'-COOH, 4'-I | 262 |
| 158 | 6-NO$_2$, 7-OCH$_3$, 8-CH$_3$ | 4'-COOH | 301 |
| 159 | 6-NO$_2$, 7-OCH$_3$, 8-CH$_3$ | 3'-COOH | 280 |
| 160 | 6-NO$_2$ 7-OCH$_3$, 8-CH$_3$ | 2'-COOH | 282 |
| 161 | 6-NO$_2$, 7-OCH$_3$, 8-CH$_3$ | 4'-OH | >300 |
| 162 | 6-NO$_2$, 7-OCH$_3$, 8-CH$_3$ | 3'-OH | 231 |
| 163 | 6-NO$_2$, 7-OCH$_3$, 8-CH$_3$ | 2'-OH | 285 |
| 164 | 6-NO$_2$, 7-OCH$_3$, 8-CH$_3$ | 4'-OCH$_3$ | 209 |
| 165 | 6-NO$_2$, 7-OCH$_3$, 8-CH$_3$ | 4'-COOEt | 230 |
| 166 | 6-NO$_2$, 7-OCH$_3$, 8-CH$_3$ | 3'-OH, 4'-COOH | 249 |
| 167 | 6-NO$_2$, 7-OCH$_3$, 8-CH$_3$ | 3'-CF$_3$ | 182 |
| 168 | 6-NO$_2$, 7-OCH$_3$, 8-CH$_3$ | 3'-CF$_3$, 4'-NO$_2$ | 236 |
| 169 | 6-NO$_2$, 7-OCH$_3$, 8-CH$_3$ | 4'-SO$_2$NH(C=NH)NH | >300 |
| 170 | 6-NO$_2$, 7-OCH$_3$, 8-CH$_3$ | 4'-SO$_2$NH$_2$ | 301 |
| 171 | 6-NO$_2$, 7-OCH$_3$, 8-CH$_3$ | 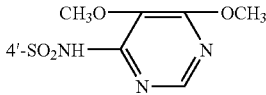 | 276 |
| 172 | 6-NO$_2$, 7-OCH$_3$, 8-CH$_3$ | 4'-SO$_2$NH— 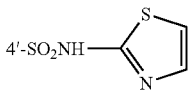 | 270 |
| 173 | 6-NO$_2$, 7-OCH$_3$, 8-CH$_3$ | 4'-SO$_2$NH— 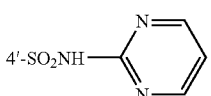 | 299 |
| 174 | 6-NO$_2$, 7-OH, 8-NO$_2$ | 4'-COOH | >300 |
| 175 | 6-NO$_2$, 7-OH, 8-NO$_2$ | 4'-OH | 260 |
| 176 | 6-NO$_2$, 7-OH, 8-NO$_2$ | 3'-OH | >300 |
| 177 | 6-NO$_2$, 7-OH, 8-NO$_2$ | 2'-OH | >300 |
| 178 | 6-NO$_2$, 7-OH, 8-NO$_2$ | 4'-OCH$_3$ | >300 |
| 179 | 6-NO$_2$, 7-OH, 8-NO$_2$ | 4'-COOEt | 281 |

TABLE 1-continued

| | | | |
|---|---|---|---|
| 180 | 6-NO₂, 7-OH, 8-NO₂ | 3'-CF₃ | 197 |
| 181 | 6-NO₂, 7-OH, 8-NO₂ | 4'-SO₂NH₂ | >300 |
| 182 | 6-NO₂, 7-OH, 8-NO₂ | 4'-SO₂NH(C=NH)NH | 216 |
| 183 | 6-NO₂, 7-OH, 8-NO₂ | 4'-SO₂NH–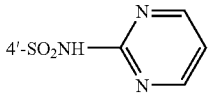 | >300 |
| 184 | 6-NO₂, 7-OH, 8-NO₂ | 4'-SO₂NH–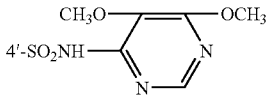 | 170 |
| 185 | 6-NO₂, 7-OH, 8-NO₂ | 4'-SO₂NH–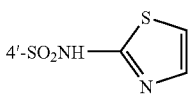 | >300 |
| 186 | 6-NO₂, 7-OH, 8-NO₂ | 2'-COOH | 285 |
| 187 | 6-NO₂, 7-OCH₃  8-NO₂ | 4'-OH | 257 |
| 188 | 6-NO₂, 7-OCH₃  8-NO₂ | 4'-COOEt | 236 |
| 189 | 6-NO₂, 7-OCH₃  8-NO₂ | 4'-OCH₃ | 205 |
| 190 | 6-Cl  7-OH  8-NO₂ | 4'-OCH₃ | 285 |
| 191 | 6-Cl  7-OH  8-NO₂ | 4'-SO₂NH(C=NH)NH | 300d |
| 192 | 6-Cl  7-OH  8-NO₂ | 3'-OH  4'-COOH | >300 |
| 193 | 5-CH₃, 6-, 8-(NO₂)₂  7-OH | 4'-COOH | >300 |
| 194 | 5-CH₃6-, 8-(NO₂)₂, 7-OH | 3'-COOH | 246 |
| 195 | 5-CH₃6-, 8-(NO₂)₂  7-OH | 2'-COOH | 214 |
| 196 | 6-CH₃6-, 8-(NO₂)₂  7-OH | 4'-OCH₃ | 242 |
| 197 | 5-CH₃6-, 8-(NO₂)₂  7-OH | 4'-COOEt | 244 |
| 198 | 5-CH₃6-, 8-(NO₂)₂  7-OH | 4'-SO₂NH₂ | 256 |
| 199 | 5-CH₃, 6-, 8-(NO₂)₂  7-OH | 4'-SO₂NH(C=NH)NH | >300 |
| 200 | 5-CH₃6-, 8-(NO₂)₂  7-OH | 4'-SO₂NH–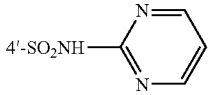 | >300 |
| 201 | 5-CH₃6-, 8-(NO₂)₂  7-OH | 4'-SO₂NH–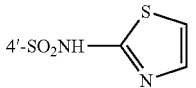 | 220 |
| 202 | 5-CH₃6-, 8-(NO₂)₂  7-OH | 4'-SO₂NH–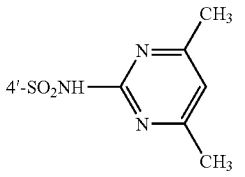 | 276 |

| | R₄—R₈ | R₃ | |
|---|---|---|---|
| 203 | 7-OCH₃ | CONH(CH)₃CO₂H | 193 |
| 204 | 7-OCH₃ | 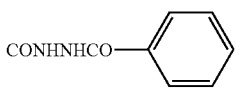 | 293 |
| 205 | 7-OCH₃ | 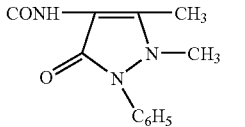 | 248 |
| 206 | 7-OCH₃ | 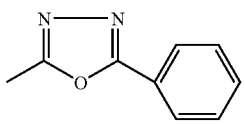 | 238 |
| 207 | 6-C₂H₅, 7-OCH₃ | CONH(CH)₃CO₂H | 226 |

TABLE 1-continued
| | | | |
|---|---|---|---|
| 208 | 6-C$_2$H$_5$, 7-OCH$_3$ | 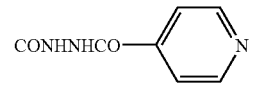 | 293 |
| 209 | 6-C$_2$H$_5$, 7-OCH$_3$ | 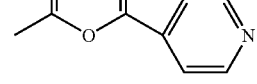 | 196 |
| 210 | 5-CH$_3$, 7-OCH$_3$ | 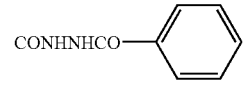 | 248 |
| 211 | 5-CH$_3$, 7-OCH$_3$ | 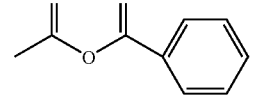 | 176 |
| 212 | 5-CH$_3$, 7-OCH$_3$ | 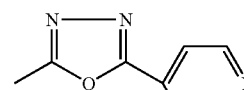 | 240 |
| 213 | 7-OCH$_3$, 5-CH$_3$ | 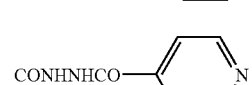 | 254 |
| 214 | 7-OCH$_3$, 8-CH$_3$ | 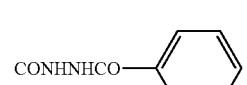 | 254 |
| 215 | 7-OCH$_3$  8-CH$_3$ | 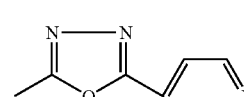 | 278 |
| 216 | 7-OCH$_3$  8-CH$_3$ | 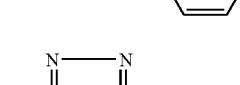 | 270 |
| 217 | 6-Br  7-OCH$_3$ | 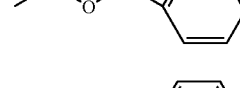 | 248 |
| 218 | 6-Br  7-OCH$_3$ | 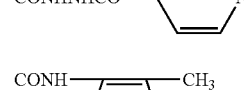 | >300 |
| 219 | 6-Br  7-OCH$_3$ | 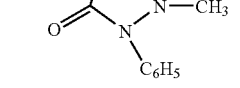 | 295 |
| 220 | 6-n-C$_6$H$_{13}$  7-OCH$_3$ | 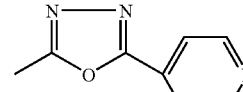 | 198 |

TABLE 1-continued

| No. | | | | MP °C |
|---|---|---|---|---|
| 221 | 6-n-C$_6$H$_{13}$ | 7-OCH$_3$ | [5-methyl-2-(pyridin-4-yl)-1,3,4-oxadiazole] | 196 |
| 222 | 6-n-C$_6$H$_{13}$ | 7-OCH$_3$ | CONH—[1,5-dimethyl-2-phenyl-pyrazol-3(2H)-one-4-yl], CH$_3$, N—CH$_3$, C$_6$H$_5$ | 139 |
| 223 | 6-NO$_2$, 7-OH, 8-CH$_3$ | | CONHNHCO—[pyridin-4-yl] | >300 |
| 224 | 6-NO$_2$, 7-OCH$_3$, 8-CH$_3$ | | CONHNHCO—[pyridin-4-yl] | 220 |
| 225 | 6-NO$_2$ | 7,8-(OCH$_3$)$_2$ | CONHNHCO—[pyridin-3-yl] | 199 |
| 226 | 6-NO$_2$ | 7,8-(OCH$_3$)$_2$ | CONHNHCO—[phenyl] | >300 |

TABLE 2

| No. | R$_3$ | R$_4$ | R$_5$ | R$_6$ | R$_7$ | R$_8$ | MP °C |
|---|---|---|---|---|---|---|---|
| 227 | CO$_2$C$_2$H$_5$ | H | H | NO$_2$ | OCH$_3$ | OCH$_3$ | 191 |
| 228 | CO$_2$H | H | H | NO$_2$ | OCH$_3$ | OCH$_3$ | 188 |
| 229 | CO$_2$C$_2$H$_5$ | H | H | NO$_2$ | OH | CH$_3$ | 210 |
| 230 | CO$_2$H | H | H | NO$_2$ | OH | CH$_3$ | 251 |
| 231 | CO$_2$C$_2$H$_5$ | H | H | NH$_2$ | OH | CH$_3$ | 203 |
| 232 | CO$_2$H | H | H | NO$_2$ | OCH$_3$ | CH$_3$ | 178 |
| 233 | CO$_2$C$_2$H$_5$ | H | H | C$_2$H$_5$ | OH | NO$_2$ | 143 |
| 234 | CO$_2$H | H | H | C$_2$H$_5$ | OH | NO$_2$ | 178 |
| 235 | CO$_2$C$_2$H$_5$ | H | H | C$_2$H$_5$ | OCH$_3$ | NO$_2$ | 140 |
| 236 | CO$_2$H | H | H | C$_2$H$_5$ | OCH$_3$ | NO$_2$ | 176 |
| 237 | CO$_2$C$_2$H$_5$ | H | H | NO$_2$ | OH | NO$_2$ | 176 |
| 238 | CO$_2$H | H | H | NO$_2$ | OH | NO$_2$ | 296 |
| 239 | CO$_2$C$_2$H$_5$ | H | H | NO$_2$ | OCH$_3$ | NO$_2$ | 152 |
| 240 | CO$_2$H | H | H | NO$_2$ | OCH$_3$ | NO$_2$ | 246 |
| 241 | CO$_2$C$_2$H$_5$ | H | H | Cl | OH | NO$_2$ | 195 |
| 242 | CO$_2$H | H | H | Cl | OH | NO$_2$ | >300 |
| 243 | CO$_2$H | H | CH$_3$ | NO$_2$ | OH | NO$_2$ | 211 |
| 244 | CO$_2$C$_2$H$_5$ | H | CH$_3$ | NO$_2$ | OH | NO$_2$ | 104 |
| 245 | H | CONH—[C$_6$H$_4$]—CO | H | H | CH$_3$ | H | 223 |
| 246 | H | CONH—[C$_6$H$_4$]—CO | H | H | CH$_3$ | H | >300 |
| 247 | H | CONH—[C$_6$H$_4$-CF$_3$] | H | H | CH$_3$ | H | 197 |
| 248 | H | CH$_3$ | H | H | OCH$_2$CONH—[C$_6$H$_5$] | H | 230 |

TABLE 2-continued

| No. | R₃ | R₄ | R₅ | R₆ | R₇ | R₈ | MP ° C. |
|---|---|---|---|---|---|---|---|
| 249 | H | CH₃ | H | H | OCH₂CONH-C₆H₄-OH (4-OH) | H | 220 |
| 250 | H | CH₃ | H | H | OCH₂CONH-C₆H₄-OH (3-OH) | H | 240 |
| 251 | H | CH₃ | H | H | OCH₂CONH-C₆H₄-OH (2-OH) | H | 196 |
| 252 | H | CH₃ | H | H | OCH₂CONH-C₆H₄-COOH (4-COOH) | H | 304 |
| 253 | H | CH₃ | H | H | OCH₂CONH-C₆H₄-COOH (3-COOH) | H | >300 |
| 254 | H | CH₃ | H | H | OCH₂CONH-C₆H₄-COOH (2-COOH) | H | 296 |
| 255 | H | CH₃ | H | H | OCH₂CONH-C₆H₄-COOEt (4-COOEt) | H | 207 |
| 256 | H | CH₃ | H | H | OCH₂CONH-C₆H₄-COOEt (3-COOEt) | H | 157 |
| 257 | H | CH₃ | H | H | OCH₂CONH-C₆H₄-CF₃ | H | 243 |
| 258 | H | CH₃ | H | H | OCH₂CONH-C₆H₃(CF₃)(NO₂) | H | 301 |
| 259 | H | CH₃ | H | H | OCH₂CONH-C₆H₄-OCH₃ | H | 180 |
| 260 | H | CH₃ | H | H | OCH₂CONH-C₆H₃(COOH)(OH) | H | 215 |
| 261 | H | CH₃ | H | H | OCH₂CONH-C₆H₃(OH)(COOH) | H | 277 |

TABLE 2-continued

| No. | R₃ | R₄ | R₅ | R₆ | R₇ | R₈ | MP °C. |
|---|---|---|---|---|---|---|---|
| 262 | H | CH₃ | H | H | OCH₂CONH-C₆H₄-CF₃ | CH₃ | 216 |
| 263 | H | CH₃ | H | H | OCH₂CONH-C₆H₄-COOEt | CH₃ | 205 |
| 264 | H | CH₃ | H | H | OCH₂CONH-C₆H₃(OH)-COOH | CH₃ | 260 |
| 265 | $R_3 = R_4 = R_5 = R_7 = R_8 = H$ | | | $R_6 =$ CONH-C₆H₄-COOEt | | | 214 |
| 266 | $R_3 = R_4 = R_5 = R_7 = R_8 = H$ | | | $R_6 =$ CONH-C₆H₄-COOH | | | 300 |

In this description, the term "halogen" indicates Fluoro, Chloro, Bromo and Iodo. The terms "lower alkane", "lower alkyl" mean linear or branched alkanes and alkyls having 1-6 carbon atoms.

According to the present invention, the compounds may have isomers, generally the said "compounds of the present invention" includes isomers thereof.

The compounds of the present invention may contain cis-/trans-isomers of a double bond, asymmetric center with S- and R-configurations, and include all the potential stereoscopic isomers and mixtures of two or more isomers. In case that cis-/trans-isomers exist, the present invention also relates to the cis- and trans-isomer and their mixtures, and a pure isomer may be separated according to the conventional methods or synthesized from stereo-selective reagents if necessary.

According to the embodiments of present invention, said compounds may also include the pharmaceutically acceptable salts and hydrate(s), esters, or pro-drugs thereof.

According to the present invention, it is also related to the preparation methods of the compounds of the present invention, which are prepared via nitrating or bi-nitrating various substituted 3-esteryl or 3-carboxy-coumarins, thus to obtain part of the target compounds of present invention and meanwhile the intermediates for the target compounds; reacting the intermediated acids, 3-carboxy-substituted various substituted coumarins, 4-carboxy-substituted various substituted coumarins, 6-carboxy-substituted various substituted coumarins and 7-carboxy-substituted various substituted coumarins with corresponding substituted amines to achieve the target compounds.

The amidating reaction is carried out with corresponding reactants and catalysts, and in the suitable solvents. Said reactants include phosphorus trichloride, phosphorus oxychloride, phosphorus pentachloride, thionyl chloride, 1,3-dicyclohexylcarbodiimide, dipyridylcarbonate (2-DPC), 1,3-diisopropylcarbodiimide (DIPC), and 1-(3-dimethylaminopropyl)-3-ethylcarbodiimide (EDCI), etc. Preferable reactants are phosphorus pentachloride, phosphorus trichloride and thionyl chloride, more preferable reactants are phosphorus pentachloride and thionyl chloride. Catalytic agents for the preparation of the compounds of present invention include tertiary amines, pyridine, 4-dimethylaminopyridine and 4-pyrrolidylpyridine, preferably tertiary amines and pyridine, more preferably pyridine. The reaction is carried out in a suitable solvent or the above condensation agent, such as anhydrous aprotic solvent, dimethylsulfoxide (DMSO), toluene, dichloromethane, 1,2-dichloroethane, ethylene glycol dimethyl ether, tetrahydrofuran and N,N-dimethylformamide (DMF), preferably toluene, DMSO and DMF, more preferably toluene and DMF.

The reaction temperature is 10~110° C., preferably 20~90° C., more preferably 30~80° C., particularly preferably 50~70° C.

The synthetic routes are specifically explained in the following routes IIa, IIb, IIc, IId, IIe and IIf.

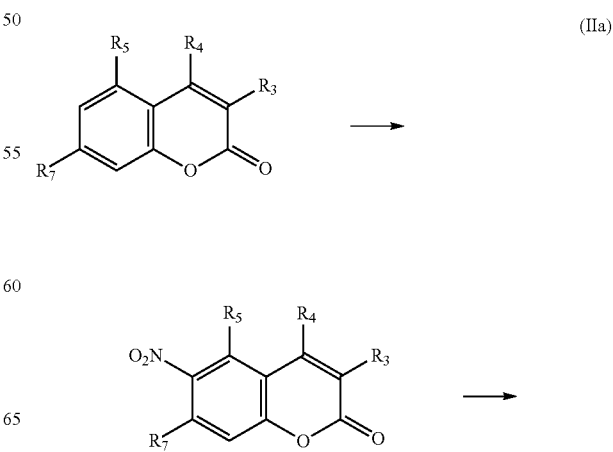

-continued

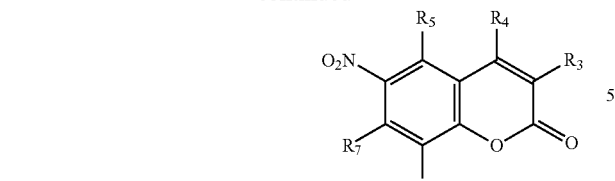

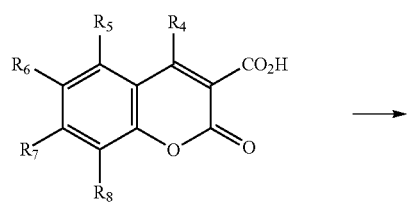
(IIb)

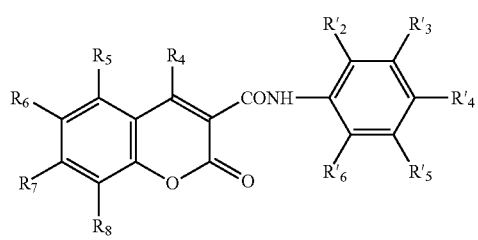

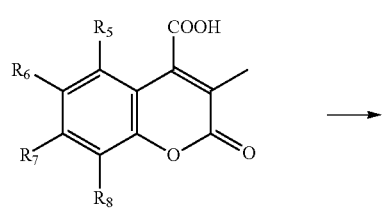

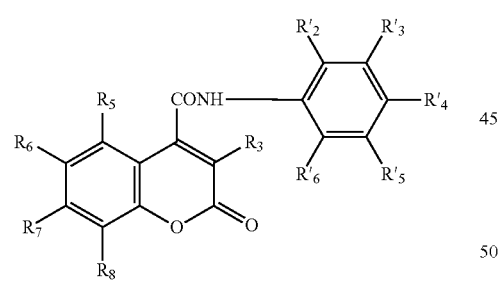

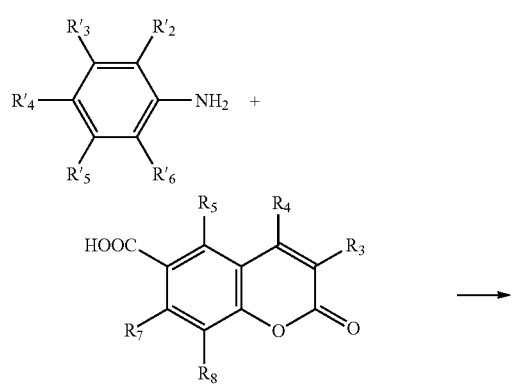
(IId)

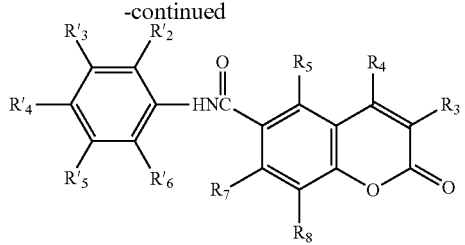

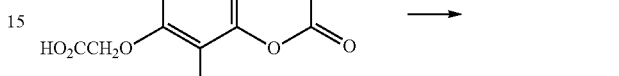
(IIe)

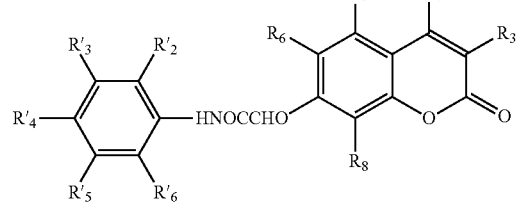

(IIf)

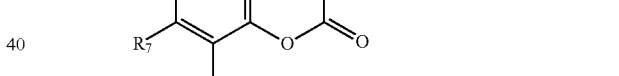

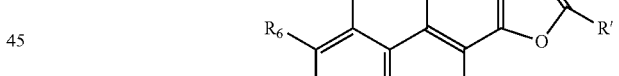

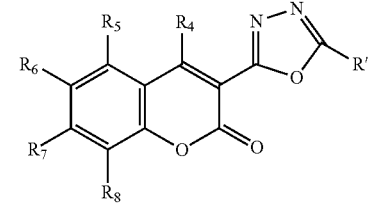

Thus, the present invention also relates to a pharmaceutical composition containing a compound of present invention as active ingredient and conventionally pharmaceutical excipients or auxiliaries. Generally the composition may comprise the compound of present invention from 0.1 to 95% by weight.

The composition of present invention may be prepared by the common methods according to the art. For this purpose, the compounds of the present invention may be combined with one or more solid, semi-solid or liquid excipients and/or auxiliaries, to prepare a suitable administration form or dosage forms for human or animal use.

The compounds of the present invention or compositions containing them may be administered in the unit dosage forms and the administration routes, which can be oral or parenteral, such as oral, intramusculary, subcutaneously, nasal, oral mucosa, transdermal, intraperitoneal or rectal, etc.

The compounds of the present invention or compositions containing them may be administered via injection, including intravenous, intramuscular, subcutaneous, intradermal, and acupoint etc.

The administration forms may be liquid or solid forms. For example the liquid forms may be solutions, colloids, fine particles, emulsion, suspensions and the like. Other forms may be such as tablets, capsules, sprays, dripping pills, aerosols, pills, powders, solutions, suspensions, emulsions, granules, suppositorys, freeze-dried powder for injections and the like.

The present compounds can be prepared as normal preparations, or sustained-release, controlled-release or targeted preparations and various fine particle delivery systems.

In order to prepare unit administration forms to tablets, carriers well known in the art can be used. Carriers such as, diluents and absorbents, such as starch, dextrin, calcium sulfate, lactose, mannitol, sucrose, sodium chloride, glucose, urea, calcium carbonate, kaolin, microcrystallinecellulose, aluminum silicate and the like; moist and binding agents for example water, glycerol, polyethyleneglycol, ethanol, propanol, starch paste, dextrin, syrups, honey, glucose solution, Arabia gum, gelatin, sodium carboxymethylcelluloses, lacta, methylcellulose, potassium phosphate, polyvinylpyrrolidone and the like; disintegrants, for example dry starch, alginates, agar powders, laminarin, sodium hydrogencarbonate-citric acid, calcium carbonate, polyoxyethylene-sorbitol fatty acid esters, sodium lauryl sulfonate, methylcellulose, ethylcellulose and the like; disintegrant inhibitors, such as sucrose, glycerol tristearate, cocoa butter, hydrogenated oil and the like; absorb-promotors, for example quaternary ammonium salts, sodium lauryl sulfate and the like; lubricants, for example talc, silica, corn starch, stearates, boric acid, liquid paraffin, polyethyleneglycol and the like. The tablets may be further coated, for example sugarcoating, film coating, enteric coating, or two or multi-layered tablets.

To prepare pills from the administration units, carriers well known in the art can be used. Carriers such as, diluents and absorbents, such as glucose, lactose, starch, cocoa butter, hydrogenated vegetable oils, polyvinylpyrrolidone, Gelucire, kaolin, talc and the like; binding agents such as arabia gum, tragacanth, gelatin, ethanol, honey, liquid-sugars, rice pastes or flour pastes and the like; disintegrants such as agar powder, dry starch, alginates, sodium lauryl sulfonate, methylcellulose, ethylcellulose and etc.

To prepare capsules from the administration units, the compounds of present invention may be mixed with the above carrier(s), and the so obtained mixtures are packaged into hard or soft capsules. Alternatively, the present compounds may also be prepared into microcapsules, and can be used as suspension in a hydrous media, or packaged into hard capsules or injections.

To prepare the injection dosage forms, the compounds of present invention may be formulated into solutions, suspensions, emulsions, freeze dried powders for injections. Such formulations may be hydrous or anhydrous, which may contain one or two or more pharmaceutically acceptable carrier(s), diluents, preservatives, surfactants or dispersing agents. For example, diluents are selected from water, ethanol, polyethylene glycol, 1,3-propylene glycol, ethoxyisostearyl alcohol, polyoxyisostearyl alcohol, polyoxyethylene-sorbitol fatty acid esters and the like. In addition, to prepare the isotonic injections, sodium chloride, glucose or glycerol can be added to the injection solution, further, solubilizing agents, buffering agents, pH-modulators and the like can also be added.

Also, if desired, coloring agents, preservatives, perfumes, correctants, sweetening agents and the like, can also be added to the pharmaceutical preparation.

For achieving administering purpose and enhancing treating effect, the compounds or pharmaceutical compositions of the present invention may be administered by any known methods. The administering dosage of the present invention may extensively be varied by depending on a number of factors, for example the seriousness of the diseases to be treated or prevented, sex, age, body weights, disposition and individual differences of the patients or animals, administering routes or number of times, treating purposes, etc. In general, the effective dosages of the pharmaceutically active ingredients are known to those skilled in the art, the real administering dose can be suitably adjusted based on the exact dosage contained in the formulations to achieve the treatment or prophylaxis purposes.

The daily suitable ranges of dosages of the compounds of present invention are within 0.001-150 mg/kg body weight, preferably 0.1-100 mg/kg, more preferably 1-60 mg/kg, most preferably 2-30 mg/kg. These doses can be administered in one single dose or divided into several doses, for example twice, three or four times per day, which depends on the experiences of doctors and the other different therapeutic means.

The total dose of each treatment may be administered in one portion or divided into multi portions, depending on the total dose. The compound or the pharmaceutical compositions of present invention may be adopted alone or in combination with other drugs, in the latter case, the dose may also be adjusted.

The activities and effects of the compounds and/or compositions of the present invention may be determined via in vitro and in vivo tests, such as TGF-β1 antagonism, treating of the renal insufficiencies and the like, which are all known in the filed. In recent years, researches have confirmed that TGF-β1 is one of most critical factors resulting in the progressive renal failure with glomerulosclerosis and interstitial fibrosis.

Pharmacological tests show that the compounds of the present invention possess effects of blocking the binding of TGF-β1 with the receptors and inhibiting the production of TGF-β1. Of all the 33 subject compounds in 10 μg/ml doses, 11 compounds possess activities of exceeding 50%, 8 compounds possess activities of exceeding 60%, 7 compounds possess activities of exceeding 70%, 5 compounds possess activities of exceeding 80%, and 4 compounds possess activities of exceeding 90%.

In the cell growth inhibition model of mink pulmonary epithelial cells induced by TGF-β1, of all the 5 subject compounds, 3 compounds possess activities of exceeding 60%, 2 compounds possess activities of exceeding 70%, and 1 compound possesses activity of exceeding 90%. Thus, the present compounds can be used for the treatment or prophylaxis of chronic renal disorders, including: a) primary nephropathies, commonly such as, the chronic glomerulonephritis, interstitial nephritis, chronic pyelonephritis and the like; b) secondary nephropathies, commonly such as, chronic diabetic nephropathy, hypertensive nephropathy, lupus nephropathy and the like; c) congenital and obstructive diseases such as polycystic kidney, posterior urethral valve disorders, neurogenic bladder hyperplasia, prostatic hyperplasia, urinary lithiasis, etc.

Additional researches show that the compounds of the present invention can remarkably inhibit the effect of Ang II (P<0.01). As mentioned above, TGF-β1 and the renin-angiotesin system are closely related with renal insufficiencies having multi pathogenesis. TGF-β1 and the renin-angiotensin system are the two most critical factors in the progressive deterioration of renal disorders and the inhibition of Ang II has a close relationship with the reduction of TGF-β1. As Ang II plays an important role in the onset of various types of hypertensions, the compounds of the present invention may be used for the treatment of renal hypertensions, diabetic hypertensions, peripheral vascular hypertensions and cardio-cerebrovascular diseases having the above pathogenesis.

In vivo tests on the model of chronic renal failure induced by a 5/6 nephrectomy in rats showes that, comparing with the positive controls Benazepril and Losartan, the compounds of the present invention superiors than Benazepril and corresponds to (slightly better than) Losartan on reducing the blood serum urea nitrogen (BUN) and creatinine (Cre), as well as inhibiting TGF-β1 and Ang II.

In the tests of the renal interstitial fibrosis model from unilateral ureteral ligation in rats, the subject compound 149 is better than Benazepril and corresponds to (slightly better than) Losartan, and the pathological results show that the compound of present invention are better than Benazepril and correspond to Losartan.

The tested compounds have low toxicities, under the dosages of 5 g/kg body weights and 10 g/kg body weights, within a continuous observation of two weeks, no death in the subjected mice were observed and no other abnormal expressions were found.

In Ames test of the subjected compound 149, the negative results was obtained which shows no mutagenesis.

EXAMPLES

The various starting materials of the examples can be prepared via the ordinary method of the field or the methods commonly known by the skilled artisans, which can be prepared via e.g. the following reaction routes.

(1) 3-ethoxycarbonyl-7-hydroxycoumarin and 3-carboxy-7-methoxycoumarin

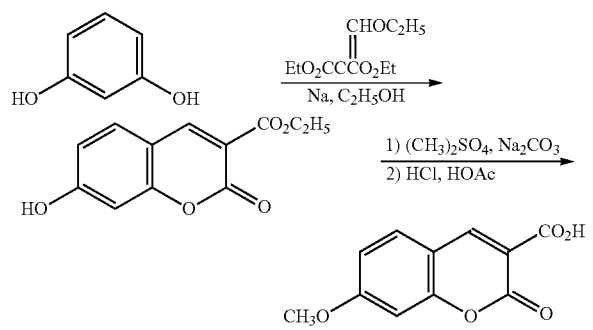

(2) 3-ethoxycarbonyl-6-chloro-7-hydroxycoumarin and 3-carboxy-6-chloro-7-methoxycoumarin

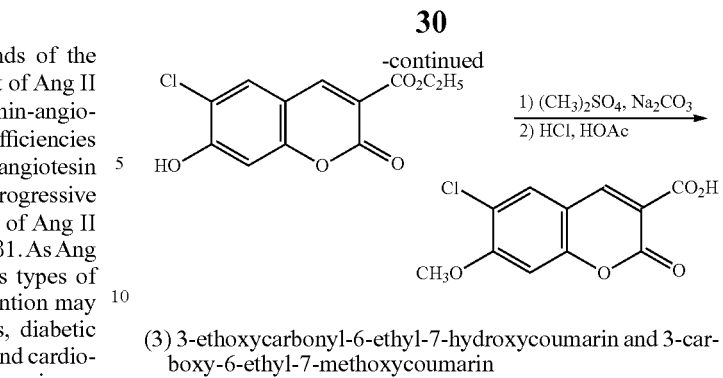

(3) 3-ethoxycarbonyl-6-ethyl-7-hydroxycoumarin and 3-carboxy-6-ethyl-7-methoxycoumarin

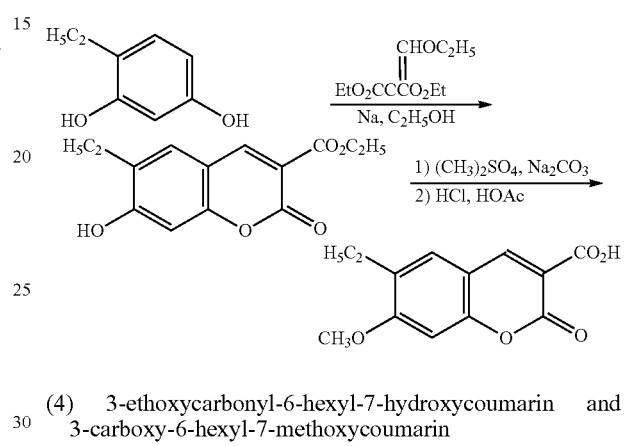

(4) 3-ethoxycarbonyl-6-hexyl-7-hydroxycoumarin and 3-carboxy-6-hexyl-7-methoxycoumarin

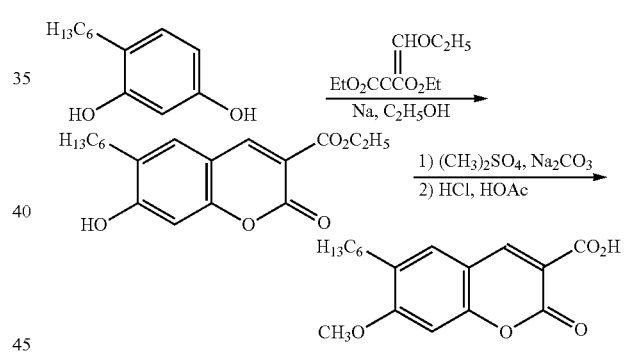

(5) 3-ethoxycarbonyl-6-bromo-7-hydroxycoumarin and 3-carboxy-6-bromo-7-methoxycoumarin

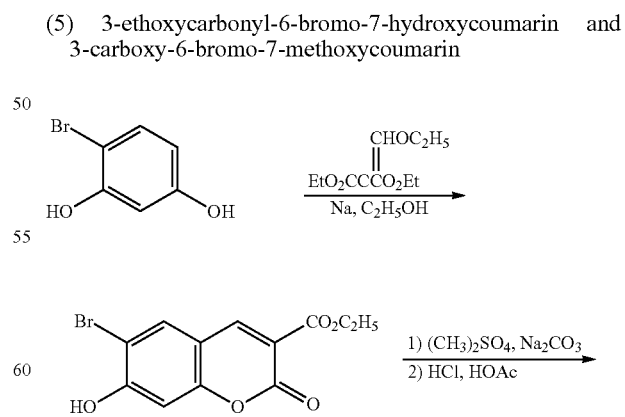

(6) 3-ethoxycarbonyl-7,8-dihydroxycoumarin and 3-carboxy-7,8-dimethoxycoumarin

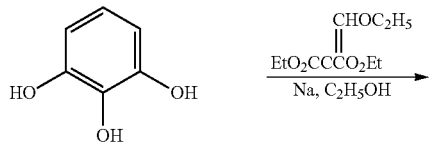

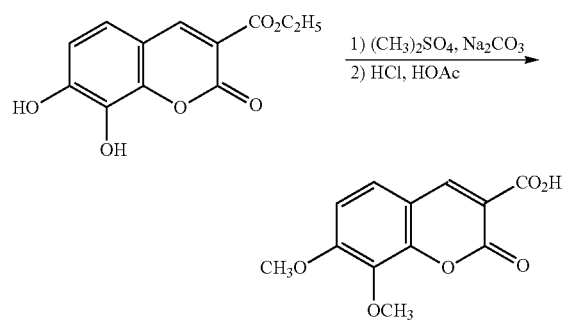

(7) 3-ethoxycarbonyl-7-hydroxy-8-methylcoumarin and 3-carboxy-7-methoxy-8-methylcoumarin

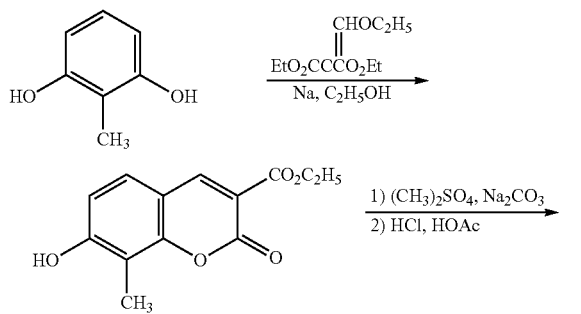

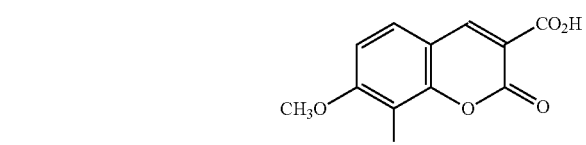

(8) 3-ethoxycarbonyl-7-hydroxy-5-methylcoumarin and 3-carboxy-7-methoxy-5-methylcoumarin

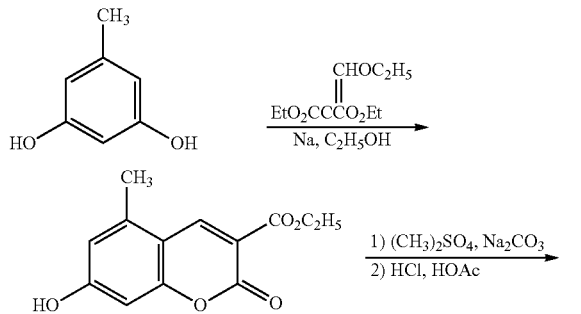

-continued

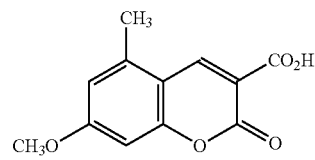

(9) 3-ethoxycarbonyl-6-nitro-7-hydroxy-8-methylcoumarin and 3-carboxy-6-nitro-7-methoxy-8-methylcoumarin

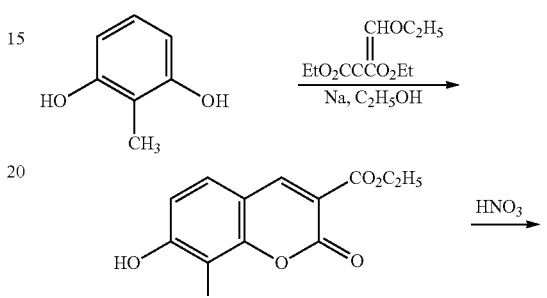

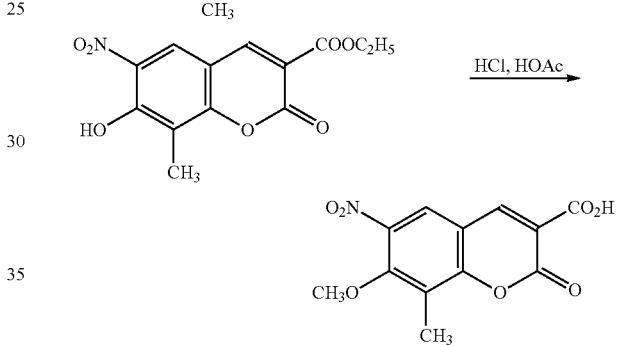

(10) 3-ethoxycarbonyl-6-nitro-7,8-dihydroxycoumarin and 3-carboxy-6-nitro-7,8-dimethoxycoumarin

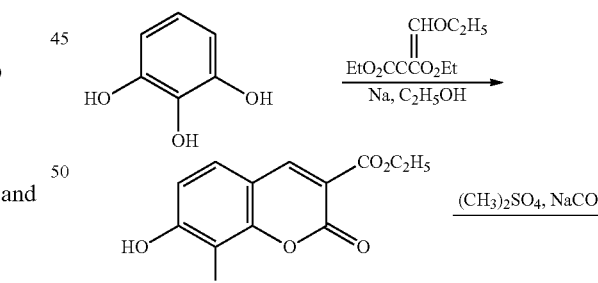

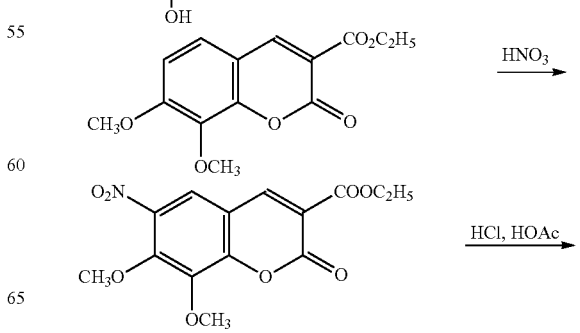

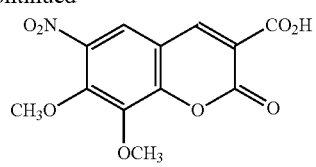

(11) 3-ethoxycarbonyl-5-methyl-6,8-dinitro-7-hydroxycoumarin and 3-carboxy-5-methyl-6,8-dinitro-7-hydroxycoumarin

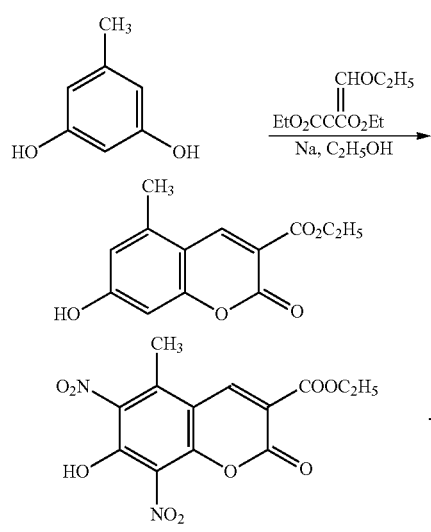

(12) 3-ethoxycarbonyl-5-methyl-6,8-dinitro-7-methoxycoumarin and 3-carboxy-5-methyl-6,8-dinitro-7-methoxycoumarin

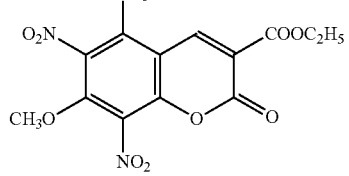

(13) 3-ethoxycarbonyl-5-methyl-6,8-dinitro-7-hydroxycoumarin and 3-carboxy-5-methyl-6,8-dinitro-7-hydroxycoumarin

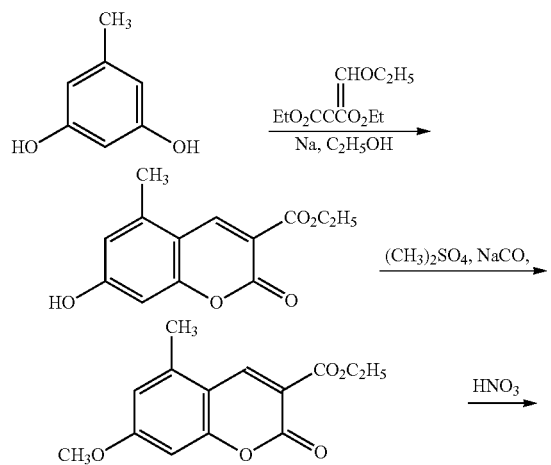

(14) 3-ethoxycarbonyl-6-ethyl-7-hydroxy-8-nitrocoumarin and 3-carboxy-6-ethyl-7-hydroxy-8-nitrocoumarin

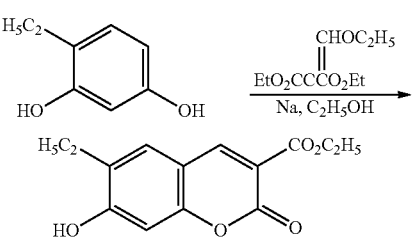

-continued

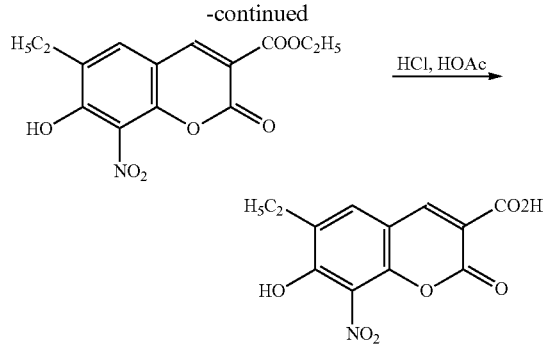

(15) 3-ethoxycarbonyl-6-chloro-7-hydroxy-8-nitrocoumarin and 3-carboxy-6-chloro-7-hydroxy-8-nitrocoumarin

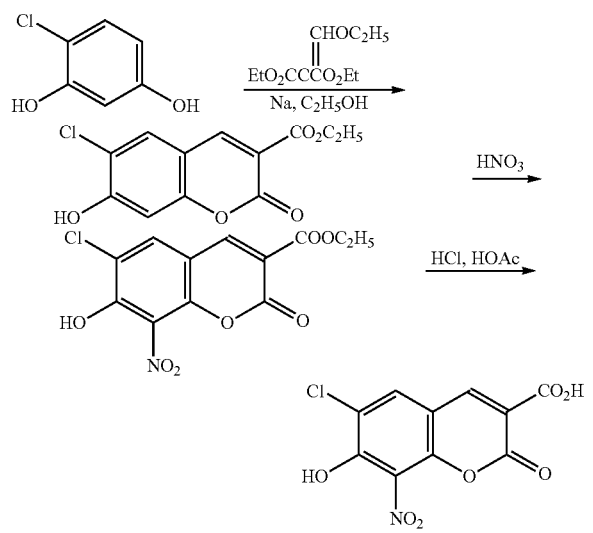

(16) 6-carboxycoumarin

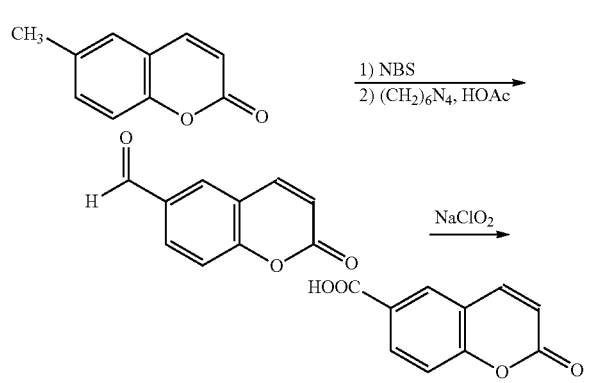

(17) 4-carboxy-7-methylcoumarin

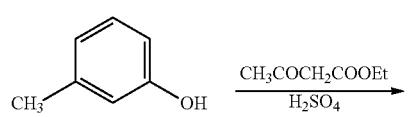

-continued

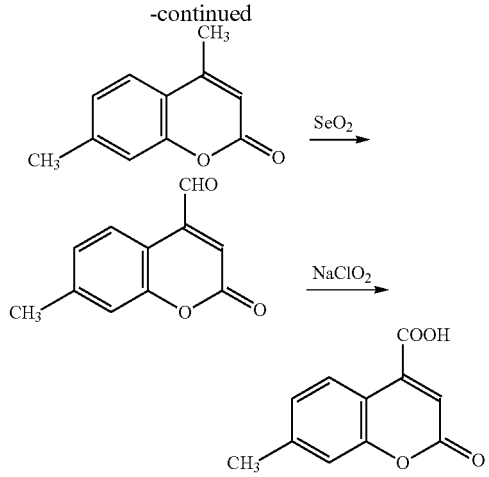

(18) 4-methyl-7-carboxymethoxycoumarin

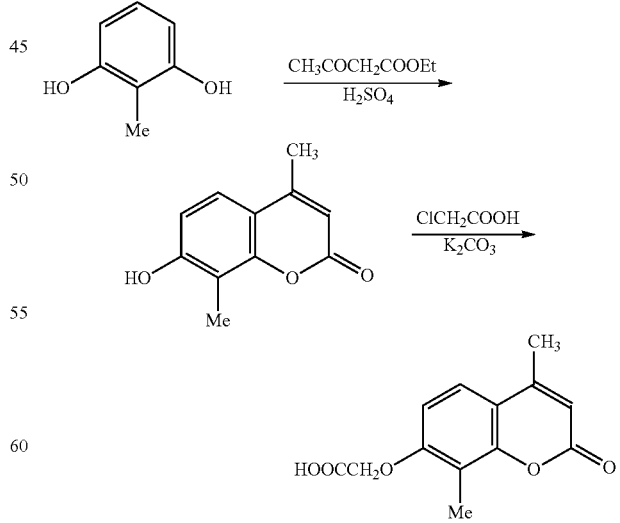

(19) 4,8-dimethyl-7-carboxymethoxycoumarin

The following examples are intended to illustrate this invention, however these examples shall not be construed to limit the scope of the invention.

Example 1

Synthesis of 3-ethoxycarbonyl-6-chloro-7-hydroxy-8-nitro-coumarin (241)

2.75 g (10.2 mmol) of 3-ethoxycarbonyl-6-chloro-7-hydroxycoumarin was added into 10 ml of concentrated sulfuric acid, 1.74 g (20.4 mmol) of concentrated nitric acid was added in portions under the cooling of ice-salt bath, the reaction was monitored through thin-layer chromatography to confirm the completion, and ice was added to seize the reaction. The reaction mixture was then filtered and washed by water, dried to give 1.52 g of the title compound (241).

$^1$H-NMR 300 MHz (DMSO): 1.266 (t, 3H, $CH_3$), 4.232 (q, 2H, $CH_2$), 8.017 (s, 1H, 5-H), 8.593 (s, 1H, 4-H)

Compounds 229-246 in the tables were prepared following the same procedure.

Example 2

Synthesis of 3-ethoxycarbonyl-6-ethyl-7-hydroxy-8-nitro-coumarin (233)

Compound 233 was prepared following the preparation of compound 241, except that 3-ethoxycarbonyl-6-ethyl-7-hydroxy-coumarin was nitrated to give the title compound 233.

$^1$H-NMR 300 MHz (DMSO): 1.262 (t, 3H, 6-ethyl-$CH_3$), 1.401 (t, 3H, ester-$CH_3$), 2.753 (q, 2H, 6-ethyl-$CH_2$), 3.988 (s, 3H, 7-$OCH_3$), 4.408 (q, 2H, ester-$CH_2$), 7.527 (s, 1H, 5-H), 8.479 (s, 1H, 4-H)

Example 3

Synthesis of 3-ethoxycarbonyl-6-nitro-7,8-dimethoxy-coumarin (227)

Compound 227 was prepared following the preparation of compound 241, except that 3-ethoxycarbonyl-7,8-dimethoxycoumarin was nitrated to give the title compound 227.

$^1$H-NMR 300 MHz (DMSO): 1.397 (t, 3H, ester-$CH_3$), 4.063-4.118 (d, 6H, 7,8-$OCH_3$), 4.423 (q, 2H, ester-$CH_2$), 7.757 (s, 1H, 5-H), 9.252 (s, 1H, 4-H)

Example 4

Synthesis of 3-ethoxycarbonyl-6,8-dinitro-7-methoxy-coumarin (239)

Compound was prepared following the preparation of compound 241, except that 3-ethoxycarbonyl-7-methoxy-coumarin was bis-nitrated to give the title compound 239.

$^1$H-NMR 300 MHz (DMSO): 1.290 (t, 3H, ester-$CH_3$), 4.011 (s, 3H, 7-$OCH_3$), 4.292 (q, 2H, ester-$CH_2$), 8.873 (s, 1H, 4-H), 8.955 (s, 1H, 5-H)

Example 5

Synthesis of 3-ethoxycarbonyl-6,8-dinitro-7-hydroxy-coumarin (237)

Compound 237 was prepared following the preparation of compound 241, except that 3-ethoxycarbonyl-7-hydroxy-coumarin was bis-nitrated to give the title compound 237.

$^1$H-NMR 300 MHz (DMSO): 1.237 (t, 3H, ester-$CH_3$), 4.196 (q, 2H, ester-$CH_2$), 8.399 (s, 1H, 4-H), 8.636 (s, 1H, 5-H)

Example 6

Synthesis of 3-(3'-hydroxy-4'-carboxy-phenylamidocarbonyl)-6-ethyl-7-methoxy-coumarin (26)

248 mg (1 mmol) of 3-carboxy-6-ethyl-7-methoxycoumarin and 2 ml of $SOCl_2$ was heated to complete the reaction. After that, $SOCl_2$ was removed and 153 mg (1 mmol) of 4-aminosalicylic acid and 2 ml of pyridine was added. The mixture was heated to complete the reaction. The crude product was purified with DMSO to give 140 mg of the title compound (26).

$^1$H-NMR 300 MHz (DMSO): 1.142 (t, 3H, $CH_3$), 2.569 (q, 2H, $CH_2$), 3.906 (s, 3H, 7-$OCH_3$), 7.069 (d, 1H, 6'-H), 7.098 (s, 1H, 8-H), 7.509 (s, 1H, 2'-H), 7.758 (d, 1H, 5-H), 8.856 (s, 1H, 4-H), 10.848 (s, 1H, CONH), 11.399 (s, 1H, OH) Compounds 1-109, 204-206, 208, 209, 213, 214, 217, 218, 220, 222-228 in table 1 and compounds 247-249 were prepared following the same procedure.

Example 7

Synthesis of 3-(3'-carboxy-4'-hydroxy-phenylamidocarbonyl)-6-ethyl-7-methoxy-coumarin (27)

Compound 27 was prepared following the preparation of compound 26, except that 4-aminosalicylic acid was replaced by 5-amino-salicylic acid to give the title compound 27.

$^1$H-NMR 500 MHz (DMSO): 1.162 (t, 3H, ethyl-$CH_3$), 2.602 (q, 2H, ethyl-$CH_2$), 3.937 (s, 3H, 7-$OCH_3$), 6.786 (d, 1H, 5'-H), 7.178 (s, 1H, 6-H), 7.746 (d, 1H, 6'-H), 7.770 (s, 1H, 5-H), 8.239 (s, 1H, 2'-H), 8.834 (s, 1H, 4-H), 10.583 (s, 1H, CONH)

Element analysis for: $C_{20}H_{17}NO_7$ Calculated (%): C, 62.66; H, 4.47; N, 3.65. Found (%): C, 62.87; H, 4.49; N, 3.71.

Example 8

Synthesis of 3-(m-carboxyphenylamidocarbonyl)-7-methoxycoumarin (2)

Compound 2 was prepared following the preparation of compound 26, except that 3-carboxy-7-methoxy-coumarin reacted with m-aminobenzoic acid to give the title compound 2.

Element analysis for: $C_{18}H_{13}NO_6 \cdot \frac{1}{2}H_2O$ Calculated (%): C, 62.07; H, 4.05; N, 4.02. Found (%): C, 62.72; H, 3.74; N, 4.55.

Example 9

Synthesis of 3-(3'-hydroxy-4'-carboxyphenylamidocarbonyl)-7-methoxy coumarin (7)

Compound 7 was prepared following the preparation of compound 26, except that 3-carboxy-7-methoxy-coumarin reacted with 4-amino-salicylic acid to give the title compound 7.

$^1$H-NMR 300 MHz (DMSO): 3.91 (s, 3H, 7-$OCH_3$), 7.08 (d, 1H, 6-H), 7.11 (s, 1H, 6'-H), 7.53 (s, 1H, 2'-H), 7.77 (d, 1H, 5-11), 7.95 (d, 1H, 5'-H), 8.91 (s, 1H, 4-H), 10.83 (s, 1H, CONH), 11.40 (br, 1H, OH)

Element analysis for: $C_{18}H_{13}NO_7$ Calculated (%): C, 60.85; H, 3.69; N, 3.94. Found (%): C, 60.52; H, 3.59; N, 4.10.

Example 10

Synthesis of 3-(3'-carboxy-4'-hydroxyphenylamidocarbonyl)-7-methoxy coumarin (8)

Compound 8 was prepared following the preparation of compound 26, except that 3-carboxy-7-methoxy-coumarin reacted with 5-amino-salicylic acid to give the title compound 8.

$^1$H-NMR 300 MHz (DMSO): 3.906 (s, 3H, 7-OCH$_3$), 6.964 (d, 1H, 5'-H), 7.037 (d, 1H, 6-H), 7.083 (s, 1H, 8-H), 7.745 (d, 1H, 6'-H), 8.001 (d, 1H, 5-H), 8.234 (s, 1H, 2'-H), 8.877 (s, 1H, 4-H), 10.547 (s, 1H, CONH), 11.103 (br, OH)

Element analysis for: $C_{18}H_{13}NO_7$ Calculated (%): C, 60.85; H, 3.69; N, 3.94. Found (%): C, 60.50; H, 3.62; N, 3.64.

Example 11

Synthesis of 3-[4'-(5"-methylisooxazol-3"-yl)-amidosulfonyl]phenylamido carbonyl]-7-methoxy-coumarin (19)

Compound 19 was prepared following the preparation of compound 26, except that 3-carboxy-7-methoxy-coumarin reacted with sulfamethoxazole (SMZ) to give the title compound 19.

Element analysis for: $C_{21}H_{17}N_3O_7S \cdot \frac{1}{2}H_2O$ Calculated (%): C, 54.31; H, 3.91; N, 9.05. Found (%): C, 54.56; H, 3.49; N, 8.90.

Example 12

Synthesis of 3-(3'-carboxypropylamidocarbonyl)-7-methoxycoumarin (203)

Compound 203 was prepared following the preparation of compound except that 3-carboxy-7-methoxy-coumarin reacted with γ-amino-butyric acid to give the title compound 203.

$^1$H-NMR 300 MHz (DMSO): 1.719 (t, 2H, 3'-CH$_2$), 2.235 (t, 2H, 2'-CH$_2$), 3.311 (t, 2H, 4'-CH$_2$), 3.861 (s, 3H, 7-OCH$_3$), 7.001 (d, 1H, 6-H), 7.074 (s, 1H, 8-H), 7.861 (d, 1H, 5-H), 8.771 (s, 1H, 4-H)

Element analysis for: $C_{15}H_{15}NO_6$ Calculated (%): C, 59.01; H, 4.95; N, 4.59. Found (%): C, 59.05; H, 4.60; N, 4.73.

Example 13

Synthesis of 3-[4'-(5"-methylisooxazol-3")-amidosulfonyl]phenylamido carbonyl]-7-methoxy-8-methylcoumarin (55)

Compound 55 was prepared following the preparation of compound 26 except that 3-carboxy-7-methoxy-8-methyl-coumarin reacted with SMZ to give the title compound 55.

Element analysis for: $C_{22}H_{19}N_3O_7S$ Calculated (%): C, 56.28; H, 4.08; N, 8.95. Found (%): C, 56.61; H, 4.06; N, 9.01.

Example 14

Synthesis of 3-(m-carboxymethylenoxy-phenylamidocarbonyl)-7,8-dimethoxycoumarin (64)

Compound 64 was prepared following the preparation of compound 26 except that 3-carboxy-7,8-dimethoxy-coumarin reacted with m-carboxy methylenoxyaniline to give the title compound 64.

$^1$H-NMR 300 MHz (DMSO): 3.852 (s, 3H, 8-OCH$_3$), 3.951 (s, 3H, 7-OCH$_3$), 4.641 (s, 2H, OCH$_2$), 6.676 (q, 1H, 5'-H), 7.198-7.420 (m, 3H, 4', 6', 6-H), 7.502 (s, 1H, 2'-H), 7.751 (d, 1H, 5-H), 8.853 (s, 1H, 4-H), 10.584 (s, 1H, CONH)

Element analysis for: $C_{20}H_{17}NO_8$ Calculated (%): C, 60.15; H, 4.29; N, 3.51. Found (%): C, 60.41; H, 4.65; N, 3.75.

Example 15

Synthesis of 3-(4'-guanidinosulfonylphenylamidocarbonyl)-7,8-dimethoxy-coumarin (66)

Compound 66 was prepared following the preparation of compound 26 except that 3-carboxy-7,8-dimethoxy-coumarin reacted with sulfaguanidine (SG) to give the title compound 66.

Element analysis for: $C_{19}H_{18}N_4O_7S \cdot 2H_2O$ Calculated (%): C, 47.30; H, 4.56; N, 11.61. Found (%): C, 47.34; H, 4.08; N, 11.00.

Example 16

Synthesis of 3-(3'-carboxy-4'-hydroxy-phenylamidocarbonyl)-7,8-dimethoxy-coumarin (60)

Compound 60 was prepared following the preparation of compound 26 except that 3-carboxy-7,8-dimethoxy-coumarin reacted with 5-amino-salicylic acid to give the title compound 60.

$^1$H-NMR 300 MHz (DMSO): 3.849-3.947 (d, 6H, 7,8-bis-OCH$_3$), 6.962 (d, 1H, 5'-H), 7.233 (d, 1H, 6-H), 7.727-7.755 (d, 2H, 5,6'-H), 8.210 (s, 1H, 2'-H), 8.813 (s, 1H, 4-H), 10.495 (s, 1H, CONH)

Element analysis for: $C_{19}H_{15}NO_8 \cdot \frac{1}{4}H_2O$ Calculated (%): C, 58.61; H, 4.01; N, 3.59. Found (%): C, 58.27; H, 3.86; N, 3.92.

Example 17

Synthesis of 3-(benzoylhydrazinocarbonyl)-5-methyl-7-methoxycoumarin (210)

Compound 210 was prepared following the preparation of compound 26 except that 3-carboxy-5-methyl-7-methoxy-coumarin reacted with benzoyl hydrazine to give the title compound 210.

$^1$H-NMR 300 MHz (DMSO): 2.482 (s, 3H, 5-CH$_3$), 3.888 (s, 3H, 7-OCH$_3$), 6.979 (d, 2H, 6, 8-H), 7.477-7.583 (q, 2H,

3',5'-H), 7.500 (t, 1H, 5'-H), 7.889 (d, 2H, 2',6'-H), 8.792 (s, 1H, 4-H), 10.24 (s, 1H, CON), 10.868 (s, 1H, CONH)

Example 18

Synthesis of 3-(isonicotinoylhydrazinocarbonyl)-5-methyl-7-methoxy coumarin (213)

Compound 213 was prepared following the preparation of compound 26 except that 3-carboxy-5-methyl-7-methoxy-coumarin reacted with isoniazid to give the title compound 213.

$^1$H-NMR 300 MHz (DMSO): 2.553 (s, 3H, 5-CH$_3$), 3.878 (s, 3H, 7-OCH$_3$), 6.979 (d, 2H, 6, 8-H), 7.935 (d, 2H, 3',5'-H), 8.781 (s, 1H, 4-He, 10.545 (s, 1H, CONH), 11.362 (s, 1H, CONH)

Example 19

Synthesis of 3-(3'-carboxy-4'-hydroxy-phenylamidocarbonyl)-5-methyl-7-methoxycoumarin (74)

Compound 74 was prepared following the preparation of compound 26 except that 3-carboxy-5methyl-7-methoxy-coumarin reacted with 5-amino-salicylic acid to give the title compound 74.

Element analysis for: C$_{19}$H$_{15}$NO$_7$Calculated (%): C, 61.79; H, 4.09; N, 3.79. Found (%): C, 61.57; H, 4.07; N, 3.81.

Example 20

Synthesis of 3-(3'-hydroxy-4'-carboxy-phenylamidocarbonyl)-6-chloro-7-methoxy-coumarin (87)

Compound 87 was prepared following the preparation of compound 26 except that 3-carboxy-6-chloro-7-methoxy-coumarin reacted with 4-amino-salicylic acid to give the title compound 87.

$^1$H-NMR 300 MHz (DMSO): 3.996 (s, 3H, 7-OCH$_3$), 7.114 (d, 1H, 6'-H), 7.376 (s, 1H, 8-H), 7.485 (s, 1H, 2'-H), 7.768 (d, 1H, 5'-H), 8.146 (s, 1H, 5-H), 8.839 (s, 1H, 4-H), 10.721 (s, 1H, CONH)

Element analysis for: C$_{18}$H$_{12}$ClNO$_7$Calculated (%): C, 55.47; H, 3.11; N, 3.59. Found (%): C, 55.97; H, 3.13; N, 4.48.

Example 21

Synthesis of 3-(3'-carboxy-4'-hydroxy-phenylamidocarbonyl)-6-chloro-7-methoxy-coumarin (88)

Compound 88 was prepared following the preparation of compound 26 except that 3-carboxy-6-chloro-7-methoxy-coumarin reacted with 5-amino-salicylic acid to give the title compound 88.

$^1$H-NMR 300 MHz (DMSO): 4.010 (s, 3H, 7-OCH$_3$), 6.968 (d, 1H, 5'-H), 7.380 (s, 1H, 8-H), 7.752 (d, 1H, 6'-H), 8.153 (s, 1H, 5-H), 8.211 (s, 1H, 2'-H), 8.817 (s, 1H, 4-H), 10.475 (s, 1H, CONH)

Element analysis for: C$_{18}$H$_{12}$ClNO$_7$Calculated (%): C, 55.47; H, 3.11; N, 3.59. Found (%): C, 55.60; H, 3.18; N, 4.1.

Example 22

Synthesis of 3-(3'-hydroxy-4'-carboxy-phenylamidocarbonyl)-6-bromo-7-methoxy-coumarin (96)

Compound 96 was prepared following the preparation of compound 26 except that 3-carboxy-6-bromo-7-methoxy-coumarin reacted with 4-amino-salicylic acid to give the title compound 96.

$^1$H-NMR 300 MHz (DMSO): 3.996 (s, 3H, 7-OCH$_3$), 7.118 (d, 1H, 6'-H), 7.343 (s, 1H, 8-H), 7.496 (s, 1H, 2'-H), 7.774 (d, 1H, 5'-H), 8.306 (s, 1H, 5-H), 8.846 (s, 1H, 4-H), 10.722 (s, 1H, CONH)

Example 23

Synthesis of 3-(4'-guanidinosulfonylphenylamidocarbonyl)-6-ethyl-7-methoxy-coumarin (32)

Compound 32 was prepared following the preparation of compound 26 except that 3-carboxy-6-ethyl-7-methoxy-coumarin reacted with SG to give the title compound 32.

$^1$H-NMR 300 MHz (DMSO): 1.148 (t, 3H, ethyl-CH$_3$), 2.572 (q, 2H, ethy-CH$_2$), 3.896 (s, 3H, OCH$_3$), 6.690 (br, 4H, guanidino-H), 7.125 (s, 1H, 8-H), 7.709 (s, 1H, 5-H), 7.739 (q, 4H, Ar—H), 8.827 (s, 1H, 4-H), 10.841 (s, 1H, CONH)

Element analysis for: C$_{20}$H$_{20}$N$_4$O$_6$S.¼H$_2$O Calculated (%): C, 53.55; H, 4.60; N, 12.48. Found (%): C, 53.49; H, 4.63; N, 12.40.

Example 24

Synthesis of 3-(4'-guanidinosulfonylphenylamidocarbonyl)-6-chloro-7-methoxy-coumarin (92)

Compound 92 was prepared following the preparation of compound 26 except that 3-carboxy-6-chloro-7-methoxy-coumarin reacted with SG to give the title compound 92.

$^1$H-NMR 300 MHz (DMSO): 3.999 (s, 3H, 7-OCH$_3$), 7.407 (s, 1H, 8-H), 7.776 (q, 4H, Ar—H), 8.172 (s, 1H, 5-H), 8.860 (s, 1H, 4-H), 10.787 (s, 1H, CONH)

Element analysis for: C$_{18}$H$_{15}$ClN$_4$O$_6$S Calculated (%): C, 47.95; H, 3.35; N, 12.43. Found (%): C, 47.54; H, 3.45; N, 12.15.

Example 25

Synthesis of 3-(3'-hydroxy-4'-carboxy-phenylamidocarbonyl)-7-methoxy-8-methyl-coumarin (43)

Compound 43 was prepared following the preparation of compound 26 except that 3-carboxy-7-methoxy-8-methyl-coumarin reacted with 4-amino-salicylic acid to give the title compound 43.

$^1$H-NMR 300 MHz (DMSO): 2.215 (s, 3H, 8-CH$_3$), 3.912 (s, 3H, 7-OCH$_3$), 7.081 (d, 1H, 6'-H), 7.182 (d, 1H, 6-H), 7.612 (s, 1H, 2'-H), 7.747 (d, 1H, 5-H), 7.872 (d, 1H, 5'-H), 8.834 (s, 1H, 4-H), 10.813 (s, 1H, CONH)

Example 26

Synthesis of 3-(3'-carboxy-4'-hydroxy-phenylamidocarbonyl)-7-methoxy-8-methyl-coumarin (44)

Compound 44 was prepared following the preparation of compound 26 except that 3-carboxy-7-methoxy-8-methyl-coumarin reacted with 5-amino-salicylic acid to give the title compound 44

$^1$H-NMR 300 MHz (DMSO): 2.209 (s, 3H, 8-CH$_3$), 3.753 (s, 3H, 7-OCH$_3$), 6.959 (d, 1H, 5'-H), 7.168 (d, 1H, 6-H), 7.723 (d, 1H, 6'-H), 7.848 (d, 1H, 5-H), 8.197 (s, 1H, 2'-H), 8.794 (s, 1H, 4-H), 10.504 (s, 1H, CONH)

Element analysis for: $C_{19}H_{15}NO_7 \cdot \frac{1}{2}H_2O$ Calculated (%): C, 60.32; H, 4.26; N, 3.70. Found (%): C, 59.66; H, 3.92; N, 3.81.

Example 27

Synthesis of 3-(4'-methoxy-phenylamidocarbonyl)-6-nitro-7-hydroxy-8-methyl-coumarin (146)

160 mg (0.604 mmol) of 3-carboxy-6-nitro-7-methoxy-8-methyl-coumarin and 2 ml of thionyl chloride was heated to complete the reaction. Extra thionyl chloride was removed and 74.3 mg (0.604 mmol) of p-anisidine, 1 ml of pyridine and 1 ml of DMF were added therein and the so-obtained mixture was heated to complete the reaction. The reaction mixture was then filtered and washed by water, diluted hydro chloride, water and ethanol, respectively, dried and purified with glacial acetic acid to give 170 mg of the title compound (146).

$^1$H-NMR 300 MHz (DMSO): 2.280 (s, 3H, Ar—CH$_3$), 3.740 (s, 3H, OCH$_3$), 6.941 (d, 2H, 3',5'-H), 7.621 (d, 2H, 2',6'-H), 8.673 (s, 1H, 5-H), 8.897 (s, 1H, 4-H), 10.374 (s, 1H, CONH)

Compounds 110-203, 225-228 were prepared following the same procedure.

Example 28

Synthesis of 3-(4'-guanidinosulfonylphenylamidocarbonyl)-6-nitro-7-methoxy-8-methyl-coumarin (169)

Compound 169 was prepared following the preparation of compound 146 except that 3-carboxy-6-nitro-7-methoxy-8-methylcoumarin reacted with SG, and purified with DMF to give the title compound 169.

$^1$H-NMR 300 MHz (DMSO): 2.382 (s, 3H, 8-CH$_3$), 3.940 (s, 3H, 7-OCH$_3$), 6.677 (br, 4H, guanidino-H), 7.790 (q, 4H, Ar—H), 8.593 (s, 1H, 5-H), 8.903 (s, 1H, 4-H), 10.707 (s, 1H, CONH)

Element analysis for: $C_{19}H_{17}N_5O_8S \cdot \frac{1}{2}H_2O$ Calculated (%): C, 47.10; H, 3.75; N, 14.46. Found (%): C, 47.27; H, 3.73; N, 14.58.

Example 29

Synthesis of 3-(4'-carboxy-phenylamidocarbonyl)-6-nitro-7,8-dimethoxy coumarin (110)

Compound 110 was prepared following the preparation of compound 146 except that 3-carboxy-6-nitro-7,8-methoxy-coumarin reacted with p-amino-benzoic acid to give the title-compound 110.

$^1$H-NMR 300 MHz (DMSO): 3.99-4.06 (q, 6H, 7,8-bis-OCH$_3$), 7.82 (d, 2H, J=8.7, Ar—H), 7.9 (d, 2H, J=8.7, Ar—H), 8.15 (s, 1H, 5-H), 9.09 (s, 4-H) 10.91 (s, 1H, CONH)

Example 30

Synthesis of 3-(3'-carboxy-phenylamidocarbonyl)-6-nitro-7,8-dimethoxy-coumarin (111)

Compound 111 was prepared following the preparation of compound 146 except that 3-carboxy-6-nitro-7,8-dimethoxycoumarin reacted with m-amino-benzoic acid to give the title compound 111.

$^1$H-NMR 300 MHz (DMSO): 3.97-4.05 (q, 6H, 7,8-bis-OCH$_3$), 7.49 (t, 1H, 5'-H), 7.67 (d, 1H, 6'-H), 7.76 (d, 1H, 4'H), 7.93 (s, 1H, 2'-H), 8.32 (s, 1H, 5-H), 9.08 (s, 1H, 4-H), 10.66 (s, 1H, CONH)

Example 31

Synthesis of 3-[4'-(5",6"-dimethoxypyrimidine-4")-amidosulfonyl phenylamidocarbonyl]-6-nitro-7,8-dimethoxycoumarin (123)

Compound 123 was prepared following the preparation of compound 146 except that 3-carboxy-6-nitro-7,8-methoxy-coumarin reacted with sulfadoxine (SDM) to give the title compound 123.

$^1$H-NMR 300 MHz (DMSO): 3.694 (s, 3H, pyrimidine-OCH$_3$), 3.894 (s, 3H, 8-OCH$_3$), 4.064 (s, 3H, 7-OCH$_3$), 7.886-7.996 (q, 4H, Ar—H), 7.974 (s, 1H, 2"-H), 8.109 (s, 1H, 5-H), 9.092 (s, 1H, 4-H), 10.791 (s, 1H, CONH), 10.947 (br, 1H, SO$_2$NH)

Example 32

Synthesis of 3-(3'-hydroxy-4'-carboxyphenylamidocarbonyl)-6-nitro-7-hydroxy-8-methyl-coumarin (148)

Compound 148 was prepared following the preparation of compound 146 except that 3-carboxy-6-nitro-7-hydroxy-8-methylcoumarin reacted with 4-aminosalicylic acid to give the title compound 148.

$^1$H-NMR 300 MHz (DMSO): 2.27 (s, 3H, Ar—CH$_3$), 7.11 (dd, 1H, J=7.8 Hz, 1.8 Hz, 6'-H), 7.498 (d, 1H, J=1.8 Hz, 2'-H), 7.775 (d, 1H, J=7.8, 5'-H), 8.65 (s, 1H, 5-H), 8.892 (s, 1H, 4-H), 10.69 (s, 1H, CONH)

Example 33

Synthesis of 3-(3'-carboxy-4'-hydroxy-phenylamidocarbonyl)-6-nitro-7-hydroxy-8-methyl-coumarin (149)

Compound 149 was prepared following the preparation of compound 146 except that 3-carboxy-6-nitro-7-hydroxy-8-methylcoumarin reacted with 5-aminosalicylic acid to give the title compound 149.

$^1$H-NMR 300 MHz (DMSO): 2.268 (s, 3H, Ar—H), 6.971 (d, 1H, J=8.7 Hz, 5'-H), 7.747 (dd, 1H, J=8.7 Hz, 2.7 Hz, 6'-H), 8.208 (d, 1H, J=2.7 Hz, 2'-H), 8.658 (s, 1H, 5-H), 8.867 (s, 1H, 4-H), 10.403 (s, 1H, CONH)

Element analysis for: $C_{18}H_{12}N_2O_9 \cdot \frac{1}{2}H_2O$ Calculated (%): C, 52.83; H, 3.22; N, 6.85. Found (%): 52.92, 3.26, 6.99.

Example 34

Synthesis of 3-[4'-(2''-pyrimidinylamidosulfonyl) phenylamidocarbonyl]-5-methyl-6,8-dinitro-7-hydroy-coumarin (200)

Compound 200 was prepared following the preparation of compound 146 except 3-carboxy-5-methyl-6,8-nitro-7-hydroxycoumarin reacted with sulfadiazine (SD) to give the title compound 200.

$^1$H-NMR 300 MHz (DMSO): 2.291 (s, 3H, 5-CH$_3$), 7.025 (t, 1H, 5''-H), 7.884 (q, 4H, Ar—H), 8.483 (d, 2H, 4'',6''-H), 8.640 (s, 1H, 4-H), 10.705 (s, 1H, CONH)

Example 35

Synthesis of 3-(4'-amidosulfonylphenylamidocarbonyl)-5-methyl-6,8-dinitro-7-hydroxy-coumarin (198)

Compound 198 was prepared following the preparation of compound 146 except that 3-carboxy-5-methyl-6,8-nitro-7-hydroxycoumarin reacted with sulfanilamide to give the title compound 198.

$^1$H-NMR 300 MHz (DMSO): 2.254 (s, 3H, 5-CH$_3$), 7.240 (br, 2H, NH$_2$), 7.788 (q, 4H, Ar—H), 8.666 (s, 1H, 4-H), 10.676 (s, 1H, CONH)

Example 36

Synthesis of 3-(2'-thiazolamidosulfonylphenylamidocarbonyl)-5-methyl-6,8-dinitro-7-hydroxy-coumarin (201)

Compound 201 was prepared following the preparation of compound 146 except that 3-carboxy-5-methyl-6,8-nitro-7-hydroxycoumarin reacted with sulfathiazole (ST) to give the title compound 201.

$^1$H-NMR 300 MHz (DMSO): 2.291 (s, 3H, 5-CH$_3$), 6.802 (d, 1H, thiazole-H), 7.225 (d, 1H, thiazolyl-H), 7.737 (q, 4H, Ar—H), 8.651 (s, 1H, 4-H), 10.667 (s, 1H, CONH)

Example 37

Synthesis of 3-(4'-guanidinosulfonylphenylamidocarbonyl)-5-methyl-6,8-dinitro-7-hydroxy-coumarin (199)

Compound 199 was prepared following the preparation of compound 146 except that 3-carboxy-5-methyl-6,8-dinitro-7-hydroxycoumarin reacted with SG to give the title compound 199.

$^1$H-NMR 300 MHz (DMSO): 2.293 (s, 3H, 5-CH$_3$), 6.685 (br, 4H, guanidino-H), 7.746 (q, 4H, Ar—H), 8.657 (s, 1H, 4-H), 10.647 (s, 1H, CONH)

Example 38

Synthesis of 3-(2'-phenyl-1',3',4'-oxadiazol-5'-yl)-7-methoxy-8-methyl coumarin (216)

295 mg (0.84 mmol) of 3-(benzoylhydrazinocarbonyl)-7-methoxy-8-methylcoumarin reacted with 4.6 ml phosphorus oxychloride at 100° C. for 5 hours, and the reaction mixture was left to be cool and then poured into ice-water, filtrated, washed with water, and dried. 290 mg of the crude product was obtained, and then the crude product was purified with DMF to give 160 mg of the title compound 216.

$^1$H-NMR 300 MHz (DMSO): 2.252 (s, 3H, 8-CH$_3$), 3.968 (s, 3H, 7-OCH$_3$), 7.174 (d, 1H, 6-H), 7.634 (m, 3H, Ar'—H), 7.812 (d, 1H, 5-H), 8.088 (m, 2H, Ar'—H), 8.874 (s, 1H, 4-H)

Compounds 206, 207, 210-212, 215, 216, 219 and 221 in table 2 were prepared following the same procedure.

Example 39

Synthesis of 3-(2'-phenyl-1',3',4'-oxadiazol-5'yl)-7-methoxycoumarin (206)

Compound 206 was prepared following the preparation of compound 216 except that 3-(benzoylhydrazinocarbonyl)-7-methoxycoumarin reacted with phosphorus oxychloride to give the title compound 206.

$^1$H-NMR 300 MHz (DMSO): 3.929 (s, 3H, 7-OCH$_3$), 7.021 (d, 1H, 6-H), 7.085 (s, 1H, 8-H), 7.599-7.668 (m, 3H, Ar—H), 7.871 (d, 1H, 5-H), 8.095 (m, 2H, Ar—H), 8.898 (s, 1H, 4-H)

Element analysis for: $C_{18}H_{12}N_2O_4$ Calculated (%): C, 67.49; H, 3.78; N, 8.75. Found (%): C, 67.57; H, 3.98; N, 8.41.

Example 40

Synthesis of 3-[(2'-pyridyl-4'')-1',3',4'-oxadiazol-5'yl]-6-hexyl-7-methoxy coumarin (221)

Compound 221 was prepared following the preparation of compound 216 except that 3-(isonicotinoylhydrazinocarbonyl)-6-hexyl-7-methoxy coumarin reacted with phosphorus oxychloride to give the title compound 221.

$^1$H-NMR 300 MHz (DMSO): 0.869 (t, 3H, hezyl-CH$_3$), 1.240 (br, 6H, hezyl-CH$_2$), 1.574 (t, 2H, hexyl-CH$_2$), 2.734 (t, 2H, hezyl-CH$_2$), 3.959 (s, 3H, 7-OCH$_3$), 7.116 (s, 1H, 8-H), 7.699 (s, 1H, 5-H), 8.070 (br, 2H, pyridyl-H), 8.920 (br, 2H, pyridyl-H), 8.921 (s, 1H, 4-H)

Element analysis for: $C_{23}H_{23}N_3O_4 \cdot 3H_2O$ Calculated (%): C, 60.12; H, 6.36; N, 9.15. Found (%): C, 59.51; H, 5.51; N, 8.96.

Example 41

Synthesis of 4-methyl-7-(4'-ethoxycarbonylphenylamidocarbonyl-methylenoxy)coumarin (255)

60 mg (0.256 mmol) of 4-methyl-7-carboxy-methylenoxy-coumarin and 2 ml of thionyl chloride was heated to complete the reaction. Extra thionyl chloride was removed and the residue was dissolved in 5 ml of methylene chloride. 44 mg (0.267 mmol) of ethyl 4-amino-benzoate in 5 ml methylene chloride and 3 ml of pyridine were added therein and the reaction mixture was stirred for 0.5 hours to precipitate the solid and the stirration was continued for additional 1 hour. The product was filtrated, washed with methylene chloride, and dried to give 80 mg of the title compound (255).

$^1$H-NMR 300 MHz (DMSO): 1.293 (t, 3H, ester-methyl); 2.389 (s, 3H, 4-methyl); 4.269 (q, 2H, ester-CH$_2$), 4.881 (s, 2H, OCH$_2$), 6.219 (s, 1H, 3-H), 7.018 (d, 1H, 8-H), 7.056 (d, 1H, 6-H), 7.712 (d, 1H, 5-H), 7.760 (d, 2H, 2',6'-H), 7.919 (d, 2H, 3',5'-H), 10.479 (s, 1H, CONH)

Element analysis for: $C_{21}H_{19}NO_6$ Calculated (%): C, 66.13; H, 5.02; N, 3.67. Found (%): C, 66.26; H, 4.91; N, 3.81.

Compounds 250-264 in table 2 were prepared following the same procedure.

Example 42

Synthesis of 4-methyl-7-phenylamidocarbonyl-methylenoxycoumarin (248)

Compound 248 was prepared following the preparation of compound 255 except that ethyl 4-amino-benzoate was replaced by aniline to give the title compound 248.

$^1$H-NMR 300 MHz (DMSO): 2.377 (s, 3H, 4-CH$_3$), 4.825 (s, 2H, 7OCH$_2$), 6.208 (s, 1H, 3-H), 6.997 (m, 3H, 4', 6, 8-H), 7.306 (t, 2H, 3', 5'-H), 7.593 (d, 2H, 2',6'-H), 7.711 (d, 1H, 5-H), 10, 144 (s, CONH)

Element analysis for: C$_{18}$H$_{15}$NO$_4$Calculated (%): C, 69.89; H, 4.89; N, 4.53. Found (%): C, 69.61; H, 4.891; N, 4.58.

Example 43

Synthesis of 4-methyl-7-(4'-carboxyphenylamidocarbonyl-methylenoxy) coumarin (252)

Compound 252 was prepared following the preparation of compound 255 except that ethyl 4-amino-benzoate was replaced by p-amino-benzoic acid to give the title compound 252.

$^1$H-NMR 300 MHz (DMSO): 2.404 (s, 3H, 4-CH$_3$), 4.899 (s, 2H, 7-OCH$_2$), 6.235 (s, 1H, 3-H), 7.036 (s, 1H8-H), 7.073 (d, 1H, 6-H), 7.713 (d, 1H, 5-H), 7.739-7.924 (q, 4H, Ar—H), 10.491 (s, 1H, CONH)

Element analysis for: C$_{19}$H$_{15}$NO$_6$.¼H$_2$O Calculated (%): C, 63.77; H, 4.37; N, 3.92. Found (%): C, 63.76; H, 4.28; N, 4.24.

Example 44

Synthesis of 4-methyl-7-(4'-hydroxyphenylamidocarbonyl-methylenoxy) coumarin (249)

Compound 249 was prepared following the preparation of compound 255 except that ethyl 4-amino-benzoate was replaced by p-amino-phenol to give the title compound 249.

$^1$H-NMR 300 MHz (DMSO): 2.084 (s, 3H, 4-CH$_3$), 4.781 (s, 2H, 7-OCH$_2$), 6.230 (s, 1H, 3-H), 6.705-7.390 (q, 4H, Ar—H), 7.014 (s, 1H, 8-H), 7.060 (d, 1H, 6-H), 7.723 (d, 1H, 5-H), 9.905 (s, 1H, CONH)

Element analysis for: C$_{18}$H$_{15}$NO$_5$Calculated (%): C, 66.45; H, 4.65; N, 4.31. Found (%): C, 66.14; H, 4.62; N, 4.32.

Example 45

Synthesis of 4-methyl-7-(3'-carboxy-4'-hydroxyphenylamidocarbonyl-methylenoxy)coumarin (261)

Compound 261 was prepared following the preparation of compound 255 except that ethyl 4-amino-benzoate was replaced by 5-amino-salicylic acid to give the title compound 261.

$^1$H-NMR 300 MHz (DMSO): 2.495 (s, 3H, 4-CH$_3$), 4.818 (s, 2H, 7-OCH$_2$), 6.233 (s, 1H, 3-H), 6.940 (d, 1H, 6-H), 7.052 (s, 1H, 8-H), 7.077 (d, 1H, 5'-H),

Element analysis for: C$_{19}$H$_{15}$NO$_7$ Calculated (%): C, 61.79; H, 4.09; N, 3.79. Found (%): C, 61.49; H, 3.96; N, 3.86.

Example 46

Synthesis of 4-methyl-7-(3'-trifluoromethylphenylamidocarbonyl-methylenoxy)coumarin (257)

Compound 257 was prepared following the preparation of compound 255 except that ethyl 4-amino-benzoate was replaced by 3-fluoromethyl aniline to give the title compound 257.

$^1$H-NMR 300 MHz (DMSO): 2.389 (s, 3H, 4-CH$_3$), 4.872 (s, 2H, 7-OCH$_2$), 6.220 (s, 1H, 3-H), 7.027-7.075 (m, 2H, 6, 8-H), 7.429 (d, 1H, 6'-H), 7.567 (t, 1H, 5'-H), 7.719 (d, 1H, 5-H), 7.857 (d, 1H, 4'-H), 8.096 (s, 1H, 2'-H), 10.446 (s, 1H, CONH)

Element analysis for: C$_{19}$H$_{14}$F$_3$NO$_4$Calculated (%): C, 60.48; H, 3.74; N, 3.71. Found (%): C, 60.17; H, 3.45; N, 3.79.

Example 47

Synthesis of 4-methyl-7-(3'-trifluoromethyl-4'-nitrophenylamido carbonylmethylenoxy)coumarin (258)

Compound 258 was prepared following the preparation of compound 255 except that ethyl 4-amino-benzoate was replaced by 3-fluoromethyl-4'-nitro-aniline to give the title compound 258.

$^1$H-NMR 300 MHz (DMSO): 2.409 (s, 3H, 4-CH$_3$), 4.955 (s, 2H, 7-OCH$_2$), 6.243 (s, 1H, 3-H), 7.061 (s, 1H, 8-H), 7.086 (d, 1H, 6-H), 7.734 (d, 1H, 5'-H), 8.127 (d, 1H, 6'-H), 8.215 (d, 1H, 5-H), 8.331 (s, 1H, 2'-H), 10.945 (s, 1H, CONH)

Element analysis for: C$_{19}$H$_{13}$F$_3$N$_2$O$_6$.½H$_2$O Calculated (%): C, 52.91; H, 3.27; N, 6.50. Found (%): C, 53.19; H, 3.05; N, 6.76.

Example 48

Synthesis of 4,8-dimethyl-7-(3'-trifluoromethylphenylamidocarbonyl-methylenoxy)coumarin (262)

Compound 262 was prepared following the preparation of compound 255 except that 4,8-dimethyl-7-carboxy-methyl-enoxycoumarin reacted with 3-fluoromethylaniline to give the title compound 262.

$^1$H-NMR 300 MHz (DMSO): 2.291 (s, 3H, 8-CH$_3$), 2.392 (s, 3H, 4-CH$_3$), 4.934 (s, 2H, 7-OCH$_2$), 6.237 (s, 1H, 3-H), 7.002 (d, 1H, 6-H), 7.440 (d, 1H, 6'-H), 7.564 (d, 1H, 5'-H), 7.603 (d, 1H, 5-H), 7.816 (d, 1H, 4'-H), 8.103 (s, 1H, 2'-H), 10.503 (s, 1H, CONH)

Element analysis for: C$_{20}$H$_{16}$F$_3$NO$_4$Calculated (%): C, 61.38; H, 4.12; N, 3.58. Found (%): C, 61.16; H, 4.03; N, 3.67.

Example 49

Synthesis of 4,8-dimethyl-7-(3'-hydroxy-4-carboxyphenylamidocarbonyl methylenoxy)-coumarin (264)

Compound 264 was prepared following the preparation of compound 255 except that 4,8-dimethyl-7-carboxy-methyl-enoxycoumarin reacted with 4-amino-salicylic acid to give the title compound 264.

$^1$H-NMR 300 MHz (DMSO): 2.270 (s, 3H, 8-CH$_3$), 2.371 (s, 3H, 4-CH$_3$), 4.931 (s, 2H, 7-OCH$_2$), 6.215 (s, 1H, 3-H), 6.958 (d, 1H, 6-H), 7.087 (d, 1H, 6'-H), 7.337 (s, 1H, 2'-H), 7.546 (d, 1H, 5'-H), 7.717 (d, 1H, 5-H), 10.455 (s, 1H, CONH)

Element analysis for: $C_{20}H_{17}NO_7$ Calculated (%): C, 62.66; H, 4.47; N, 3.65. Found (%): C, 62.43; H, 4.43; N, 3.88.

Example 50

Synthesis of 6-(4'-ethyloxycarbophenylamidocarbonyl)coumarin (265)

A mixture of 95 mg (0.5 mmol) of 6-carboxycoumarin and phosphorous pentachloride in 50 ml toluene was refluxed for 1 hour and the reaction mixture was concentrated. To the residue obtained, 83 mg (0.5 mmol) of ethyl p-amino benzoate and 1 ml of pyridine were added and the reflux was continued for additional 10 minutes. The reaction mixture was cooled down and acidified with hydrochloric acid to obtain a solid, which was purified with ethanol to give 100 mg of the title compound 265

$^1$H-NMR 300 MHz (DMSO): 1.31 (t, 3H, ester-CH$_3$), 4.28 (q, 2H, ester-CH$_2$), 6.59 (d, 1H, 3-H), 7.55 (d, 1H, 8-H), 7.92 (d, 2H, Ar'—H), 7.96 (d, 2H, Ar'—H), 8.16 (m, 2H, 4, 7-H), 8.34 (d, 1H, 5-H), 10.68 (s, 1H, CONH)

Element analysis for: $C_{19}H_{15}NO_5 \cdot \frac{1}{2}H_2O$ Calculated (%): C, 65.80; H, 4.65; N, 4.04. Found (%): C, 66.07; H, 4.59; N, 4.06.

Compound 266 was prepared following the same procedure.

Pharmacologic Experiments

Example 1

TGF-β-Induced Cell Growth Inhibition of the Test Compounds on Mink Pulmonary Epithelial Cells Mink pulmonary epithelial cells were seeded in 24 well-plate at a density of $3 \times 10^4$ cells/well and cultured in modified Eagle's medium (MEM) containing 10% fetal bovine serum in 37° C. and 5% CO$_2$. Next day the serum was replaced by a MEM containing 0.2% fetal bovine serum. After 24 hours, the medium was replaced with fresh medium containing 10 pmol/L TGF-β and test compounds, and incubated for 24 h. [$^3$H]Thymidine was added to the medium 2 hours before the termination of incubation. After removing the medium, cells were washed with PBS, dissolved in 0.5 mol/L NaOH, and radioactivity was measured. The inhibitory effects of test compounds are represented as the percentage of Thymidine uptake recovery (Table 3).

Tab. 3 TGF-β-Induced Cell Growth Inhibition of Tested Compounds in Mink Lung Epithelial Cells

TABLE 3

TGF-β-induced cell growth inhibition of tested compounds in Mink Lung epithelial cells

| | No. of tested compounds (10 μg/ml) | | | | |
|---|---|---|---|---|---|
| | 26 | 92 | 73 | 7 | 2 |
| Inhibition recovery rate on cell growth(%) | 70.7 | 95.0 | 15.1 | 67.1 | 27.1 |

Example 2

TGF-β Receptor Binding Antagonism Assay of Test Compounds

Balb/c 3T3 cells were seeded in 24 well-plate and cultured in Dulbecco's modified Eagle's medium (DMEM) supplemented with 10% fetal bovine serum, in 37° C. and 5% CO$_2$, for 2-4 days. When cells were at a near-confluent, medium was changed to the binding buffer (50 mmol/L HEPES containing NaCl, KCl, MgSO$_4$ and CaCl$_2$). The assay was initiated by addition of 50 pmol/L [$^{125}$I]TGF-β1 and test compounds. After incubation for 210-240 minutes, the medium was removed, and cells were washed with ice-cold binding buffer. Non-specific bindings in the presence of 10 nmol/L TGF-β1 were determined. The cells were then solubilized using buffer containing Triton X-100 and the radioactivity was measured (see Table 4).

TABLE 4

TGF-β receptor binding antagonism of tested compounds in Balb/c 3T3 cells

| Compounds (10 μg/ml) | Inhibition Rate (%) | IC$_{50}$ (μg/ml) | Compounds (10 μg/ml) | Inhibition Rate (%) | IC$_{50}$ (μg/ml) |
|---|---|---|---|---|---|
| 1 | 32.2 | | 42 | 4.1 | |
| 2 | 74.1 | 13.8 | 49 | 15.5 | |
| 3 | 11.7 | | 55 | 52.3 | |
| 6 | −6.0 | | 66 | 52.3 | |
| 7 | 94.2 | 7.8 | 67 | 16.2 | |
| 9 | 11.4 | | 73 | 60.0 | |
| 12 | 5.1 | | 79 | 16.2 | |
| 14 | 35.9 | | 83 | 21.2 | |
| 21 | 10.1 | | 87 | 91.1 | |
| 22 | 37.4 | | 88 | 111.2 | 5.3 |
| 25 | 11.6 | | 91 | 34.7 | |
| 26 | 95.4 | 8.5 | 92 | 106.4 | |
| 27 | 77.2 | | 93 | 29.7 | |
| 31 | 29.2 | | 96 | 82.3 | |
| 33 | 32.1 | | 104 | 42.8 | |
| 34 | 36.4 | | 206 | −0.7 | |
| 37 | 41.4 | | | | |

Example 3

Protection of Tested Compound Against Chronic Renal Failure Caused by 5/6 Nephrectomy in Rats The model on chronic renal failure induced by partial renal ablation in rats was set up according to the *Guidelines of Pre-clinic Research for New Drugs.*

Male Wistar rats with initial body weights of ~200 g, anesthetized with 35 mg/kg of pentobarbital i.p., the right kidney was removed, and the upper and lower pole parenchymas of the left kidney were resected, stop bleeding, closed the abdominal and sutured. Four weeks following surgery, the BUN, creatinine and urinary protein in rats were determined. Angiotensin II (AII) level was determined using radioimmunoassay and TGF-β1 using ELISA methods. Rats were randomly divided into seven groups, 30/group, with sham, model, Benazepril (4 mg/kg/day) and Losartan (10 mg/kg/day) as positive control, and compound 149 groups (7.5 mg/kg/day, 15 mg/kg/day and 30 mg/kg/day, respectively). All the groups were administered intragastrically, once per day and 6 (six) times per week, till 16 weeks post surgery.

Body weights were weighed to observe the growth of the rats. The above indexes were determined every 4 weeks up to the 16$^{th}$ week following the initiation of drug administration, and at each time, a number of animals were sacrificed and the kidneys were harvested for pathological analysis.

Pathological lesions in chronic renal failure models are mainly glomerulosclerosis and interstitial fibrosis. According to the damage extents, glomerulosclerosis is divided into five grades (0~IV). 0 grade means no glomerulus pathological changes at all, and IV grade means ultimately glomerular sclerosis and glassy pathological changes. 50 glomerulus were observed in each animal kidney tissue slide, and percentage of various grade in each group was calculated based on the above five grades.

4 weeks after nephrectomy, BUN in serum increased by 111.12% (P<0.01), urinary protein concentration increased by 86.13% (P<0.01), and TGF-β1 level increased by 70.84% (P<0.02).

12 weeks after nephrectomy (8 weeks since administration), morphological results demonstrated that the rates of 0 grade glomerylus in residual kidney in 30 mg/kg compound 149 (P<0.05) and Losartan (P<0.05) groups were higher than that of the model group with significant difference. Glomerulus pathological scores were less than that of the model group significantly. The inflammatory cell infiltration existed in some animal kidney tissues of the Benazepril group was severe, and nephrotubular enlargement as well as protein-like substance also appeared.

16 weeks after nephrectomy (12 weeks since administration), pathological results indicated that the number of grade III glomerulus in the 30 mg/kg group of compound 149 and the Losartan group was less than that of the model group significantly (P<0.01 and P<0.05, respectively). The glomerulus pathological score in the positive Benazepril group was the highest, and the inflammatory cell infiltration in kidney matrix was medium-severe, interstitial fibrosis, nephrotubular enlargement as well as protein-like substance existed.

The results are shown in Tables 5A-E.

TABLE 5

Protection of test compound on chronic renal failure induced by 5/6 nephrectomy in rats A. The change of serum creatinine and BUN concentration in $8^{th}$ week after administration (following 12 weeks after nephrectomy)

| Groups | Dose (mg/kg) | Scr. (mg/dL) | Change Rate (%) | BUN (mg/dL) | Change Rate (%) |
|---|---|---|---|---|---|
| Sham | — | 2.08 ± 0.742 | | 13.00 ± 2.326 | 125.90↑ |
| Model | — | 3.06 ± 0.768 | 47.93↑ | 29.37 ± 3.079# | 28.23↑ |
| Benazepril | 4 | 3.54 ± 1.140 | 15.36↑ | 37.66 ± 8.895 | 12.70↓ |
| Losartan | 10 | 2.34 ± 0.268* | 23.46↓ | 25.64 ± 5.116 | 23.89↓ |
| Compound | 7.5 | 2.14 ± 0.500* | 30.26↓ | 22.35 ± 3.120* | 11.33↓ |
| 149 | 15 | 1.80 ± 0.550* | 41.34↓ | 26.04 ± 4.234 | 3.98↑ |
| | 30 | 1.89 ± 0.184 | 38.20↓ | 30.54 ± 11.697 | |

B. The change of serum TGF-β1, Angiotensin II and urinary protein in $8^{th}$ week after administration (following 12 wk after nephrectomy)

| Groups | Dose (mg/kg) | TGF-β1 (ng/ml) | Change (%) | AII (pg/ml) | Change (%) | UP (mg/day) | Change (%) |
|---|---|---|---|---|---|---|---|
| Sham | | 20.1 ± 6.2 | | 54.5 ± 22.7 | 12.7 | 18.3 ± 2.5 | |
| Model | | 46.33 ± 14.74 | 130.5↑ | 94.5 ± 7.4# | 73.4↑ | 40.7 ± 14.2# | 122.5↑ |
| Benazepril | 4 | 40.9 ± 26.6 | 11.72↓ | 74.3 ± 13.2 | 21.4↓ | 51.1 ± 23.6 | 25.8↑ |
| Losartan | 10 | 18.7 ± 9.2 | 59.6↓ | 96.7 ± 32.1 | 2.2↑ | 32.7 ± 10.3 | 19.6↓ |
| Compound | 7.5 | 20.0 ± 6.7 | 56.8↓ | 63.9 ± 13.2* | 32.4↓ | 30.1 ± 16.6 | 26.0↓ |
| 149 | 15 | 18.6 ± 12.2 | 59.9↓ | 49.9 ± 21.3* | 47.2↓ | 30.4 ± 16.2 | 25.3↓ |
| | 30 | 18.9 ± 10.1 | 59.2↓ | 41.0 ± 12.5* | 56.6↓ | 34.3 ± 12.1 | 15.7↓ |

C. The change of serum creatinine (Scr.) and BUN concentration in $12^{th}$ week after administration (following 16 weeks after nephrectomy)

| Groups | Dose (mg/kg) | Scr. (mg/dL) | Change Rate (%) | BUN (mg/dL) | Change Rate (%) |
|---|---|---|---|---|---|
| Sham | — | 2.25 ± 0.39 | | 21.24 ± 3.354 | |
| Model | — | 2.71 ± 0.49# | | 38.93 ± 8.755# | 83.32↑ |
| Benazepril | 4 | 2.28 ± 0.70 | 20.70↑ | 39.48 ± 7.109 | 1.41↑ |
| Losartan | 10 | 2.21 ± 0.48* | | 37.84 ± 5.672 | 2.80↓ |
| Com. 149 | 7.5 | 2.73 ± 0.78 | 19.01↑ | 39.42 ± 4.686 | 1.25↑ |
| | 15 | 2.63 ± 0.38 | | 37.32 ± 5.467 | 4.14↓ |
| | 30 | 2.10 ± 0.71* | 22.73↓ | 36.60 ± 5.422 | 5.99↓ |
| | | | 0.75↓ | | |
| | | | 2.87↓ | | |
| | | | 28.82↓ | | |

D. The change of serum TGF-β1, Angiotensin II and urinary protein in $12^{th}$ week after administration (following 16 wk after nephrectomy)

| Groups | Dose (mg/kg) | TGF-β1 (ng/ml) | Change (%) | AII (pg/ml) | Change (%) | UP (mg/day) | Change (%) |
|---|---|---|---|---|---|---|---|
| Sham | | 18.2 ± 8.9 | | 30.0 ± 7.6 | | 16.5 ± 17.3 | |
| Model | | 12.8 ± 7.9 | | 61.7 ± 24.3 | 105.7↑ | 54.2 ± 26.1# | 228↑ |

TABLE 5-continued

Protection of test compound on chronic renal failure induced by 5/6 nephrectomy in rats

| Benazepril | 4 | 12.8 ± 14.8 | 0.57↑ | 47.8 ± 12.0 | 22.6↓ | 66.3 ± 31.9 | 22.3↑ |
| Losartan. | 10 | 11.8 ± 12.6 | 7.48↓ | 38.9 ± 17.4* | 37.2↑ | 39.3 ± 14.2 | 18.4↓ |
| Com. 149 | 7.5 | 13.6 ± 7.1 | 6.28↑ | 48.3 ± 48.5 | 21.6↓ | 66.7 ± 38.8 | 23.1↑ |
|  | 15 | 12.3 ± 7.7 | 3.91↓ | 41.3 ± 28.4 | 33.0↓ | 52.3 ± 34.4 | 0.06↓ |
|  | 30 | 11.6 ± 6.7 | 9.38↓ | 19.2 ± 9.19* | 68.6↓ | 48.2 ± 31.6 | 11.1↓ |

E. Pathological results

| wk | Groups | Glomerulosclerosis Grade (%) | | | | | Total Grade |
|---|---|---|---|---|---|---|---|
| | | 0 | I | II | III | IV | |
| 8 wk after ad. | Model | 10.0 ± 17.3 | 38.7 ± 21.2 | 31.5 ± 17.3 | 13.6 ± 18.3 | 1.8 ± 3.3 | 4.9 ± 1.5 |
| | Benazepril | 12.2 ± 19.0 | 29.6 ± 23.9 | 28.1 ± 18.1 | 19.6 ± 24.2 | 5.9 ± 11.2 | 5.5 ± 2.6 |
| | Losartan | 54.4 ± 29.2** | 31.9 ± 20.0 | 13.7 ± 14.0 | 1.1 ± 3.3** | 0 | 2.8 ± 1.0** |
| | Com.149 | | | | | | |
| | 30 mg/kg | 28.3 ± 20.8 | 34.2 ± 23.0 | 7.5 ± 8.8* | 17.5 ± 30.7 | 6.7 ± 13.4 | 4.9 ± 3.5 |
| | 15 mg/kg | 37.5 ± 29.3* | 27.5 ± 16.3 | 18.8 ± 9.9 | 13.3 ± 20.7 | 2.9 ± 8.2 | 3.9 ± 1.7* |
| | 7.5 mg/kg | 15.7 ± 19.0 | 24.0 ± 21.1 | 30.0 ± 20.8 | 23.2 ± 28.5 | 8.0 ± 13.0 | 5.7 ± 2.9 |
| 12 wk after ad. | Model | 0 | 3.3 ± 6.4 | 29.0 ± 23.4 | 50.5 ± 18.7 | 17.6 ± 14.1 | 8.5 ± 1.3 |
| | Benazepril | 0 | 0 | 19.1 ± 27.1 | 46.2 ± 15.6 | 34.8 ± 29.9 | 9.8 ± 1.4 |
| | Losartan | 0 | 10.0 ± 2.9 | 45.7 ± 17.7 | 41.9 ± 25.6 | 2.8 ± 4.8 | 7.2 ± 1.3** |
| | Com.149 | | | | | | |
| | 30 mg/kg | 0 | 2.0 ± 4.5 | 71.3 ± 11.5* | 26.7 ± 7.8** | 0 | 6.7 ± 0.2** |
| | 15 mg/kg | 0 | 8.1 ± 14.1 | 38.1 ± 27.4 | 46.2 ± 26.1 | 9.1 ± 12.6 | 7.7 ± 1.7 |
| | 7.5 mg/kg | 0 | 2.3 ± 6.3 | 37.1 ± 16.0 | 51.4 ± 8.6 | 13.8 ± 20.6 | 8.6 ± 1.9 |

Note:
*P < 0.05, compared with the model group;
P < 0.05, compared with the sham group;
↑increase; ↓decrease.
**P < 0.01, compared with the model group.

The above various parameters with compound 149 treatment are all better than those of the Benazepril group and are equivalent to those of the Losartan group. Moreover, pathological results show that the test compound had no significant affection with the major organs such as heart, liver, spleen, and lungs.

Example 4

Inhibition of the Test Compound on Kidney Tubulointerstitial Fibrosis Caused by Unilateral Ureteral Obstructed (UUO) in Rats Male Wistar rats with initial body weights of 180~230 g were used. Unilateral ureteral obstruction was performed under pentobarbital anesthesia (35 mg/kg) and sterile conditions. Via a midline incision, the left ureteral was ligated. Sham surgery was performed by making a midline incision but leaving ureteral intact. Following surgery, rats were randomly divided into sham, model, Benazepril (4 mg/kg/day) and Losartan (10 mg/kg/day) as positive control, and compound 149 (5 mg/kg/day, 10 mg/kg/day and 20 mg/kg/day). Starting 2 day before surgery, Benazepril, Losartan and compound 149 were administered for 16 days orally. BUN and creatinine in serum were determined in the $11^{th}$ and $16^{th}$ day (Table 6) following initiation of Benazepril, Losartan and compound 149 treatment, at which time animals were killed and the kidneys were harvested. Tissues were dissected, weighed, fixed in 10% formaldehyde and embedded in paraffin wax for pathological analysis. The $9^{th}$ day serum BUN and creatinine in model group after surgery increased 78.7% (P<0.01) and 20.73% (P<0.05) respectively.

TABLE 6

Inhibition of test compound on kidney tubulointerstitial fibrosis caused by unilateral ureteral obstruction (UUO) in rats

| Groups | Dose (mg/kg) | Scr. (mg/kg) | Change Rate (%) | BUN (mg/dL) | Change Rate (%) |
|---|---|---|---|---|---|
| Sham | — | 1.45 ± 0.44 | | 16.23 ± 2.70 | |
| Model | — | 2.20 ± 0.14# | 51.58↑ | 27.54 ± 3.32# | 69.73↑ |
| Benazepril | 4.0 | 1.92 ± 0.29 | 12.50↓ | 20.99 ± 1.58* | 23.78↓ |
| Losartan | 10.0 | 2.15 ± 0.51 | 2.31↓ | 23.88 ± 2.94 | 13.30↓ |
| Com.149 | 5.0 | 1.58 ± 0.49* | 28.24↓ | 23.71 ± 4.17 | 13.92↓ |
| | 10.0 | 1.61 ± 0.36* | 26.50↓ | 20.76 ± 1.56* | 24.61↓ |
| | 20.0 | 1.60 ± 0.14* | 27.27↓ | 20.77 ± 2.04* | 24.58↓ |

Note:
*P < 0.05, compared with model group;
P < 0.05, compared with control group;
↑increase, ↓decrease.

In this assay, the improvement of each biochemical index with compound 149 treatment are more significant than those of the Losartan group, and equivalent to those of the Benazepril group. There was slight different in the pathological changes: the inflammatory cell infiltration in the Benazepril group was more significant, and 4/7 of the animals had focal abscess formations in the medulla of kidney, many kidney cell necrosis and inflammatory cells and abscess cells overlapped in the Benazepril group. The inflammatory cell infiltration and tubulointerstitial fibrosis were significantly attenuated in both compound 149 and the Losartan groups. That is to say, compound 149 is better than Benazepril and equivalent with Losartan in the pathological results.

Example 5

Primary Acute Toxicity Test for Test Compound 5 g/kg and 10 g/kg of compound 149 were administered orally to mice once and observed for 14 days. Body weights of 48 hours after administration in mice were no different. At 14$^{th}$ day after administration, the mouse average body weights in 5 g/kg and 10 g/kg groups increased 7 g and 5 g respectively. There was no any other different for every animal and no death were observed.

Example 6

Ames Test

His$^-$ type *Salmonella typhimurium* TA97, TA98, TA100 and TA102 were employed. Concentration of the test compound was 0.5, 5.0, 50.0, 500.0, 5000.0 μg/plate. S9 was the microsome component of liver homogenate of a rat weighted 200 g. The test compound 149 was tested in the presence or absence of S9.

According to the *Salmonella typhimurium*/mammalian microsome enzyme mutagenic test method revised by Ames (1983), metabolism activated or non-metabolism activated plate incorporation assay was conducted on compound 149, and the strain which passed the assay was seeded to the culture medium and incubated at 37° C. under shaking for 15 hours. 100 μl compound solutions with various concentrations were added to 0.1 ml of the culture liquid, and then S9 mixture or phosphate buffer was added, and the mixtures were incubated in a 37° C. water bath for 20 minutes. After that, 2 ml of upper layer agar was added, mixed well and poured into a plate with lower layer agar and incubated at 37° C. for 48 hours. The number of the colonies in each plate was counted.

The results show that the number of colony formation of *Salmonella Typhimurium* TA97, TA98, TA100 and TA102 induced by compound 149 did not increase. It suggests that compound 149 has no mutagenesis.

The invention claimed is:

1. A compound represented by formula (I)

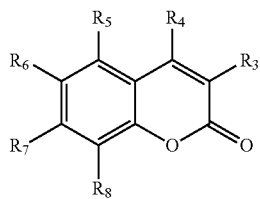

(I)

wherein $R^3$ is CONHR$_9$, wherein R$_9$ is un-substituted or mono- or multi-substituted phenyl wherein the substituent is selected from the group consisting of hydroxyl, C$_1$-C$_8$ alkoxyl, CF$_3$, carboxyl, alkyloxycarbonyl, OCH$_2$CO$_2$H, NO$_2$, halogen, SO$_3$H, SO$_2$NHR$_{11}$, wherein R$_{11}$ is selected from the group consisting of hydrogen, amidino, 2"-thiazolyl, 3"-(5"-methylisooxazolyl), 2"-pyrimidinyl, 2"-(4",6"-dimethylpyrimidinyl), and 4"-(5",6"-dimethoxypyrimidinyl);

R$_4$ is hydrogen;

R$_5$ is selected from the group consisting of H and C$_1$-C$_4$ alkyl;

R$_6$ is selected from the group consisting of H, C$_1$-C$_{12}$ alkyl, halogen, NO$_2$, and CONHR$_{13}$, wherein R$_{13}$ is substituted phenyl;

R$_7$ is selected from the group consisting of hydroxyl, C$_1$-C$_4$ alkyl and alkoxyl;

R$_8$ is selected from the group consisting of H, C$_1$-C$_4$ alkyl or alkoxyl, and NO$_2$;

and when R$_5$, R$_6$ and R$_8$ are H, R$_7$ is OCH$_3$;

or a pharmaceutically acceptable salt or hydrate thereof.

2. The compound according to claim 1, wherein R$_3$ is CONHR$_9$, wherein R$_9$ is selected from n-butyric acid, o-, m-, p-hydroxyphenyl, o-, m-, p-carboxyl-phenyl, o-, m-, p-alkyloxycarbophenyl, methoxylphenyl, 3'-hydroxy-4'-carboxyphenyl, 3'-salicylyl, 4'-salicylyl, m-CF$_3$-phenyl, 3'-CF$_3$-4'-NO$_2$-phenyl, 3'-carboxy-methylenoxyphenyl, 4'-aminosulfonylphenyl, 4'-guanidinosulfonylphenyl, 4'-(2"-thiazolaminosulfonyl)phenyl, 4'-(5"-methylisooxazolyl-3"-amino sulfonyl)phenyl, 4'-(pyrimidinyl-2"-amino sulfonyl) phenyl, 4'-(4",6"-dimethylpyrimidinyl-2"-amino sulfonyl) phenyl, and 4'-(5",6"-dimethoxypyrimidinyl-4"-amino sulfonyl)phenyl;

R$_4$ is hydrogen;

R$_5$ is selected from the group consisting of H and CH$_3$;

R$_6$ is selected from the group consisting of H, C$_2$H$_5$, n-C$_6$H$_{13}$, NO$_2$, Cl, Br, and CONHR$_{13}$, wherein R$_{13}$ is selected from the group consisting of 4-benzoic acid and ethyl 4-benzoate;

R$_7$ is selected from the group consisting of H, OH, CH$_3$, and OCH$_3$; and

R$_8$ is selected from the group consisting of H, CH$_3$, OCH$_3$, and NO$_2$.

3. The compound according to claim 1, wherein the compound of formula I is represented by formula (Ib)

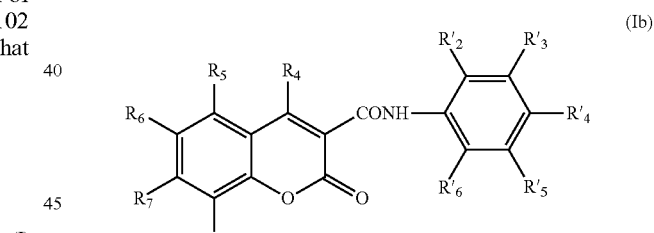

(Ib)

wherein R$_4$, R$_5$, R$_6$, R$_7$, R$_8$, are as defined in claim 1,

R'$_2$ is selected from the group consisting of H, OH, and CO$_2$H,

R'$_3$ is selected from the group consisting of H, OH, CO$_2$H, CF$_3$, and OCH$_2$CO$_2$H, R'$_4$ is selected from the group consisting of H, OH, CO$_2$H, CO$_2$Et, iodo, NO$_2$, OCH$_3$, SO$_3$H, SO$_2$NH$_2$, SONH(C=NH)NH$_2$,

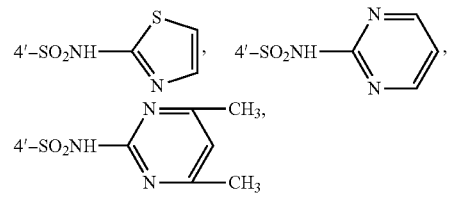

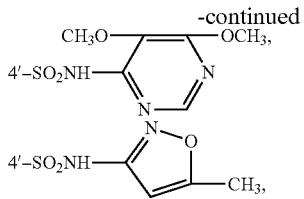

and

R'$_5$, and R'$_6$ are each H.

4. The compound according to claim 2, wherein R$_3$, R$_4$, R$_5$, R$_6$, R$_7$, and R$_8$ are respectively selected from one of the combinations in the group consisting of:

R$_3$=p-CO$_2$H-phenylamino carbonyl, R$_4$=R$_5$=R$_6$=R$_8$=H, R$_7$=OCH$_3$;
R$_3$=m-CO$_2$H-phenylamino carbonyl, R$_4$=R$_5$=R$_6$=R$_8$=H, R$_7$=OCH$_3$;
R$_3$=o-CO$_2$H-phenylamino carbonyl, R$_4$=R$_5$=R$_6$=R$_8$=H, R$_7$=OCH$_3$;
R$_3$=o-OH-phenylamino carbonyl, R$_4$=R$_5$=R$_6$=R$_8$=H, R$_7$=OCH$_3$;
R$_3$=m-OH-phenylamino carbonyl, R$_4$=R$_5$=R$_6$=R$_8$=H, R$_7$=OCH$_3$;
R$_3$=p-OH-phenylamino carbonyl, R$_4$=R$_5$=R$_6$=R$_8$=H, R$_7$=OCH$_3$;
R$_3$=m-OH-p-CO$_2$H-phenylamino carbonyl, R$_4$=R$_5$=R$_6$=R$_8$=H, R$_7$=OCH$_3$;
R$_3$=m-CO$_2$H-p-OH-phenylamino carbonyl, R$_4$=R$_5$=R$_6$=R$_8$=H, R$_7$=OCH$_3$;
R$_3$=o-CO$_2$H-p-I-phenylamino carbonyl, R$_4$=R$_5$=R$_6$=R$_8$=H, R$_7$=OCH$_3$;
R$_3$=4'-ethoxycarbonylphenylaminocarbonyl, R$_4$=R$_5$=R$_6$=R$_8$=H, R$_7$=OCH$_3$;
R$_3$=m-CF$_3$-phenylaminocarbonyl, R$_4$=R$_5$=R$_6$=R$_8$=H, R$_7$=OCH$_3$;
R$_3$=m-CF$_3$-p-NO$_2$-phenylaminocarbonyl, R$_4$=R$_5$=R$_6$=R$_8$=H, R$_7$=OCH$_3$;
R$_3$=4'-amino sulfonylphenylamino carbonyl, R$_4$=R$_5$=R$_6$=R$_8$=H, R$_7$=OCH$_3$;
R$_3$=4'-guanidinosulfonylphenylaminocarbonyl, R$_4$=R$_5$=R$_6$=R$_8$=H, R$_7$=OCH$_3$;
R$_3$=4'-(2"-thiazolaminosulfonyl)phenylaminocarbonyl, R$_4$=R$_5$=R$_6$=R$_8$=H, R$_7$=OCH$_3$;
R$_3$=4'-(2"-pyrimidinylamino aminosulfonyl)phenylamino carbonyl, R$_4$=R$_5$=R$_6$=R$_8$=H, R$_7$=OCH$_3$;
R$_3$=4'-[2"-(4",6"-dimethylpyrimidinylaminosulfonyl)] phenylamino carbonyl, R$_4$=R$_5$=R$_6$=R$_8$=H, R$_7$=OCH$_3$;
R$_3$=4'-(5",6"-dimethoxypyrimidinyl-4"-amino sulfonyl) phenylamino carbonyl, R$_4$=R$_5$=R$_6$=R$_8$=H, R$_7$=OCH$_3$;
R$_3$=4'-(5"-methyl-isooxazol-3"-aminosulfonyl)phenylamino carbonyl, R$_4$=R$_5$=R$_6$=R$_8$=H, R$_7$=OCH$_3$;
R$_3$=p-OCH$_3$-phenylamino carbonyl, R$_4$=R$_5$=R$_6$=R$_8$=H, R$_7$=OCH$_3$;
R$_3$=p-SO$_3$H-phenylamino carbonyl, R$_4$=R$_5$=R$_6$=R$_8$=H, R$_7$=OCH$_3$;
R$_3$=p-CO$_2$H-phenylamino carbonyl, R$_4$=R$_5$=R$_8$=H, R$_6$=C$_2$H$_5$, R$_7$=OCH$_3$;
R$_3$=m-CO$_2$H-phenylamino carbonyl, R$_4$=R$_5$=R$_8$=H, R$_6$=C$_2$H$_5$, R$_7$=OCH$_3$;
R$_3$=o-CO$_2$H-phenylamino carbonyl, R$_4$=R$_5$=R$_8$=H, R$_6$=C$_2$H$_5$, R$_7$=OCH$_3$;
R$_3$=p-OH-phenylamino carbonyl, R$_4$=R$_5$=R$_8$=H, R$_6$=C$_2$H$_5$, R$_7$=OCH$_3$;
R$_3$=m-OH-p-CO$_2$H-phenylamino carbonyl, R$_4$=R$_5$=R$_8$=H, R$_6$=C$_2$H$_5$, R$_7$=OCH$_3$;
R$_3$=m-CO$_2$H-p-OH-phenylamino carbonyl, R$_4$=R$_5$=R$_8$=H, R$_6$=C$_2$H$_5$, R$_7$=OCH$_3$;
R$_3$=4'-ethoxycarbonylphenylamino carbonyl, R$_4$=R$_5$=R$_8$=H, R$_6$=C$_2$H$_5$, R$_7$=OCH$_3$;
R$_3$=m-CF$_3$-phenylamino carbonyl, R$_4$=R$_5$=R$_8$=H, R$_6$=C$_2$H$_5$, R$_7$=OCH$_3$;
R$_3$=m-CF$_3$-4-NO$_2$-phenylamino carbonyl, R$_4$=R$_5$=R$_8$=H, R$_6$=C$_2$H$_5$, R$_7$=OCH$_3$;
R$_3$=4'-amino sulfonylphenylamino carbonyl, R$_4$=R$_5$=R$_8$=H, R$_6$=C$_2$H$_5$, R$_7$=OCH$_3$;
R$_3$=4'-guanidinosulfonylphenylamino carbonyl, R$_4$=R$_5$=R$_8$=H, R$_6$=C$_2$H$_5$, R$_7$=OCH$_3$;
R$_3$=4'-(2"-thiazolaminosulfonyl)phenylaminocarbonyl, R$_4$=R$_5$=R$_8$=H, R$_6$=C$_2$H$_5$, R$_7$=OCH$_3$;
R$_3$=4'-(2"-pyrimidinylaminosulfonyl)phenylaminocarbonyl, R$_4$=R$_5$=R$_8$=H, R$_6$=C$_2$H$_5$, R$_7$=OCH$_3$;
R$_3$=4'-(4",6"-dimethylpyrimidinyl-2"-aminosulfonyl)phenylamino carbonyl, R$_4$=R$_5$=R$_8$=H, R$_6$=C$_2$H$_5$, R$_7$=OCH$_3$;
R$_3$=4'-(5",6"-dimethoxypyrimidinyl-4"-aminosulfonyl) phenylamino carbonyl, R$_4$=R$_5$=R$_8$=H, R$_6$=C$_2$H$_5$, R$_7$=OCH$_3$
R$_3$=4'-(5"-CH$_3$-isooxazol-3"-aminosulfonyl)phenylaminocarbonyl, R$_4$=R$_5$=R$_8$=H, R$_6$=C$_2$H$_5$, R$_7$=OCH$_3$;
R$_3$=p-OCH$_3$-phenylaminocarbonyl, R$_4$=R$_5$=R$_8$=H, R$_6$=C$_2$H$_5$, R$_7$=OCH$_3$;
R$_3$=p-SO$_3$H-phenylaminocarbonyl, R$_4$=R$_5$=R$_8$=H, R$_6$=C$_2$H$_5$, R$_7$=OCH$_3$;
R$_3$=p-CO$_2$H-phenylaminocarbonyl, R$_4$=R$_5$=R$_6$=H, R$_7$=OCH$_3$, R$_8$=CH$_3$;
R$_3$=m-CO$_2$H-phenylaminocarbonyl, R$_4$=R$_5$=R$_6$=H, R$_7$=OCH$_3$, R$_8$=CH$_3$;
R$_3$=o-CO$_2$H-phenylaminocarbonyl, R$_4$=R$_5$=R$_6$=H, R$_7$=OCH$_3$, R$_8$=CH$_3$;
R$_3$=m-OH-p-CO$_2$H-phenylaminocarbonyl, R$_4$=R$_5$=R$_6$=H, R$_7$=OCH$_3$, R$_8$=CH$_3$;
R$_3$=m-CO$_2$H-p-OH-phenylaminocarbonyl, R$_4$=R$_5$=R$_6$=H, R$_7$=OCH$_3$, R$_8$=CH$_3$;
R$_3$=o-CO$_2$H-p-I-phenylaminocarbonyl, R$_4$=R$_5$=R$_6$=H, R$_7$=OCH$_3$, R$_8$=CH$_3$;
R$_3$=p-ethoxycarbophenylaminocarbonyl, R$_4$=R$_5$=R$_6$=H, R$_7$=OCH$_3$, R$_8$=CH$_3$;
R$_3$=m-CF$_3$-phenylaminocarbonyl, R$_4$=R$_5$=R$_6$=H, R$_7$=OCH$_3$, R$_8$=CH$_3$;
R$_3$=m-CF$_3$-4-NO$_2$-phenylaminocarbonyl, R$_4$=R$_5$=R$_6$=H, R$_7$=OCH$_3$, R$_8$=CH$_3$;
R$_3$=4'-aminosulfonylphenylamino carbonyl, R$_4$=R$_5$=R$_6$=H, R$_7$=OCH$_3$, R$_8$=CH$_3$;
R$_3$=4'-guanidinosulfonylphenylaminocarbonyl, R$_4$=R$_5$=R$_6$=H, R$_7$=OCH$_3$, R$_8$=CH$_3$;
R$_3$=4'-(2"-thiazolaminosulfonyl)phenylaminocarbonyl, R$_4$=R$_5$=R$_6$=H, R$_7$=OCH$_3$, R$_8$=CH$_3$;
R$_3$=4'-(2"-pyrimidinylaminosulfonyl)phenylaminocarbonyl, R$_4$=R$_5$=R$_6$=H, R$_7$=OCH$_3$, R$_8$=CH$_3$;
R$_3$=4'-(4",6"-dimethylpyrimidinyl-2"-aminosulfonyl) phenylamino carbonyl, R$_4$=R$_5$=R$_6$=H, R$_7$=OCH$_3$, R$_8$=CH$_3$;
R$_3$=4'-(5",6"-dimethoxypyrimidinyl-4"-aminosulfonyl) phenylamino carbonyl, R$_4$=R$_5$=R$_6$=H, R$_7$=OCH$_3$, R$_8$=CH$_3$;
R$_3$=4'-(5"-CH$_3$-isooxazol-3"-aminosulfonyl)phenylaminocarbonyl, R$_4$=R$_5$=R$_6$=H, R$_7$=OCH$_3$, R$_8$=CH$_3$;
R$_3$=p-OCH$_3$-phenylaminocarbonyl, R$_4$=R$_5$=R$_6$=H, R$_7$=OCH$_3$, R$_8$=CH$_3$;

$R_3$=p-$SO_3$H-phenylaminocarbonyl, $R_4$=$R_5$=$R_6$=H, $R_7$=$OCH_3$, $R_8$=$CH_3$;

$R_3$=p-$CO_2$H-phenylaminocarbonyl, $R_4$=$R_5$=$R_6$=H, $R_7$=$R_8$=$OCH_3$;

$R_3$=m-OH-p-$CO_2$H-phenylaminocarbonyl, $R_4$=$R_5$=$R_6$=H, $R_7$=$R_8$=$OCH_3$;

$R_3$=m $CO_2$H-p-OH-phenylaminocarbonyl, $R_4$=$R_5$=$R_6$=H, $R_7$=$R_8$=$OCH_3$;

$R_3$=p-ethoxycarbophenylaminocarbonyl, $R_4$=$R_5$=$R_6$=H, $R_7$=$R_8$=$OCH_3$;

$R_3$=m-$CF_3$-phenylaminocarbonyl, $R_4$=$R_5$=$R_6$=H, $R_7$=$R_8$=$OCH_3$;

$R_3$=m-$CF_3$-p-$NO_2$-phenylaminocarbonyl, $R_4$=$R_5$=$R_6$=H, $R_7$=$R_8$=$OCH_3$;

$R_3$=m-$HO_2CCH_2O$-phenylaminocarbonyl, $R_4$=$R_5$=$R_6$=H, $R_7$=$R_8$=$OCH_3$;

$R_3$=4'-aminosulfonylphenylaminocarbonyl, $R_4$=$R_5$=$R_6$=H, $R_7$=$R_8$=$OCH_3$;

$R_3$=4'-guanidinosulfonylphenylaminocarbonyl, $R_4$=$R_5$=$R_6$=H, $R_7$=$R_8$=$OCH_3$;

$R_3$=p-$CO_2$H-phenylaminocarbonyl, $R_4$=$R_6$=$R_8$=H, $R_5$=$CH_3$, $R_7$=$OCH_3$;

$R_3$=m-$CO_2$H-phenylaminocarbonyl, $R_4$=$R_6$=$R_8$=H, $R_5$=$CH_3$, $R_7$=$OCH_3$;

$R_3$=o-$CO_2$H-phenylaminocarbonyl, $R_4$=$R_6$=$R_8$=H, $R_5$=$CH_3$, $R_7$=$OCH_3$;

$R_3$=o-OH-phenylaminocarbonyl, $R_4$=$R_6$=$R_8$=H, $R_5$=$CH_3$, $R_7$=$OCH_3$;

$R_3$=m-OH-phenylaminocarbonyl, $R_4$=$R_6$=$R_8$=H, $R_5$=$CH_3$, $R_7$=$OCH_3$;

$R_3$=p-OH-phenylaminocarbonyl, $R_4$=$R_6$=$R_8$=H, $R_5$=$CH_3$, $R_7$=$OCH_3$;

$R_3$=m-OH-p-$CO_2$H-phenylaminocarbonyl, $R_4$=$R_6$=$R_8$=H, $R_5$=$CH_3$, $R_7$=$OCH_3$;

$R_3$=m-$CO_2$H-p-OH-phenylaminocarbonyl, $R_4$=$R_6$=$R_8$=H, $R_5$=$CH_3$, $R_7$=$OCH_3$;

$R_3$=p-ethoxycarbophenylaminocarbonyl, $R_4$=$R_6$=$R_8$=H, $R_5$=$CH_3$, $R_7$=$OCH_3$;

$R_3$=m-$CF_3$-phenylaminocarbonyl, $R_4$=$R_6$=$R_8$=H, $R_5$=$CH_3$, $R_7$=$OCH_3$;

$R_3$=m-$CF_3$-p-$NO_2$-phenylaminocarbonyl, $R_4$=$R_6$=$R_8$=H, $R_5$=$CH_3$, $R_7$=$OCH_3$;

$R_3$=4'-aminosulfonylphenylaminocarbonyl, $R_4$=$R_6$=$R_8$=H, $R_5$=$CH_3$, $R_7$=$OCH_3$;

$R_3$=4'-guanidinosulfonylphenylaminocarbonyl, $R_4$=$R_6$=$R_8$=H, $R_5$=$CH_3$, $R_7$=$OCH_3$;

$R_3$=4'-(2"-thiazolaminosulfonyl)phenylaminocarbonyl, $R_4$=$R_6$=$R_8$=H, $R_5$=$CH_3$, $R_7$=$OCH_3$;

$R_3$=4'-(2"-pyrimidinylamino sulfonyl)phenylaminocarbonyl, $R_4$=$R_6$=$R_8$=H, $R_5$=$CH_3$, $R_7$=$OCH_3$;

$R_3$=4'-(4",6"-dimethylpyrimidinyl-2"-amino sulfonyl) phenylamino carbonyl, $R_4$=$R_6$=$R_8$=H, $R_5$=$CH_3$, $R_7$=$OCH_3$;

$R_3$=4'-(5",6"-dimethoxypyrimidinyl-4"-aminosulfonyl) phenylamino carbonyl, $R_4$=$R_6$=$R_8$=H, $R_5$=$CH_3$, $R_7$=$OCH_3$;

$R_3$=4'-(5"-$CH_3$-isooxazol-3"-aminosulfonyl)phenylaminocarbonyl, $R_4$=$R_6$=$R_8$=H, $R_5$=$CH_3$, $R_7$=$OCH_3$;

$R_3$=p-$OCH_3$-phenylaminocarbonyl, $R_4$=$R_6$=$R_8$=H, $R_5$=$CH_3$, $R_7$=$OCH_3$;

$R_3$=p-$CO_2$H-phenylaminocarbonyl, $R_4$=$R_5$=$R_8$=H, $R_6$=Cl, $R_7$=$OCH_3$;

$R_3$=m-OH-p-$CO_2$H-phenylaminocarbonyl, $R_4$=$R_5$=$R_8$=H, $R_6$=Cl, $R_7$=$OCH_3$;

$R_3$=m-$CO_2$H-p-OH-phenylaminocarbonyl, $R_4$=$R_5$=$R_8$=H, $R_6$=Cl, $R_7$=$OCH_3$;

$R_3$=p-ethoxycarbophenylaminocarbonyl, $R_4$=$R_5$=$R_8$=H, $R_6$=Cl, $R_7$=$OCH_3$;

$R_3$=m-$CF_3$-phenylaminocarbonyl, $R_4$=$R_5$=$R_8$=H, $R_6$=0, $R_7$=$OCH_3$;

$R_3$=4'-aminosulfonylphenylaminocarbonyl, $R_4$=$R_5$=$R_8$=H, $R_6$=Cl, $R_7$=$OCH_3$;

$R_3$=4'-guanidinosulfonylphenylaminocarbonyl, $R_4$=$R_5$=$R_8$=H, $R_6$=Cl, $R_7$=$OCH_3$;

$R_3$=4'-(5",6"-dimethoxypyrimidinyl-4"-aminosulfonyl) phenylamino carbonyl, $R_4$=$R_5$=$R_8$=H, $R_6$=Cl, $R_7$=$OCH_3$;

$R_3$=p-$CO_2$H-aminocarbonyl, $R_4$=$R_5$=$R_8$=H, $R_6$=Br, $R_7$=$OCH_3$;

$R_3$=o-$CO_2$H-phenylaminocarbonyl, $R_4$=$R_5$=$R_8$=H, $R_6$=Br, $R_7$=$OCH_3$;

$R_3$=m-OH-p-$CO_2$H-phenylaminocarbonyl, $R_4$=$R_5$=$R_8$=H, $R_6$=Br, $R_7$=$OCH_3$;

$R_3$=o-$CO_2$H-p-I-phenylaminocarbonyl, $R_4$=$R_5$=$R_8$=H, $R_6$=Br, $R_7$=$OCH_3$;

$R_3$=p-ethoxycarbophenylaminocarbonyl, $R_4$=$R_5$=$R_8$=H, $R_6$=Br, $R_7$=$OCH_3$;

$R_3$=m-$CF_3$-phenylaminocarbonyl, $R_4$=$R_5$=$R_8$=H, $R_6$=Br, $R_7$=$OCH_3$;

$R_3$=4'-aminosulfonylphenylamino carbonyl, $R_4$=$R_5$=$R_8$=H, $R_6$=Br, $R_7$=$OCH_3$;

$R_3$=p-$OCH_3$-phenylaminocarbonyl, $R_4$=$R_5$=$R_8$=H, $R_6$=Br, $R_7$=$OCH_3$;

$R_3$=p-$CO_2$H-phenylaminocarbonyl, $R_4$=$R_5$=$R_8$=H, $R_6$=n-Hex, $R_7$=$OCH_3$;

$R_3$=o-$CO_2$H-phenylaminocarbonyl, $R_4$=$R_5$=$R_8$=H, $R_6$=n-Hex, $R_7$=$OCH_3$;

$R_3$=m-OH-p-$CO_2$H-phenylaminocarbonyl, $R_4$=$R_5$=$R_8$=H, R=Hex, $R_7$=$OCH_3$;

$R_3$=o-$CO_2$H-p-I-phenylaminocarbonyl, $R_4$=$R_5$=$R_8$=H, $R_6$=n-Hex, $R_7$=$OCH_3$;

$R_3$=p-ethoxycarbophenylaminocarbonyl, $R_4$=$R_5$=$R_8$=H, $R_6$=Hex, $R_7$=$OCH_3$;

$R_3$=m-$CF_3$-phenylaminocarbonyl, $R_4$=$R_5$=$R_8$=H, $R_6$=Hexyl, $R_7$=$OCH_3$;

$R_3$=4'-aminosulfonylphenylaminocarbonyl, $R_4$=$R_5$=$R_8$=H, $R_6$=Hex, $R_7$=$OCH_3$;

$R_3$=p-$OCH_3$-phenylaminocarbonyl, $R_4$=$R_5$=$R_8$=H, $R_6$=Hex, $R_7$=$OCH_3$;

$R_3$=p-$CO_2$H-phenylaminocarbonyl, $R_4$=$R_5$=H, $R_6$=$NO_2$, $R_7$=$R_8$=$OCH_3$;

$R_3$=m-$CO_2$H-phenylaminocarbonyl, $R_4$=$R_5$, $R_6$=$NO_2$, $R_7$=$R_8$=$OCH_3$;

$R_3$=p-$OCH_3$-phenylaminocarbonyl, $R_4$=$R_5$=H, $R_6$=$NO_2$, $R_7$=$R_8$=$OCH_3$;

$R_3$=m-OH-phenylaminocarbonyl, $R_4$=$R_5$=H, $R_6$=$NO_2$, $R_7$=$R_8$=$OCH_3$;

$R_3$=o-OH-phenylaminocarbonyl, $R_4$=$R_5$=H, $R_6$=$NO_2$, $R_7$=$R_8$=$OCH_3$;

$R_3$=p-ethoxycarbophenylaminocarbonyl, $R_4$=$R_5$=H, $R_6$=$NO_2$, $R_7$=$R_8$=$OCH_3$;

$R_3$=m-OH-p-$CO_2$H-phenylaminocarbonyl, $R_4$=$R_5$=H, $R_6$=$NO_2$, $R_7$=$R_8$=$OCH_3$;

$R_3$=m-$CO_2$H-p-OH-phenylaminocarbonyl, $R_4$=$R_5$=H, $R_6$=$NO_2$, $R_7$=$R_8$=$OCH_3$;

$R_3$=m-$CF_3$-phenylaminocarbonyl, $R_4$=$R_5$=H, $R_6$=$NO_2$, $R_7$=$R_8$=$OCH_3$;

$R_3$=m-$CF_3$-p-$NO_2$-phenylaminocarbonyl, $R_4$=$R_5$=H, $R_6$=$NO_2$, $R_7$=$R_8$=$OCH_3$;

$R_3$=4'-aminosulfonylphenylamino carbonyl, $R_4$=$R_5$=H, $R_6$=$NO_2$, $R_7$=$R_8$=$OCH_3$;

$R_3$=4'-guanidinosulfonylphenylaminocarbonyl, $R_4$=$R_5$=H, $R_6$=$NO_2$, $R_7$=$R_8$=$OCH_3$;

$R_3$=4'-(2"-pyrimidinylaminosulfonyl)phenylaminocarbonyl, $R_4$=$R_5$=H, $R_6$=NO$_2$, $R_7$=$R_8$=OCH$_3$;

$R_3$=4'-(5",6"-dimethoxypyrimidinyl-4"-aminosulfonyl)phenylamino carbonyl, $R_4$=$R_5$=H, $R_6$=NO$_2$, $R_7$=$R_8$=OCH$_3$;

$R_3$=4'-(2"-thiazolaminosulfonyl)phenylaminocarbonyl, $R_4$=$R_5$=H, $R_6$=NO$_2$, $R_7$=$R_8$=OCH$_3$;

$R_3$=p-CO$_2$H-phenylaminocarbonyl, $R_4$=$R_5$=H, $R_6$=C$_2$H$_5$, $R_7$=OH, $R_8$=NO$_2$;

$R_3$=p-OCH$_3$-phenylaminocarbonyl, $R_4$=$R_5$=H, $R_6$=C$_2$H$_5$, $R_7$=OH, $R_8$=NO$_2$;

$R_3$=m-OH-phenylaminocarbonyl, $R_4$=$R_5$=H, $R_6$=C$_2$H$_5$, $R_7$=OH, $R_8$=NO$_2$;

$R_3$=o-OH-phenylaminocarbonyl, $R_4$=$R_5$=H, $R_6$=C$_2$H$_5$, $R_7$=OH, $R_8$=NO$_2$;

$R_3$=p-ethoxycarbophenylaminocarbonyl, $R_4$=$R_5$=H, $R_6$=C$_2$H$_5$, $R_7$=OH, $R_8$=NO$_2$;

$R_3$=m-OH-p-CO$_2$H-phenylaminocarbonyl, $R_4$=$R_5$=H, $R_6$=C$_2$H$_5$, $R_7$=OH, $R_8$=NO$_2$;

$R_3$=m-CO$_2$H-p-OH-phenylaminocarbonyl, $R_4$=$R_5$=H, $R_6$=C$_2$H$_5$, $R_7$=OH, $R_8$=NO$_2$;

$R_3$=m-CF$_3$— phenylamino carbonyl, $R_4$=$R_5$=H, $R_6$=C$_2$H$_5$, $R_7$=OH, $R_8$=NO$_2$;

$R_3$=4'-aminosulfonylphenylaminocarbonyl, $R_4$=$R_5$=H, $R_6$=C$_2$H$_5$, $R_7$=OH, $R_8$=NO$_2$;

$R_3$=4'-guanidinosulfonylphenylaminocarbonyl, $R_4$=$R_5$=H, $R_6$=C$_2$H$_5$, $R_7$=OH, $R_8$=NO$_2$;

$R_3$=4'-(2"-thiazolaminosulfonyl)phenylaminocarbonyl, $R_4$=$R_5$=H, $R_6$=C$_2$H$_5$, $R_7$=OH, $R_8$=NO$_2$;

$R_3$=p-CO$_2$H-phenylaminocarbonyl, $R_4$=$R_5$=H, $R_6$=C$_2$H$_5$, $R_7$=OCH$_3$, $R_8$=NO$_2$;

$R_3$=p-OH-phenylaminocarbonyl, $R_4$=$R_5$=H, $R_6$=C$_2$H$_5$, $R_7$=OCH$_3$, $R_8$=NO$_2$;

$R_3$=p-OCH$_3$-phenylaminocarbonyl, $R_4$=$R_5$=H, $R_6$=C$_2$H$_5$, $R_7$=OCH$_3$, $R_8$=NO$_2$;

$R_3$=p-ethoxycarbophenylaminocarbonyl, $R_4$=$R_5$=H, $R_6$=C$_2$H$_5$, $R_7$=OH, $R_8$=NO$_2$;

$R_3$=4'-guanidinosulfonylphenylaminocarbonyl, $R_4$=$R_5$=H, $R_6$=C$_2$H$_5$, $R_7$=OCH$_3$; $R_8$=NO$_2$;

$R_3$=p-CO$_2$H-phenylaminocarbonyl, $R_4$=$R_5$=H, $R_6$=NO$_2$, $R_7$=OH, $R_8$=CH$_3$;

$R_3$=o-CO$_2$H-phenylaminocarbonyl, $R_4$=$R_5$=H, $R_6$=NO$_2$, $R_7$=OH, $R_8$=CH$_3$;

$R_3$=p-OH-phenylaminocarbonyl, $R_4$=$R_5$=H, $R_6$=NO$_2$, $R_7$=OH, $R_8$=CH$_3$;

$R_3$=m-OH-phenylaminocarbonyl, $R_4$=$R_5$=H, $R_6$=NO$_2$, $R_7$=OH, $R_8$=CH$_3$;

$R_3$=o-OH-phenylaminocarbonyl, $R_4$=$R_5$=H, $R_6$=NO$_2$, $R_7$=OH, $R_8$=CH$_3$;

$R_3$=p-OCH$_3$-phenylaminocarbonyl, $R_4$=$R_5$=H, $R_6$=NO$_2$, $R_7$=OH, $R_8$=CH$_3$;

$R_3$=p-ethoxycarbophenylaminocarbonyl, $R_4$=$R_5$=H, $R_6$=NO$_2$, $R_7$=OH, $R_8$=CH$_3$;

$R_3$=m-OH-p-CO$_2$H-phenylaminocarbonyl, $R_4$=$R_5$=H, $R_6$=NO$_2$, $R_7$=OH, $R_8$=CH$_3$;

$R_3$=m-CO$_2$H-p-OH-phenylaminocarbonyl, $R_4$=$R_5$=H, $R_6$=NO$_2$, $R_7$=OH, $R_8$=CH$_3$ $R_3$=m-CF$_3$-phenylaminocarbonyl, $R_4$=$R_5$=H, $R_6$=NO$_2$, $R_7$=OH, $R_8$=CH$_3$ $R_3$=m-CF$_3$-p-NO$_2$-phenylaminocarbonyl, $R_4$=$R_5$=H, $R_6$=NO$_2$, $R_7$=OH, $R_8$=CH$_3$ $R_3$=4'-aminosulfonylphenylaminocarbonyl, $R_4$=$R_5$=H, $R_6$=NO$_2$, $R_7$=OH, $R_8$=CH$_3$;

$R_3$=4'-guanidinosulfonylphenylaminocarbonyl, $R_4$=$R_5$=H, $R_6$=NO$_2$, $R_7$=OH, $R_8$=CH$_3$;

$R_3$=4'-(2"-pyrimidinylaminosulfonyl)phenylaminocarbonyl, $R_4$=$R_5$=H, $R_6$=NO$_2$, $R_7$=OH, $R_8$=CH$_3$;

$R_3$=4'-(5",6"-dimethoxypyrimidinyl-4"-aminosulfonyl)phenylamino carbonyl, $R_4$=$R_5$=H, $R_6$=NO$_2$, $R_7$=OH, $R_8$=CH$_3$;

$R_3$=4'-(2"-thiazolaminosulfonyl)phenylaminocarbonyl, $R_4$=$R_5$=H, $R_6$=NO$_2$, $R_7$=OH, $R_8$=CH$_3$;

$R_3$=o-CO$_2$H-p-I-phenylaminocarbonyl, $R_4$=$R_5$=H, $R_6$=NO$_2$, $R_7$=OH, $R_8$=CH$_3$;

$R_3$=p-CO$_2$H-phenylaminocarbonyl, $R_4$=$R_5$=H, $R_6$=NO$_2$, $R_7$=OCH$_3$, $R_8$=CH$_3$;

$R_3$=m-CO$_2$H-phenylaminocarbonyl, $R_4$=$R_5$=H, $R_6$=NO$_2$, $R_7$=OCH$_3$, $R_8$=CH$_3$;

$R_3$=o-CO$_2$H-phenylaminocarbonyl, $R_4$=$R_5$=H, $R_6$=NO$_2$, $R_7$=OCH$_3$, $R_8$=CH$_3$;

$R_3$=p-OH-phenylaminocarbonyl, $R_4$=$R_5$=H, $R_6$=NO$_2$, $R_7$=OCH$_3$, $R_8$=CH$_3$;

$R_3$=m-OH-phenylaminocarbonyl, $R_4$=$R_5$=H, $R_6$=NO$_2$, $R_7$=OCH$_3$, $R_8$=CH$_3$;

$R_3$=o-OH-phenylaminocarbonyl, $R_4$=$R_5$=H, $R_6$=NO$_2$, $R_7$=OCH$_3$, $R_8$=CH$_3$;

$R_3$=p-OCH$_3$-phenylaminocarbonyl, $R_4$=$R_5$=H, $R_6$=NO$_2$, $R_7$=OCH$_3$, $R_8$=CH$_3$;

$R_3$=p-ethoxycarbophenylaminocarbonyl, $R_4$=$R_5$=H, $R_6$=NO$_2$, $R_7$=OCH$_3$, $R_8$=CH$_3$;

$R_3$=m-OH-p-CO$_2$H-phenylaminocarbonyl, $R_4$=$R_5$=H, $R_6$=NO$_2$, $R_7$=OCH$_3$, $R_8$=CH$_3$;

$R_3$=m-CF$_3$-phenylaminocarbonyl, $R_4$=$R_5$=H, $R_6$=NO$_2$, $R_7$=OCH$_3$, $R_8$=CH$_3$;

$R_3$=m-CF$_3$-p-NO$_2$-phenylaminocarbonyl, $R_4$=$R_5$=H, $R_6$=NO$_2$, $R_7$=OCH$_3$, $R_8$=CH$_3$;

$R_3$=4'-guanidinosulfonylphenylaminocarbonyl, $R_4$=$R_5$=H, $R_6$=NO$_2$, $R_7$=OCH$_3$, $R_8$=CH$_3$;

$R_3$=4'-aminosulfonylphenylaminocarbonyl, $R_4$=$R_5$=H, $R_6$=NO$_2$, $R_7$=OCH$_3$, $R_8$=CH$_3$;

$R_3$=4'-(5",6"-dimethoxypyrimidinyl-4"-aminosulfonyl)phenylamino carbonyl, $R_4$=$R_5$=H, $R_6$=NO$_2$, $R_7$=OCH$_3$, $R_8$=CH$_3$;

$R_3$=4'-(2"-thiazolaminosulfonyl)phenylaminocarbonyl, $R_4$=$R_5$=H, $R_6$=NO$_2$, $R_7$=OCH$_3$, $R_8$=CH$_3$;

$R_3$=4'-(2"-pyrimidinylamino sulfonyl)phenylaminocarbonyl, $R_4$=$R_5$=H, $R_6$=NO$_2$, $R_7$=OCH$_3$, $R_8$=CH$_3$;

$R_3$=p-CO$_2$H-phenylaminocarbonyl, $R_4$=$R_5$=H, $R_6$=$R_8$=NO$_2$, $R_7$=OH;

$R_3$=p-OH-phenylaminocarbonyl, $R_4$=$R_5$=H, $R_6$=$R_8$=NO$_2$, $R_7$=OH;

$R_3$=m-OH-phenylaminocarbonyl, $R_4$=$R_5$=H, $R_6$=$R_8$=NO$_2$, $R_7$=OH;

$R_3$=o-OH-phenylaminocarbonyl, $R_4$=$R_5$=H, $R_6$=$R_8$=NO$_2$, $R_7$=OH;

$R_3$=p-OCH$_3$-phenylaminocarbonyl, $R_4$=$R_5$=H, $R_6$=$R_8$=NO$_2$, $R_7$=OH;

$R_3$=p-ethoxycarbophenylaminocarbonyl, $R_4$=$R_5$=H, $R_6$=$R_8$=NO$_2$, $R_7$=OH;

$R_3$=CF$_3$-phenylaminocarbonyl, $R_4$=$R_5$=H, $R_6$=$R_8$=NO$_2$, $R_7$=OH;

$R_3$=4'-aminosulfonylphenylaminocarbonyl, $R_4$=$R_5$=H, $R_6$=$R_8$=NO$_2$, $R_7$=OH;

$R_3$=4'-guanidinosulfonylphenylaminocarbonyl, $R_4$=$R_5$=H, $R_6$=$R_8$=NO$_2$, $R_7$=OH;

$R_3$=4'-(2"-pyrimidinylamino aminosulfonyl)phenylaminocarbonyl, $R_4$=$R_5$=H, $R_6$=$R_8$=NO$_2$, $R_7$=OH;

$R_3$=4'-(5",6"-dimethoxypyrimidinyl-4"-aminosulfonyl)phenylamino carbonyl, $R_4$=$R_5$=H, $R_6$=$R_8$=NO$_2$, $R_7$=OH;

$R_3$=4'-(2"-thiazolaminosulfonyl)phenylaminocarbonyl, $R_4$=$R_5$=H, $R_6$=$R_8$=NO$_2$, $R_7$=OH;

$R_3$=o-CO$_2$H-phenylaminocarbonyl, $R_4$=$R_5$=H, $R_6$=$R_8$=NO$_2$, $R_7$=OH;

$R_3$=p-OH-phenylaminocarbonyl, $R_4$=$R_5$=H, $R_6$=$R_8$=NO$_2$, $R_7$=OCH$_3$;
$R_3$=p-ethoxycarbophenylaminocarbonyl, $R_4$=$R_5$=H, $R_6$=$R_8$=NO$_2$, $R_7$=OCH$_3$;
$R_3$=p-OCH$_3$-phenylaminocarbonyl, $R_4$=$R_5$=H, $R_6$=$R_8$=NO$_2$, $R_7$=OCH$_3$;
$R_3$=p-OCH$_3$-phenylaminocarbonyl, $R_4$=$R_5$=H, $R_6$=Cl, $R_7$=OH, $R_8$=NO$_2$;
$R_3$=4'-guanidinosulfonylphenylaminocarbonyl, $R_4$=$R_5$=H, $R_6$=Cl, $R_7$=OH, $R_8$=NO$_2$;
$R_3$=m-OH-pCO$_2$H-phenylaminocarbonyl, $R_4$=H, $R_5$=CH$_3$, $R_7$=OH, $R_6$=Cl, $R_8$=NO$_2$;
$R_3$=p-CO$_2$H-phenylaminocarbonyl, $R_4$=H, $R_5$=CH$_3$, $R_7$=OH, $R_6$=$R_8$=NO$_2$;
$R_3$=m-CO$_2$H-phenylaminocarbonyl, $R_4$=H, $R_5$=CH$_3$, $R_7$=OH, $R_6$=$R_8$=NO$_2$;
$R_3$=o-CO$_2$H-phenylaminocarbonyl, $R_4$=H, $R_5$=CH$_3$, $R_7$=OH, $R_6$=$R_8$=NO$_2$;
$R_3$=p-OCH$_3$-phenylaminocarbonyl, $R_4$=H, $R_5$=CH$_3$, $R_7$=OH, $R_6$=$R_8$=NO$_2$;
$R_3$=p-ethoxycarbophenylaminocarbonyl, $R_4$=H, $R_5$=CH$_3$, $R_7$=OH, $R_6$=$R_8$=NO$_2$;
$R_3$=p-aminosulfonylphenylaminocarbonyl, $R_4$=H, $R_5$=CH$_3$, $R_7$=OH, $R_6$=$R_8$=NO$_2$; and
$R_3$=p-guanidinosulfonylphenylaminocarbonyl, $R_4$=H, $R_5$=CH$_3$, $R_7$=OH, $R_6$=$R_8$=NO$_2$.

5. A method for preparing a compound according to claim 1, comprising the steps of condensing the substituted 3-carboxy-, or 6-carboxy-coumarin, derivative with a corresponding substituted amine.

6. The method according to claim 1, wherein the reactants for the amidation reaction are selected from the group consisting of phosphorus trichloride, phosphorus oxychloride, phosphorus pentachloride, thionyl chloride, 1,3-dichyclohexylcarbodiimide, dipyridylcarbonate (2-DPC), 1,3-diisopropylcarbodiimide (DIPC), and 1-(3-dimethylamino-propyl)-3-ethylcarbodiimide (EDC1) and the catalytic agent used is selected from the group consisting of tert-amines, pyridine, 4-dimethylaminopyridine and pyrrolalkylpyridine; and the organic solvents used comprise dimethylsulfoxide, dichloromethane, toluene, ethylene glycol dimethyl ether, 1,2-dichloroethane, tetrahydrofuran and N,N-dimethylformamide.

7. A pharmaceutical comprising a pharmaceutically effective dosage of a compound according to claim 1 and a pharmaceutically acceptable carrier.

8. The pharmaceutical composition according to claim 7 wherein the pharmaceutical composition is a tablet, capsule, pH, injection, sustained-release, controlled-release or targeted preparation; and fine particle delivery systems.

9. A method for inhibiting transforming growth factor β1 comprising administering an amount of a compound according to claim 1 effective to inhibit transforming growth factor β1 receptor.

10. A method for inhibiting angiotensin II (AngII) receptor converting enzyme comprising administering an amount of a compound according to claim 1 effective to inhibit angiotensin II (AngII) converting enzyme.

11. A method for treating a chronic renal disorder comprising administering an effective amount of a compound according to claim 1 to a subject in need thereof.

12. A method for treating cardio-cerebrovascular disease comprising administering an effective amount of a compound according to claim 1 to a subject in need thereof.

13. A method for treating non-insulin dependent diabetes comprising administering an effective amount of a compound according to claim 1 to a subject in need thereof.

14. The method according to claim 12, wherein the cardio-cerebrovascular disease is hypertension, cerebral embolism, coronary embolism, myocardial infarction, cerebrovascular accident, or stroke or a sequelae thereof.

15. A method for treating a tumor and pre-cancerous lesion comprising administering an effective amount of a compound according to claim 8 to a subject in need thereof.

16. A pharmaceutical comprising a pharmaceutically effective dosage of a compound according to claim 4 and a pharmaceutically acceptable carrier.

* * * * *

UNITED STATES PATENT AND TRADEMARK OFFICE
CERTIFICATE OF CORRECTION

PATENT NO. : 8,338,401 B2
APPLICATION NO. : 10/537711
DATED : December 25, 2012
INVENTOR(S) : Shiping Xu et al.

It is certified that error appears in the above-identified patent and that said Letters Patent is hereby corrected as shown below:

In the Claims

In claim 6 at column 63, line 31, "The method according to claim 1" should read
--The method according to claim 5--.

Signed and Sealed this
Twenty-seventh Day of August, 2013

Teresa Stanek Rea
*Acting Director of the United States Patent and Trademark Office*